US011891418B2

(12) United States Patent
Vogl et al.

(10) Patent No.: US 11,891,418 B2
(45) Date of Patent: Feb. 6, 2024

(54) YEAST CELL

(71) Applicant: BISY E.U., Hofstätten/Raab (AT)

(72) Inventors: Thomas Vogl, Graz (AT); Anton Glieder, Hofstätten an der Raab (AT)

(73) Assignee: BISY E.U., Hofstätten/Raab (AT)

( * ) Notice: Subject to any disclaimer, the term of this patent is extended or adjusted under 35 U.S.C. 154(b) by 267 days.

(21) Appl. No.: 16/065,377

(22) PCT Filed: Dec. 22, 2016

(86) PCT No.: PCT/EP2016/082398
§ 371 (c)(1),
(2) Date: Jun. 22, 2018

(87) PCT Pub. No.: WO2017/109082
PCT Pub. Date: Jun. 29, 2017

(65) Prior Publication Data
US 2021/0355173 A1 Nov. 18, 2021

(30) Foreign Application Priority Data
Dec. 22, 2015 (EP) .................................... 15202233

(51) Int. Cl.
*C07K 14/39* (2006.01)
*C12N 9/02* (2006.01)
*C12P 21/02* (2006.01)

(52) U.S. Cl.
CPC ............ *C07K 14/39* (2013.01); *C12N 9/0093* (2013.01); *C12P 21/02* (2013.01)

(58) Field of Classification Search
None
See application file for complete search history.

(56) References Cited

U.S. PATENT DOCUMENTS 7,048,930 B2 * 5/2006 Bosman .................. A61P 31/14 424/193.1
7,238,356 B2 * 7/2007 Bosman ............... C07K 14/005 424/193.1
7,718,398 B2 * 5/2010 Suckow ................. C07K 14/39 435/254.22

FOREIGN PATENT DOCUMENTS

WO WO0056903 9/2000
WO WO03095653 11/2003

OTHER PUBLICATIONS

Vogl et al. (AMB Expr., 2020, 10:38, pp. 2-9).*
Tyurin et al. (Mcirobiol. 2015, vol. 84, No. 3, pp. 408-411).*

* cited by examiner

*Primary Examiner* — Hope A Robinson
(74) *Attorney, Agent, or Firm* — Workman Nydegger

(57) ABSTRACT

The present invention relates to a yeast cell of the *Komagataella* genus comprising an orthologous promoter of a methylotrophic yeast cell or a variant thereof inducible by derepression, wherein the orthologous promoter is an orthologous formate dehydrogenase (FMD) promoter of a methylotrophic yeast cell.

13 Claims, 6 Drawing Sheets

Figure 1:
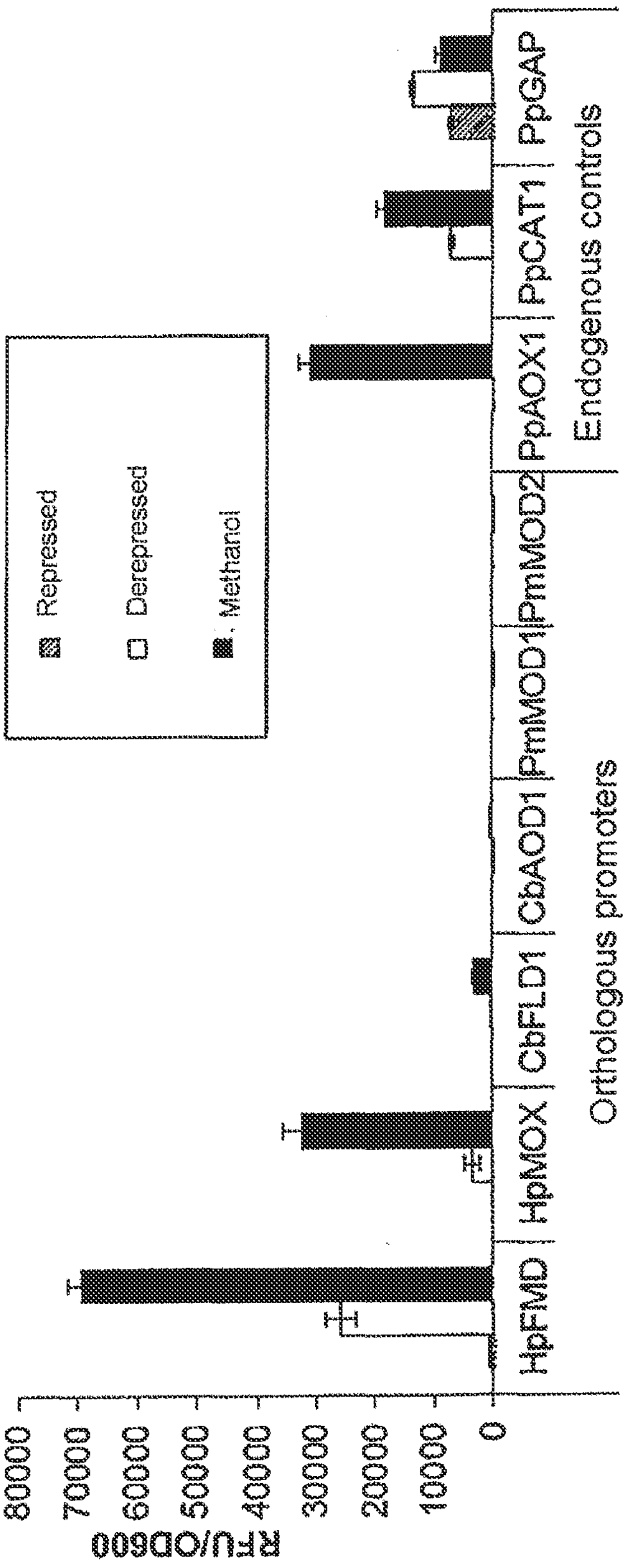

Specification includes a Sequence Listing.

YEAST CELL

CROSS-REFERENCE TO RELATED APPLICATIONS

This application is a 371 application of PCT application no. PCT/EP2016/082398, filed Dec. 22, 2016, which claims the benefit of and priority to European patent application no. EP 15202233.1, filed Dec. 22, 2015, the entirety of each of which is incorporated herein by specific reference.

INCORPORATION OF SEQUENCE LISTING

The instant Application includes a Sequence Listing submitted electronically in ASCII format and is hereby incorporated by this reference in its entirety. The Sequence Listing, created Jun. 29, 2021, is named "16785-181 2021-06-30-Replacement-SeqList" and is 50.5 kb in size.

DETAILED DESCRIPTION

The present invention relates to the use of orthologous promoters in yeast cells.

Recombinant proteins such as biopharmaceuticals or industrially relevant biocatalysts are produced most commonly by means of heterologous gene expression in microorganisms. *Escherichia coli Saccharomyces cerevisiae* and filamentous fungi have been used frequently and for a long time for recombinant protein production. In the last two decades, the methylotrophic yeasts *Komagataella (Pichia) pastoris Komagataella (Pichia) phaffii* (Pp)r *Komagataella* Kurtzmaniir *Ogataea (Hansenula) polymorpha* (Hp)r *Candida boidinii* (Cb) and *Ogataea (Pichia) methanolica* (Pm) have become established as efficient alternative production strains. These strains make it possible to achieve high expression rates for heterologous proteins with a high cell density. Of the aforementioned four yeast species, *P. pastoris (Komagataella phaffii)* has in the meantime been used most commonly for heterologous protein production.

All methylotrophic yeasts have strictly regulated strong promoters which are involved in the regulation of expression of genes of methanol utilization (MUT). Promoters of genes of methanal utilization are usually repressed on repressing carbon sources such as glucose and are greatly upregulated in the presence of methanol as a carbon source. If the repressing carbon source is depleted or in the presence of a non-repressing carbon source, then the promoter is activated by derepression, whereby the strength of this effect can vary greatly between species and even within the same organism. The promoter of the alcohol oxidase-1-gene in *P. pastoris* GS115 (PPpAOX1), for example, has only a 2-4% activity under derepressing conditions in comparison with methanol-induced conditions. In contrast thereto the promoter of the orthologous gene (methanol oxidase, MOX) in *H. polymorpha* (PHpMOX) has an activity of up to 70% under depressing conditions in comparison with methanol-induced conditions. Also the promoters of the orthologous gene in *C. boidinii* (alcohol oxidase 1, AOD1) and *P. methanolica* (methanol oxidase 1/2, MOD1/2) have a comparable behavior.

Induction of expression with toxic and flammable methanol is undesirable especially on a large industrial scale for reasons of operational safety so that strong derepressed promoters constitute a favorable alternative. Accordingly PPpAOX1 variants, alternative promoters and novel MUT promoters with different derepressing properties have been developed recently to enable a methanol-free protein expression on an industrial scale. Since the rates of expression of such promoters are usually much lower in comparison with methanol-induced promoters, one object of the present invention is to make available alternative possibilities for inducible and strong methanol-free overexpression of recombinant proteins in yeasts such as *P. pastoris*.

This object is achieved with a yeast cell of the *Komagataella* genus comprising an orthologous promoter of a methylotrophic yeast cell or a variant thereof that can be induced by derepression, wherein the orthologous promoter is an orthologous formate dehydrogenase (FMD) or a methanol oxidase (MOX) promoter of a methylotrophic yeast cell; in this process, the orthologous promoter in the methylotrophic yeast cell is capable of controlling the expression of polypeptides under derepressing conditions.

This object is also achieved with a yeast cell of the *Komagataella (Pichia)* genus comprising an orthologous formate dehydrogenase (FMD) promoter and/or a methanol oxidase (MOX) promoter of a methylotrophic yeast cell or variants of these two promoters, wherein the original regulation profile of the orthologous promoter in yeast cells of the *Komagataella* genus is retained.

It has surprisingly been found that promoters capable of controlling the expression of polypeptides under derepressing conditions in other methylotrophic yeast cells, which preferably do not belong to the *Komagataella (Pichia)* genus, are capable of controlling the expression of polypeptides under derepressing conditions (for example, increasing expression in comparison with non-derepressing conditions), also have comparable properties in yeast cells of the *Komagataella (Pichia)* genus.

Furthermore, it has surprisingly been found that a formate dehydrogenase (FMD) promoter and/or a methanol oxidase (MOX) promoter of a methylotrophic yeast cell that does not occur naturally in a yeast cell of the *Komagataella* genus and/or in the same yeast cell has special properties in such a cell. An orthologous FMD and/or MOX promoter is significantly stronger in *Komagataella* cells under both derepressing conditions and under methanol-induced conditions than all the naturally occurring promoters and *Komagataella* that are involved in the regulation of the expression of genes of methanol utilization ("MUT promoters") and have been tested so far. Thus, an orthologous FMD and/or MOX promoter is significantly stronger under derepressing conditions than the CAT1 and GAP promoters occurring naturally in *Komagataella* cells, for example. Orthologous FMD and/or MOX promoters are surprisingly even just as strong as the AOX (AOX1 and AOX2) promoters occurring naturally in *Komagataella* under methanol-induced conditions under the screening conditions used under derepressing conditions than the AOX promoters used under methanol-inducing conditions. Such effects can usually be intensified under controlled C-source doses in a bioreactor experiment. Orthologous FMD and/or MOX promoters can replace the AOX promoters generally used in *Komagataella*. Essentially identical or even higher protein expression yields can be achieved in this way in comparison with traditional methanol-induced expression systems but without using any methanol as the induction agent. It is surprising here that a formate dehydrogenase (FMD) promoter of a methylotrophic yeast cell (for example, of *H. polymorpha*) which is also significantly derepressed in this yeast cell (for example, in *H. polymorpha*), retains this regulation profile even in another methylotrophic yeast cell (for example, *P. pastoris*). In contrast thereto earlier studies have shown that in a transfer of promoters between methylotrophic yeasts, the regulation profile of the foreign promoter is not transferred (for example, the *P. pastoris* AOX1 promoter, for example, is not stringently repressed in *H. polymorpha* as it is naturally in *P. pastoris*; see, for example, W. C. Raschke et al. Gene 177 (1996):163-167 and L. Rodriguez et al. Yeast 12 (1996):815-822) Accordingly, the current opinion in the technical world is that different types of regulation between methylotrophic yeast cells do not occur due to the promoter sequence but instead due to different regulation mechanisms in the yeast cells (see, for example, F. S. Hartner et al. Microb. Cell Fact 5 (2006):39-59). However, it has surprisingly been found that the strong activation of a formate dehydrogenase (FMD) promoter of a methylotrophic yeast cell (for example, of *H. polymorpha*) due to derepression can be transferred not only to other methylotrophic yeast cells, such as, for example, *Komagataella phaffii*, but instead even exceeds the technical properties of the strong homologous promoters such as that of the AOX1 gene and CAT1 gene.

Use of orthologous promoter sequences also has other technical advantages. For example, the possibility of homologous recombination is reduced by their use, resulting in a higher genetic stability of the expression strains.

"Yeast cell of the *Komagataella* genus" includes all yeast cells of this genus, such as *Komagataella kurtzmanii, Komagataella pastoris, Komagataella phaffii, Komagataella populi, Komagataella pseudopastoris, Komagataella ulmi* and *Komagataella* sp. 11-1192. "Yeast cells of the *Komagataella* genus" naturally also include those from specific strains of the genus as mentioned above, such as, for example, *Komagataella pastoris* GS115, X-33, KM71, KM71H, CBS7435 or NRLL Y11430, CBS704, BG10, BG11 and/or other derivatives of these strains.

The term "orthologous", as used herein, relates to nucleic acid or amino acid molecules from different species, which at least have functional homology with corresponding nucleic and amino acid molecules of other species. "Orthologs" come from different organisms which occur due to generation and are also derived from a common predecessor. The sequences of the "orthologs" can vary significantly among one another, but the biological and/or biochemical function thereof is usually not affected (for example, AOX from *Komagataella pastoris* is orthologous with MOX from *Hansenula polymorpha* and vice versa, FMD from *Hansenula polymorpha* is orthologous to FDH1 in *Komagataella pastoris* and vice versa).

The term "promoter", as used herein, includes at least one transcription initiation start site, a binding site for a nucleic acid polymerase complex and additional nucleotides so that these two elements can be functionally active and may retain the original regulation profile of the starting cell of the orthologous promoter in yeast cells of the *Komagataella* genus. These additional nucleotides may form transcription factor binding sites, for example. A "promoter inducible by derepression" is a promoter that is activated under derepressing conditions (see below), so that nucleic acid molecules operably linked to it are transcribed so that they code for heterologous or homologous polypeptides.

The orthologous promoters according to the invention, i.e. the orthologous FMD and/or MOX promoter, preferably comprise between 50 and 2000, even more preferably between 100 and 1000, even more preferably between 150 and 800 nucleotides from the region before the start codon (upstream from the 5' end) of the region of the corresponding gene comprising the promoter and coding for a protein/polypeptide, preferably the region of the FMD and/or MOX gene which codes for FMD and/or MOX which may comprise 1 to 1000, preferably 1 to 900, even more preferably 1 to 800 nucleotides. The orthologous promoter, preferably the orthologous FMD and/or MOX promoter, comprises preferably nucleotides 1 to 1000, preferably 1 to 900, even more preferably 1 to 800, upstream from the 5' end of the region of the gene that codes for the polypeptide, preferably the region of the FMD and/or MOX gene that codes for FMD and/or MOX.

"Variants" of the orthologous promoter of the invention, preferably of the orthologous formate dehydrogenase (FMD) promoter and/or of the methanol oxidase (MOX) promoter, include nucleic acid molecules, which differ in one or more (for example, 2, 3, 4, 5, 10, 15, 20, 25, 50) nucleotides from the naturally occurring orthologous promoters, preferably the orthologous FMD and/or MOX promoters. Such promoter variants are at least 80%, preferably at least 90%, even more preferably at least 95%, even more preferably at least 98% identical to the corresponding regions of the naturally occurring promoters.

The variants of orthologous promoters that can be used according to the invention may comprise deletions, substitutions and insertions in comparison with the naturally occurring promoters, preferably FMD and/or MOX promoters. The variants of the promoters also have the property of enabling expression of proteins under derepressing conditions. Variants are preferably used, which are capable of expressing under derepressing conditions at least 50%, preferably at least 60%, even more preferably at least 70%, even more preferably at least 80%, even more preferably at least 90%, even more preferably at least 100%, even more preferably at least 120%, even more preferably at least 150%, of the amount of protein that would be expressed by a yeast cell of the *Komagataella* genus including a naturally occurring orthologous promoter, preferably an orthologous FMD promoter and/or an orthologous MOX promoter.

Methods of identifying and producing promoter variants are sufficiently well known. Mutations are usually introduced into the promoter, whereupon a test is performed showing whether and how the properties (for example, expression rate of a model protein) of the promoter variants have changed.

"Variants" of the orthologous promoter of the present invention, preferably of the orthologous formate dehydrogenase (FMD) promoter and/or of the orthologous methanol oxidase (MOX) promoter, also include promoter variants which include the regulatory elements of the naturally occurring orthologous promoter or variants thereof as defined above (differing in one or more, for example, 2, 3, 4, 5, 10, 15, 20, 25, 50 nucleotides from the naturally occurring sequence) and an alternative minimal promoter and/or core promoter. The minimal promoter and/or core promoter is part of a promoter that contains only the general promoter elements which are necessary for transcription (TATA box and transcription start). Therefore, the regulatory elements of the variants of the orthologous promoters according to the invention include preferably between 100 and 1000, even more preferably between 150 and 800 nucleotides from the region upstream from the start codon (upstream from the 5' end) without 20 to 100, preferably without 25 to 80, even more preferably without 30 to 70, nucleotides directly before the starting point of the transcription.

"Identity" and "identical", respectively, refer to the degree of correspondence between two or more nucleic acid and/or amino acid sequences which can be determined by the correspondence between the sequences. The percentage of "identity" is derived from the percentage of identical regions in two or more sequences, taking into account gaps or other sequence particulars (i.e., % identity refers to the number of identical positions/total number of positions×100). A particularly preferred method for determining identity is the BLAST program of the National Centre for Biotechnology Information (NCBI) (see S. Altschul et al., J Mol Biol 215 (1990):403-410 among others). The BLOSUM62 algorithm is preferably used with the parameters "gap" "existence":11 and "extension":1.

The term "methylotrophic yeast cells", as used herein, includes yeast cells capable of growing on culture media containing as carbon source substances with only one carbon atom, for example methanol.

"Derepressing conditions", as used in culturing the yeast cells according to the invention, means that the yeast cells are first cultured in the presence of a repressing carbon source (e.g. glucose) until this carbon source has been mostly or entirely consumed. After reducing the concentration of the repressing carbon source (e.g. glucose), the cells are in derepressing conditions with respect to the repressing carbon source and glucose, respectively. The strength of the repression effects may depend on the type of carbon source.

According to a preferred embodiment of the present invention the orthologous FMD and/or the orthologous MOX promoter is operably linked to a nucleic acid molecule coding for a heterologous or homologous polypeptide.

The orthologous promoter may be operably linked to a nucleic acid molecule coding for a heterologous (not originating from *Komagataella*) or homologous polypeptide (originating from *Komagataella*) and can thus influence the expression of this polypeptide and/or control it. The resulting polypeptide includes at least 5, preferably at least 10, even more preferably at least 50 amino acid residues and thus includes molecules, which are also referred to as polypeptides or proteins.

The nucleic acid molecule codes preferably for polypeptides such as antibodies or fragments thereof, enzymes, structural proteins, etc.

"Operably linked", as used herein, means that the nucleic acid molecule coding for a heterologous or homologous polypeptide is linked to the promoter in a way which permits expression of the nucleotide sequence in a yeast cell according to the invention. The promoter is thus operably linked to a coding nucleic acid sequence when this has an influence on the transcription of the coding sequence.

According to another preferred embodiment of the present invention, the heterologous or homologous polypeptide comprises a signal peptide, in particular a secretion signal peptide.

To secrete a recombinant homologous or heterologous polypeptide from the yeast cell, the polypeptide encoded by the nucleic acid molecule includes a signal peptide.

The term "signal peptide", as used herein, refers to a peptide linked to the C-terminus or N-terminus of the polypeptide, which controls the secretion of the polypeptide. The signal sequence used in the present invention may be a polynucleotide which codes for an amino acid sequence which initiates the transport of a protein through the membrane of the endoplasmic reticulum (ER). The nucleic acid sequence of these signal sequences may correspond to the natural sequence of the original host cell or may be codon-optimized. The non limited examples of the signal sequence include MF-alpha ("mating factor alpha" signal sequence), the signal sequence of the CBH2 protein from *Trichoderma reesei*, the signal sequence of the xylanase A from *Thermomyces lanuginosus*, K1 killer toxin signal, the signal peptide for invertase secretion, the signal sequence of the killer toxin from *Kluyveromyces lactis*, the signal sequence of the killer toxin from *Pichia acaciae*, the signal sequence of the killer toxin from *Hanseniaspora uvarum* and from *Pichia* (*Hansenula*) *anomala* or variants thereof as described for example, by Cereghino et al. (Gene 519 (2013):311-317). The preferred signal sequence of the invention is MF-alpha ("mating factor alpha" signal sequence).

According to a particularly preferred embodiment of the present invention, the orthologous FMD promoter and/or the orthologous MOX promoter, originates from a methylotrophic yeast cell selected from the group consisting of the genera *Hansenula* (*Ogataea*), *Candida, Komagataella* and *Pichia.*

According to another preferred embodiment of the present invention, the methylotrophic yeast cell is selected from the group consisting of *Hansenula polymorpha, Candida boidinii, Pichia methanolica, Komagataella pastoris, Komagataella phaffii, Komagataella pseudopastoris, Komagataella ulmi* and *Komagataella* sp. 11-1192.

The orthologous FMD and/or MOX promoter and optionally the nucleic acid molecule operably linked thereto, coding for the heterologous or homologous polypeptide, can be present in the genome, as an extrachromosomal nucleic acid construct on a plasmid with autonomously replicating sequence (ARS) or as a vector/expression cassette integrated into the genome.

The orthologous FMD and/or MOX promoter and optionally the nucleic acid molecule operably linked thereto may be present extrachromosomally or integrated into the genome of the yeast cell according to the invention.

According to a particularly preferred embodiment of the present invention, the orthologous promoter comprises or consists of a nucleic acid sequence SEQ ID NO: 1 or SEQ ID NO: 2 or a variant thereof.

```
(FMD promoter):
                                    SEQ ID No. 1
AATGTATCTAAACGCAAACTCCGAGCTGGAAA

AATGTTACCGGCGATGCGCGGACAATTTAGAG

GCGGCGATCAAGAAACACCTGCTGGGCGAGCA

GTCTGGAGCACAGTCTTCGATGGGCCCGAGAT

CCCACCGCGTTCCTGGGTACCGGGACGTGAGG

CAGCGCGACATCCATCAAATATACCAGGCGCC

AACCGAGTCTCTCGGAAAACAGCTTCTGGATA

TCTTCCGCTGGCGGCGCAACGACGAATAATAG

TCCCTGGAGGTGACGGAATATATATGTGTGGA

GGGTAAATCTGACAGGGTGTAGCAAAGGTAAT

ATTTTCCTAAAACATGCAATCGGCTGCCCCGC

AACGGGAAAAAGAATGACTTTGGCACTCTTCA

CCAGAGTGGGGTGTCCCGCTCGTGTGTGCAAA

TAGGCTCCCACTGGTCACCCCGGATTTTGCAG

AAAAACAGCAAGTTCCGGGGTGTCTCACTGGT

GTCCGCCAATAAGAGGAGCCGGCAGGCACGGA

GTCTACATCAAGCTGTCTCCGATACACTCGAC

TACCATCCGGGTCTCTCAGAGAGGGGAATGGC
```

-continued

ACTATAAATACCGCCTCCTTGCGCTCTCTGCC

TTCATCAATCAAATC (MOX promoter):

SEQ ID No. 2

CGACGCGGAGAACGATCTCCTCGAGCTGCTCG

CGGATCAGCTTGTGGCCCGGTAATGGAACCAG

GCCGACGGCACGCTCCTTGCGGACCACGGTGG

CTGGCGAGCCCAGTTTGTGAACGAGGTCGTTT

AGAACGTCCTGCGCAAAGTCCAGTGTCAGATG

AATGTCCTCCTCGGACCAATTCAGCATGTTCT

CGAGCAGCCATCTGTCTTTGGAGTAGAAGCGT

AATCTCTGCTCCTCGTTACTGTACCGGAAGAG

GTAGTTTGCCTCGCCGCCCATAATGAACAGGT

TCTCTTTCTGGTGGCCTGTGAGCAGCGGGGAC

GTCTGGACGGCGTCGATGAGGCCCTTGAGGCG

CTCGTAGTACTTGTTCGCGTCGCTGTAGCCGG

CCGCGGTGACGATACCCACATAGAGGTCCTTG

GCCATTAGTTTGATGAGGTGGGGCAGGATGGG

CGACTCGGCATCGAAATTTTTGCCGTCGTCGT

ACAGTGTGATGTCACCATCGAATGTAATGAGC

TGCAGCTTGCGATCTCGGATGGTTTTGGAATG

GAAGAACCGCGACATCTCCAACAGCTGGGCCG

TGTTGAGAATGAGCCGGACGTCGTTGAACGAG

GGGGCCACAAGCCGGCGTTTGCTGATGGCGCG

GCGCTCGTCCTCGATGTAGAAGGCCTTTTCCA

GAGGCAGTCTCGTGAAGAAGCTGCCAACGCTC

GGAACCAGCTGCACGAGCCGAGACAATTCGGG

GGTGCCGGCTTTGGTCATTTCAATGTTGTCGT

CGATGAGGAGTTCGAGGTCGTGGAAGATTTCC

GCGTAGCGGCGTTTTGCCTCAGAGTTTACCAT

GAGGTCGTCCACTGCAGAGATGCCGTTGCTCT

TCACCGCGTACAGGACGAACGGCGTGGCCAGC

AGGCCCTTGATCCATTCTATGAGGCCATCTCG

ACGGTGTTCCTTGAGTGCGTACTCCACTCTGT

AGCGACTGGACATCTCGAGACTGGGCTTGCTG

TGCTGGATGCACCAATTAATTGTTGCCGCATG

CATCCTTGCACCGCAAGTTTTTAAAACCCACT

CGCTTTAGCCGTCGCGTAAAACTTGTGAATCT

GGCAACTGAGGGGGTTCTGCAGCCGCAACCGA

ACTTTTCGCTTCGAGGACGCAGCTGGATGGTG

TCATGTGAGGCTCTGTTTGCTGGCGTAGCCTA

-continued

CAACGTGACCTTGCCTAACCGGACGGCGCTAC

CCACTGCTGTCTGTGCCTGCTACCAGAAAATC

ACCAGAGCAGCAGAGGGCCGATGTGGCAACTG

GTGGGGTGTCGGACAGGCTGTTTCTCCACAGT

GCAAATGCGGGTGAACCGGCCAGAAAGTAAAT

TCTTATGCTACCGTGCAGTGACTCCGACATCC

CCAGTTTTTGCCCTACTTGATCACAGATGGGG

TCAGCGCTGCCGCTAAGTGTACCCAACCGTCC

CCACACGGTCCATCTATAAATACTGCTGCCAG

TGCACGGTGGTGACATCAATCTAAAGTACAAA

AACAAA

According to a particularly preferred embodiment of the present invention the variant of SEQ No. 1 comprises or consists of SEQ ID NO: 27. SEQ ID NO: 27 has the following nucleic acid sequence:

AATGTATCTAAACGCAAACTCCGAGCTG-GAAAAATGTTACCGGCGATGCGCGGACAATT-TAGAG GCGGCGA$X_1$TCAAGAAACA CCTGCTGGGCGAGCAGTCTG-GAGCACAGTCTTCGATGGGCCCGAGA TCC-CACCGCGTTCCTGGGTACCGGGACGT-GAGGCAGCGCGACATCCATCAAATATACCAGG CGC CAACCGAGTCTCTCGGAAAACA GCTTCTGGATATCTTCCGCTGGCGGCGCAAC GACGAATAATA GTCCCTGGAGGTGACG-GAATATATATGTGTGGAGGGTAAATCTGACAGG GTGTAGCAAAGGTAA TATTTTCCTAAAACATG CAATCGGCTGCCCCGC$X_2$ACGGGAAAAAGAAT GACTTTGGCACTCTTC ACCAGAGTGGGGTGTC CCGCTCGTGTGTGCAAATAGGCTCCCACTGGT-CACCCCGGATTTTGCA GAAAAA$X_3$AG CAAGTTCCGGGGTGTCTCACTGGTGTCCGC-CAATAAGAGGAGCCGGCAGGCACGG AGTCTA-CATCAAGCTGTCTCCGATACACTCGA CTACCA$X_4$CCGGGTCTCTC$X_5X_6X_7X_8X_9X_{10}X_1$ $X_{12}X_{13}X_{14}X_{15}X_{16}X_{17}X_{18}$CAC, wherein $X_1$ is adenine or no nucleotide, $X_2$ is adenine or guanine, $X_3$ is cytosine or thymine, $X_4$ is thymine or guanine, $X_5$ is adenine or cytosine, $X_6$ is guanine or cytosine, $X_7$ is adenine or cytosine, $X_8$ is guanine or cytosine, $X_9$ is adenine, guanine or cytosine, $X_{10}$ is guanine or cytosine, $X_{11}$ is guanine or cytosine, $X_{12}$ is guanine or cytosine, $X_{13}$ is guanine or cytosine, $X_{14}$ is adenine or cytosine, $X_{15}$ is adenine or cytosine, $X_{16}$ is thymine or cytosine, $X_{17}$ is guanine or cytosine, and $X_{18}$ is guanine or cytosine. The CAC end of SEQ ID NO: 27 may also be attached to $X_{19}$, which is a core promoter of an orthologous promoter, preferably of anFMD and/or MOX promoter, particularly preferred a nucleic acid sequence selected from the group consisting of TATAAATACCGCCTCCTTGCGCTCTCTGCCTT-CATCAATCAAATC (SEQ ID NO: 28), TATATAAACTGGTGATAATTCCTTCGTTCT-GAGTTCCATCTCATACTCAAACTATAT-TAAAACTACAACA (SEQ ID NO: 29), TATAAATACAAGACGAGTGCGTCCTTTTCTA-GACTCACCCATAAACAAATAATCAATAAAT (SEQ ID NO: 30), TATAAATACTGCC- TACTTGTCCTCTATTCCTTCATCAATCACATC (SEQ ID NO: 31), CGATAGGGCAGAAATATATAAAGTAGGAGGTTGTATACCAAATATACCAACGCAGTACAAGCAACTCTTGGTTTAAACGGAAGAAACAATTCTTCGAACATTTACAACAAAGAAGGTACCGTAACATTAATAATCGGAAGGGT (SEQ ID NO: 32), GTAATCTTTCGGTCAATTGTGATCTCTCTTGTAGATATTTAATAGGACGGCCAAGGTAGAAAAAGATACATAACTAGTTAGCAAACTTCAATTGCTTAAGTTACAAGTGCAATCCATATCTTAAAGTTATTACATTATTTATA (SEQ ID NO: 33) and CCTCCTCTAGGTTTATCTATAAAAGCTGAAGTCGTTAGAATTTTTCATTTAAAGCATAATCAAACATCTAGATTCGAATCGATAAAAAGCAGATAGAAGTTATTAAGATTATAGGTTACATTCTAGAGTAGTATAGGAAGGTA (SEQ ID NO: 34), in particular SEQ ID NO: 28, SEQ ID NO: 29, SEQ ID NO: 30 and SEQ ID NO:31, in particular SEQ ID NO: 28. At least one nucleotide within SEQ ID NO: 27 is different at the corresponding position of SEQ ID NO: 1, thus resulting in a variant of SEQ ID NO: 1.

It turned surprisingly out that at least one, preferably at least 2, 3, 4, 5, 6, 7, 8, 9 or 10, point mutations (insertions and/or substitutions) within SEQ ID NO: 1 (see SEQ ID NO: 27) result in a promoter variant exhibiting superior effects compared to a promoter region consisting of or comprising SEQ ID NO: 1. Yeast cells comprising such promoters operably linked to a nucleic acid molecule encoding for a polypeptide show at least the same or even an increased expression rate, at least within the first 24 hours of culturing, compared to yeast cells carrying a promoter consisting of SEQ ID NO: 1. Therefore, it is particularly preferred to modify SEQ ID NO: 1 at one or more of the positions indicated in its corresponding nucleic acid sequence SEQ ID NO: 27 as $X_1$ to $X_{18}$ and $X_1$ to $X_{19}$.

Mutations of one or more (2, 3, 4, 5, 6 or 7) of nucleotides $X_1$, $X_3$, $X_4$, $X_5$, $X_9$, $X_{16}$, and $X_{17}$ of SEQ ID NO: 27 resulting in a nucleotide sequence different from SEQ ID NO: 1 are preferred since such promoters show also an increased polypeptide and protein expression compared to the use of SEQ ID NO: 1 after 48 hours of cultivation under derepressing conditions. Particularly preferred are mutations of one or more (2, 3, 4 or 5) of nucleotides $X_1$, $X_4$, $X_9$, $X_{16}$ and $X_{17}$ of SEQ ID NO: 27 resulting in a nucleotide sequence different from SEQ ID NO: 1 since such promoters show also an increased polypeptide and protein expression compared to the use of SEQ ID NO: 1 after 72 hours of cultivation using methanol, for instance, as carbon source.

As mentioned above $X_{19}$ attached to SEQ ID NO: 27 can be the core promoter naturally occurring in SEQ ID NO: 1 (i.e. TATAAATACCGCCTCCTTGCGCTCTCTGCCTTCATCAATCAAATC (SEQ ID NO: 28)) or an alternative core promoter. Particularly preferred core promoters comprise or consist of SEQ ID NO: 29, SEQ ID NO: 30 and SEQ ID NO:31. All these core promoters show in combination with SEQ ID NO: 1 or SEQ ID NO: 27 (the naturally occurring core promoter is substituted with one of these alternative core promoters at the end of SEQ ID NO: 27) a significantly enhanced polypeptide expression rate compared to the promoter encoded by SEQ ID NO: 1 under derepressing conditions.

Particularly preferred variants of SEQ ID NO: 1 are selected from the group consisting of the following nucleic acid sequences:

(v1; see example 2):
SEQ ID NO. 35
AATGTATCTAAACGCAAACTCCGAGCTGGAAA

AATGTTACCGGCGATGCGCGGACAATTTAGAG

GCGGCGAATCAAGAAACACCTGCTGGGCGAGC

AGTCTGGAGCACAGTCTTCGATGGGCCCGAGA

TCCCACCGCGTTCCTGGGTACCGGGACGTGAG

GCAGCGCGACATCCATCAAATATACCAGGCGC

CAACCGAGTCTCTCGGAAAACAGCTTCTGGAT

ATCTTCCGCTGGCGGCGCAACGACGAATAATA

GTCCCTGGAGGTGACGGAATATATATGTGTGG

AGGGTAAATCTGACAGGGTGTAGCAAAGGTAA

TATTTTCCTAAAACATGCAATCGGCTGCCCCG

CAACGGGAAAAAGAATGACTTTGGCACTCTTC

ACCAGAGTGGGGTGTCCCGCTCGTGTGTGCAA

ATAGGCTCCCACTGGTCACCCCGGATTTTGCA

GAAAAACAGCAAGTTCCGGGGTGTCTCACTGG

TGTCCGCCAATAAGAGGAGCCGGCAGGCACGG

AGTCTACATCAAGCTGTCTCCGATACACTCGA

CTACCATCCGGGTCTCTCAGAGAGGGGAATGG

CACTATAAATACCGCCTCCTTGCGCTCTCTGC

CTTCATCAATCAAATC (v2):
SEQ ID NO. 36
AATGTATCTAAACGCAAACTCCGAGCTGGAAA

AATGTTACCGGCGATGCGCGGACAATTTAGAG

GCGGCGATCAAGAAACACCTGCTGGGCGAGCA

GTCTGGAGCACAGTCTTCGATGGGCCCGAGAT

CCCACCGCGTTCCTGGGTACCGGGACGTGAGG

CAGCGCGACATCCATCAAATATACCAGGCGCC

AACCGAGTCTCTCGGAAAACAGCTTCTGGATA

TCTTCCGCTGGCGGCGCAACGACGAATAATAG

TCCCTGGAGGTGACGGAATATATATGTGTGGA

GGGTAAATCTGACAGGGTGTAGCAAAGGTAAT

ATTTTCCTAAAACATGCAATCGGCTGCCCCGC

GACGGGAAAAAGAATGACTTTGGCACTCTTCA

CCAGAGTGGGGTGTCCCGCTCGTGTGTGCAAA

TAGGCTCCCACTGGTCACCCCGGATTTTGCAG

AAAAACAGCAAGTTCCGGGGTGTCTCACTGGT

GTCCGCCAATAAGAGGAGCCGGCAGGCACGGA

-continued

GTCTACATCAAGCTGTCTCCGATACACTCGAC

TACCATCCGGGTCTCTCAGAGAGGGGAATGGC

ACTATAAATACCGCCTCCTTGCGCTCTCTGCC

TTCATCAATCAAATC (v3):

SEQ ID NO. 37

AATGTATCTAAACGCAAACTCCGAGCTGGAAA

AATGTTACCGGCGATGCGCGGACAATTTAGAG

GCGGCGATCAAGAAACACCTGCTGGGCGAGCA

GTCTGGAGCACAGTCTTCGATGGGCCCGAGAT

CCCACCGCGTTCCTGGGTACCGGGACGTGAGG

CAGCGCGACATCCATCAAATATACCAGGCGCC

AACCGAGTCTCTCGGAAAACAGCTTCTGGATA

TCTTCCGCTGGCGGCGCAACGACGAATAATAG

TCCCTGGAGGTGACGGAATATATATGTGTGGA

GGGTAAATCTGACAGGGTGTAGCAAAGGTAAT

ATTTTCCTAAAACATGCAATCGGCTGCCCCGC

AACGGGAAAAAGAATGACTTTGGCACTCTTCA

CCAGAGTGGGGTGTCCCGCTCGTGTGTGCAAA

TAGGCTCCCACTGGTCACCCCGGATTTTGCAG

AAAAATAGCAAGTTCCGGGGTGTCTCACTGGT

GTCCGCCAATAAGAGGAGCCGGCAGGCACGGA

GTCTACATCAAGCTGTCTCCGATACACTCGAC

TACCATCCGGGTCTCTCAGAGAGGGGAATGGC

ACTATAAATACCGCCTCCTTGCGCTCTCTGCC

TTCATCAATCAAATC (v4):

SEQ ID NO. 38

AATGTATCTAAACGCAAACTCCGAGCTGGAAA

AATGTTACCGGCGATGCGCGGACAATTTAGAG

GCGGCGATCAAGAAACACCTGCTGGGCGAGCA

GTCTGGAGCACAGTCTTCGATGGGCCCGAGAT

CCCACCGCGTTCCTGGGTACCGGGACGTGAGG

CAGCGCGACATCCATCAAATATACCAGGCGCC

AACCGAGTCTCTCGGAAAACAGCTTCTGGATA

TCTTCCGCTGGCGGCGCAACGACGAATAATAG

TCCCTGGAGGTGACGGAATATATATGTGTGGA

GGGTAAATCTGACAGGGTGTAGCAAAGGTAAT

ATTTTCCTAAAACATGCAATCGGCTGCCCCGC

AACGGGAAAAAGAATGACTTTGGCACTCTTCA

CCAGAGTGGGGTGTCCCGCTCGTGTGTGCAAA

TAGGCTCCCACTGGTCACCCCGGATTTTGCAG

AAAAACAGCAAGTTCCGGGGTGTCTCACTGGT

-continued

GTCCGCCAATAAGAGGAGCCGGCAGGCACGGA

GTCTACATCAAGCTGTCTCCGATACACTCGAC

TACCATCCGGGTCTCTCAGAGGGGGGAATGGC

ACTATAAATACCGCCTCCTTGCGCTCTCTGCC

TTCATCAATCAAATC (vS):

SEQ ID NO. 39

AATGTATCTAAACGCAAACTCCGAGCTGGAAA

AATGTTACCGGCGATGCGCGGACAATTTAGAG

GCGGCGATCAAGAAACACCTGCTGGGCGAGCA

GTCTGGAGCACAGTCTTCGATGGGCCCGAGAT

CCCACCGCGTTCCTGGGTACCGGGACGTGAGG

CAGCGCGACATCCATCAAATATACCAGGCGCC

AACCGAGTCTCTCGGAAAACAGCTTCTGGATA

TCTTCCGCTGGCGGCGCAACGACGAATAATAG

TCCCTGGAGGTGACGGAATATATATGTGTGGA

GGGTAAATCTGACAGGGTGTAGCAAAGGTAAT

ATTTTCCTAAAACATGCAATCGGCTGCCCCGC

AACGGGAAAAAGAATGACTTTGGCACTCTTCA

CCAGAGTGGGGTGTCCCGCTCGTGTGTGCAAA

TAGGCTCCCACTGGTCACCCCGGATTTTGCAG

AAAAACAGCAAGTTCCGGGGTGTCTCACTGGT

GTCCGCCAATAAGAGGAGCCGGCAGGCACGGA

GTCTACATCAAGCTGTCTCCGATACACTCGAC

TACCAGCCGGGTCTCTCAGAGAGGGGAATGGC

ACTATAAATACCGCCTCCTTGCGCTCTCTGCC

TTCATCAATCAAATC (v6):

SEQ ID NO. 40

AATGTATCTAAACGCAAACTCCGAGCTGGAAA

AATGTTACCGGCGATGCGCGGACAATTTAGAG

GCGGCGATCAAGAAACACCTGCTGGGCGAGCA

GTCTGGAGCACAGTCTTCGATGGGCCCGAGAT

CCCACCGCGTTCCTGGGTACCGGGACGTGAGG

CAGCGCGACATCCATCAAATATACCAGGCGCC

AACCGAGTCTCTCGGAAAACAGCTTCTGGATA

TCTTCCGCTGGCGGCGCAACGACGAATAATAG

TCCCTGGAGGTGACGGAATATATATGTGTGGA

GGGTAAATCTGACAGGGTGTAGCAAAGGTAAT

ATTTTCCTAAAACATGCAATCGGCTGCCCCGC

AACGGGAAAAAGAATGACTTTGGCACTCTTCA

CCAGAGTGGGGTGTCCCGCTCGTGTGTGCAAA

-continued

TAGGCTCCCACTGGTCACCCCGGATTTTGCAG

AAAAACAGCAAGTTCCGGGGTGTCTCACTGGT

GTCCGCCAATAAGAGGAGCCGGCAGGCACGGA

GTCTACATCAAGCTGTCTCCGATACACTCGAC

TACCATCCGGGTCTCTCCGAGAGGGGAATGGC

ACTATAAATACCGCCTCCTTGCGCTCTCTGCC

TTCATCAATCAAATC (v7):

SEQ ID NO. 41

AATGTATCTAAACGCAAACTCCGAGCTGGAAA

AATGTTACCGGCGATGCGCGGACAATTTAGAG

GCGGCGATCAAGAAACACCTGCTGGGCGAGCA

GTCTGGAGCACAGTCTTCGATGGGCCCGAGAT

CCCACCGCGTTCCTGGGTACCGGGACGTGAGG

CAGCGCGACATCCATCAAATATACCAGGCGCC

AACCGAGTCTCTCGGAAAACAGCTTCTGGATA

TCTTCCGCTGGCGGCGCAACGACGAATAATAG

TCCCTGGAGGTGACGGAATATATATGTGTGGA

GGGTAAATCTGACAGGGTGTAGCAAAGGTAAT

ATTTTCCTAAAACATGCAATCGGCTGCCCCGC

AACGGGAAAAAGAATGACTTTGGCACTCTTCA

CCAGAGTGGGGTGTCCCGCTCGTGTGTGCAAA

TAGGCTCCCACTGGTCACCCCGGATTTTGCAG

AAAAACAGCAAGTTCCGGGGTGTCTCACTGGT

GTCCGCCAATAAGAGGAGCCGGCAGGCACGGA

GTCTACATCAAGCTGTCTCCGATACACTCGAC

TACCATCCGGGTCTCTCACAGAGGGGAATGGC

ACTATAAATACCGCCTCCTTGCGCTCTCTGCC

TTCATCAATCAAATC (v8):

SEQ ID NO. 42

AATGTATCTAAACGCAAACTCCGAGCTGGAAA

AATGTTACCGGCGATGCGCGGACAATTTAGAG

GCGGCGATCAAGAAACACCTGCTGGGCGAGCA

GTCTGGAGCACAGTCTTCGATGGGCCCGAGAT

CCCACCGCGTTCCTGGGTACCGGGACGTGAGG

CAGCGCGACATCCATCAAATATACCAGGCGCC

AACCGAGTCTCTCGGAAAACAGCTTCTGGATA

TCTTCCGCTGGCGGCGCAACGACGAATAATAG

TCCCTGGAGGTGACGGAATATATATGTGTGGA

GGGTAAATCTGACAGGGTGTAGCAAAGGTAAT

ATTTTCCTAAAACATGCAATCGGCTGCCCCGC

AACGGGAAAAAGAATGACTTTGGCACTCTTCA

-continued

CCAGAGTGGGGTGTCCCGCTCGTGTGTGCAAA

TAGGCTCCCACTGGTCACCCCGGATTTTGCAG

AAAAACAGCAAGTTCCGGGGTGTCTCACTGGT

GTCCGCCAATAAGAGGAGCCGGCAGGCACGGA

GTCTACATCAAGCTGTCTCCGATACACTCGAC

TACCATCCGGGTCTCTCAGCGAGGGGAATGGC

ACTATAAATACCGCCTCCTTGCGCTCTCTGCC

TTCATCAATCAAATC (v9):

SEQ ID NO. 43

AATGTATCTAAACGCAAACTCCGAGCTGGAAA

AATGTTACCGGCGATGCGCGGACAATTTAGAG

GCGGCGATCAAGAAACACCTGCTGGGCGAGCA

GTCTGGAGCACAGTCTTCGATGGGCCCGAGAT

CCCACCGCGTTCCTGGGTACCGGGACGTGAGG

CAGCGCGACATCCATCAAATATACCAGGCGCC

AACCGAGTCTCTCGGAAAACAGCTTCTGGATA

TCTTCCGCTGGCGGCGCAACGACGAATAATAG

TCCCTGGAGGTGACGGAATATATATGTGTGGA

GGGTAAATCTGACAGGGTGTAGCAAAGGTAAT

ATTTTCCTAAAACATGCAATCGGCTGCCCCGC

AACGGGAAAAAGAATGACTTTGGCACTCTTCA

CCAGAGTGGGGTGTCCCGCTCGTGTGTGCAAA

TAGGCTCCCACTGGTCACCCCGGATTTTGCAG

AAAAACAGCAAGTTCCGGGGTGTCTCACTGGT

GTCCGCCAATAAGAGGAGCCGGCAGGCACGGA

GTCTACATCAAGCTGTCTCCGATACACTCGAC

TACCATCCGGGTCTCTCAGACAGGGGAATGGC

ACTATAAATACCGCCTCCTTGCGCTCTCTGCC

TTCATCAATCAAATC (v10):

SEQ ID NO. 44

AATGTATCTAAACGCAAACTCCGAGCTGGAAA

AATGTTACCGGCGATGCGCGGACAATTTAGAG

GCGGCGATCAAGAAACACCTGCTGGGCGAGCA

GTCTGGAGCACAGTCTTCGATGGGCCCGAGAT

CCCACCGCGTTCCTGGGTACCGGGACGTGAGG

CAGCGCGACATCCATCAAATATACCAGGCGCC

AACCGAGTCTCTCGGAAAACAGCTTCTGGATA

TCTTCCGCTGGCGGCGCAACGACGAATAATAG

TCCCTGGAGGTGACGGAATATATATGTGTGGA

GGGTAAATCTGACAGGGTGTAGCAAAGGTAAT

-continued

ATTTTCCTAAAACATGCAATCGGCTGCCCCGC
AACGGGAAAAAGAATGACTTTGGCACTCTTCA
CCAGAGTGGGGTGTCCCGCTCGTGTGTGCAAA
TAGGCTCCCACTGGTCACCCCGGATTTTGCAG
AAAAACAGCAAGTTCCGGGGTGTCTCACTGGT
GTCCGCCAATAAGAGGAGCCGGCAGGCACGGA
GTCTACATCAAGCTGTCTCCGATACACTCGAC
TACCATCCGGGTCTCTCAGAGCGGGGAATGGC
ACTATAAATACCGCCTCCTTGCGCTCTCTGCC
TTCATCAATCAAATC (v11):

SEQ ID NO. 45
AATGTATCTAAACGCAAACTCCGAGCTGGAAA
AATGTTACCGGCGATGCGCGGACAATTTAGAG
GCGGCGATCAAGAAACACCTGCTGGGCGAGCA
GTCTGGAGCACAGTCTTCGATGGGCCCGAGAT
CCCACCGCGTTCCTGGGTACCGGGACGTGAGG
CAGCGCGACATCCATCAAATATACCAGGCGCC
AACCGAGTCTCTCGGAAAACAGCTTCTGGATA
TCTTCCGCTGGCGGCGCAACGACGAATAATAG
TCCCTGGAGGTGACGGAATATATATGTGTGGA
GGGTAAATCTGACAGGGTGTAGCAAAGGTAAT
ATTTTCCTAAAACATGCAATCGGCTGCCCCGC
AACGGGAAAAAGAATGACTTTGGCACTCTTCA
CCAGAGTGGGGTGTCCCGCTCGTGTGTGCAAA
TAGGCTCCCACTGGTCACCCCGGATTTTGCAG
AAAAACAGCAAGTTCCGGGGTGTCTCACTGGT
GTCCGCCAATAAGAGGAGCCGGCAGGCACGGA
GTCTACATCAAGCTGTCTCCGATACACTCGAC
TACCATCCGGGTCTCTCAGAGACGGGAATGGC
ACTATAAATACCGCCTCCTTGCGCTCTCTGCC
TTCATCAATCAAATC (v12):

SEQ ID NO. 46
AATGTATCTAAACGCAAACTCCGAGCTGGAAA
AATGTTACCGGCGATGCGCGGACAATTTAGAG
GCGGCGATCAAGAAACACCTGCTGGGCGAGCA
GTCTGGAGCACAGTCTTCGATGGGCCCGAGAT
CCCACCGCGTTCCTGGGTACCGGGACGTGAGG
CAGCGCGACATCCATCAAATATACCAGGCGCC
AACCGAGTCTCTCGGAAAACAGCTTCTGGATA
TCTTCCGCTGGCGGCGCAACGACGAATAATAG
TCCCTGGAGGTGACGGAATATATATGTGTGGA

-continued

GGGTAAATCTGACAGGGTGTAGCAAAGGTAAT
ATTTTCCTAAAACATGCAATCGGCTGCCCCGC
AACGGGAAAAAGAATGACTTTGGCACTCTTCA
CCAGAGTGGGGTGTCCCGCTCGTGTGTGCAAA
TAGGCTCCCACTGGTCACCCCGGATTTTGCAG
AAAAACAGCAAGTTCCGGGGTGTCTCACTGGT
GTCCGCCAATAAGAGGAGCCGGCAGGCACGGA
GTCTACATCAAGCTGTCTCCGATACACTCGAC
TACCATCCGGGTCTCTCAGAGAGCGGAATGGC
ACTATAAATACCGCCTCCTTGCGCTCTCTGCC
TTCATCAATCAAATC (v13):

SEQ ID NO. 47
AATGTATCTAAACGCAAACTCCGAGCTGGAAA
AATGTTACCGGCGATGCGCGGACAATTTAGAG
GCGGCGATCAAGAAACACCTGCTGGGCGAGCA
GTCTGGAGCACAGTCTTCGATGGGCCCGAGAT
CCCACCGCGTTCCTGGGTACCGGGACGTGAGG
CAGCGCGACATCCATCAAATATACCAGGCGCC
AACCGAGTCTCTCGGAAAACAGCTTCTGGATA
TCTTCCGCTGGCGGCGCAACGACGAATAATAG
TCCCTGGAGGTGACGGAATATATATGTGTGGA
GGGTAAATCTGACAGGGTGTAGCAAAGGTAAT
ATTTTCCTAAAACATGCAATCGGCTGCCCCGC
AACGGGAAAAAGAATGACTTTGGCACTCTTCA
CCAGAGTGGGGTGTCCCGCTCGTGTGTGCAAA
TAGGCTCCCACTGGTCACCCCGGATTTTGCAG
AAAAACAGCAAGTTCCGGGGTGTCTCACTGGT
GTCCGCCAATAAGAGGAGCCGGCAGGCACGGA
GTCTACATCAAGCTGTCTCCGATACACTCGAC
TACCATCCGGGTCTCTCAGAGAGGCGAATGGC
ACTATAAATACCGCCTCCTTGCGCTCTCTGCC
TTCATCAATCAAATC (v14):

SEQ ID NO. 48
AATGTATCTAAACGCAAACTCCGAGCTGGAAA
AATGTTACCGGCGATGCGCGGACAATTTAGAG
GCGGCGATCAAGAAACACCTGCTGGGCGAGCA
GTCTGGAGCACAGTCTTCGATGGGCCCGAGAT
CCCACCGCGTTCCTGGGTACCGGGACGTGAGG
CAGCGCGACATCCATCAAATATACCAGGCGCC
AACCGAGTCTCTCGGAAAACAGCTTCTGGATA

-continued

TCTTCCGCTGGCGGCGCAACGACGAATAATAG
TCCCTGGAGGTGACGGAATATATATGTGTGGA
GGGTAAATCTGACAGGGTGTAGCAAAGGTAAT
ATTTTCCTAAAACATGCAATCGGCTGCCCCGC
AACGGGAAAAAGAATGACTTTGGCACTCTTCA
CCAGAGTGGGGTGTCCCGCTCGTGTGTGCAAA
TAGGCTCCCACTGGTCACCCCGGATTTTGCAG
AAAAACAGCAAGTTCCGGGGTGTCTCACTGGT
GTCCGCCAATAAGAGGAGCCGGCAGGCACGGA
GTCTACATCAAGCTGTCTCCGATACACTCGAC
TACCATCCGGGTCTCTCAGAGAGGGCAATGGC
ACTATAAATACCGCCTCCTTGCGCTCTCTGCC
TTCATCAATCAAATC (v15):
SEQ ID NO. 49
AATGTATCTAAACGCAAACTCCGAGCTGGAAA
AATGTTACCGGCGATGCGCGGACAATTTAGAG
GCGGCGATCAAGAAACACCTGCTGGGCGAGCA
GTCTGGAGCACAGTCTTCGATGGGCCCGAGAT
CCCACCGCGTTCCTGGGTACCGGGACGTGAGG
CAGCGCGACATCCATCAAATATACCAGGCGCC
AACCGAGTCTCTCGGAAAACAGCTTCTGGATA
TCTTCCGCTGGCGGCGCAACGACGAATAATAG
TCCCTGGAGGTGACGGAATATATATGTGTGGA
GGGTAAATCTGACAGGGTGTAGCAAAGGTAAT
ATTTTCCTAAAACATGCAATCGGCTGCCCCGC
AACGGGAAAAAGAATGACTTTGGCACTCTTCA
CCAGAGTGGGGTGTCCCGCTCGTGTGTGCAAA
TAGGCTCCCACTGGTCACCCCGGATTTTGCAG
AAAAACAGCAAGTTCCGGGGTGTCTCACTGGT
GTCCGCCAATAAGAGGAGCCGGCAGGCACGGA
GTCTACATCAAGCTGTCTCCGATACACTCGAC
TACCATCCGGGTCTCTCAGAGAGGGGCATGGC
ACTATAAATACCGCCTCCTTGCGCTCTCTGCC
TTCATCAATCAAATC (v16):
SEQ ID NO. 50
AATGTATCTAAACGCAAACTCCGAGCTGGAAA
AATGTTACCGGCGATGCGCGGACAATTTAGAG
GCGGCGATCAAGAAACACCTGCTGGGCGAGCA
GTCTGGAGCACAGTCTTCGATGGGCCCGAGAT
CCCACCGCGTTCCTGGGTACCGGGACGTGAGG
CAGCGCGACATCCATCAAATATACCAGGCGCC

-continued

AACCGAGTCTCTCGGAAAACAGCTTCTGGATA
TCTTCCGCTGGCGGCGCAACGACGAATAATAG
TCCCTGGAGGTGACGGAATATATATGTGTGGA
GGGTAAATCTGACAGGGTGTAGCAAAGGTAAT
ATTTTCCTAAAACATGCAATCGGCTGCCCCGC
AACGGGAAAAAGAATGACTTTGGCACTCTTCA
CCAGAGTGGGGTGTCCCGCTCGTGTGTGCAAA
TAGGCTCCCACTGGTCACCCCGGATTTTGCAG
AAAAACAGCAAGTTCCGGGGTGTCTCACTGGT
GTCCGCCAATAAGAGGAGCCGGCAGGCACGGA
GTCTACATCAAGCTGTCTCCGATACACTCGAC
TACCATCCGGGTCTCTCAGAGAGGGGACTGGC
ACTATAAATACCGCCTCCTTGCGCTCTCTGCC
TTCATCAATCAAATC (v17):
SEQ ID NO. 51
AATGTATCTAAACGCAAACTCCGAGCTGGAAA
AATGTTACCGGCGATGCGCGGACAATTTAGAG
GCGGCGATCAAGAAACACCTGCTGGGCGAGCA
GTCTGGAGCACAGTCTTCGATGGGCCCGAGAT
CCCACCGCGTTCCTGGGTACCGGGACGTGAGG
CAGCGCGACATCCATCAAATATACCAGGCGCC
AACCGAGTCTCTCGGAAAACAGCTTCTGGATA
TCTTCCGCTGGCGGCGCAACGACGAATAATAG
TCCCTGGAGGTGACGGAATATATATGTGTGGA
GGGTAAATCTGACAGGGTGTAGCAAAGGTAAT
ATTTTCCTAAAACATGCAATCGGCTGCCCCGC
AACGGGAAAAAGAATGACTTTGGCACTCTTCA
CCAGAGTGGGGTGTCCCGCTCGTGTGTGCAAA
TAGGCTCCCACTGGTCACCCCGGATTTTGCAG
AAAAACAGCAAGTTCCGGGGTGTCTCACTGGT
GTCCGCCAATAAGAGGAGCCGGCAGGCACGGA
GTCTACATCAAGCTGTCTCCGATACACTCGAC
TACCATCCGGGTCTCTCAGAGAGGGGAACGGC
ACTATAAATACCGCCTCCTTGCGCTCTCTGCC
TTCATCAATCAAATC (v18):
SEQ ID NO. 52
AATGTATCTAAACGCAAACTCCGAGCTGGAAA
AATGTTACCGGCGATGCGCGGACAATTTAGAG
GCGGCGATCAAGAAACACCTGCTGGGCGAGCA
GTCTGGAGCACAGTCTTCGATGGGCCCGAGAT

-continued

CCCACCGCGTTCCTGGGTACCGGGACGTGAGG
CAGCGCGACATCCATCAAATATACCAGGCGCC
AACCGAGTCTCTCGGAAAACAGCTTCTGGATA
TCTTCCGCTGGCGGCGCAACGACGAATAATAG
TCCCTGGAGGTGACGGAATATATATGTGTGGA
GGGTAAATCTGACAGGGTGTAGCAAAGGTAAT
ATTTTCCTAAAACATGCAATCGGCTGCCCCGC
AACGGGAAAAAGAATGACTTTGGCACTCTTCA
CCAGAGTGGGGTGTCCCGCTCGTGTGTGCAAA
TAGGCTCCCACTGGTCACCCCGGATTTTGCAG
AAAAACAGCAAGTTCCGGGGTGTCTCACTGGT
GTCCGCCAATAAGAGGAGCCGGCAGGCACGGA
GTCTACATCAAGCTGTCTCCGATACACTCGAC
TACCATCCGGGTCTCTCAGAGAGGGGAATCGC
ACTATAAATACCGCCTCCTTGCGCTCTCTGCC
TTCATCAATCAAATC (v19):

SEQ ID NO. 53

AATGTATCTAAACGCAAACTCCGAGCTGGAAA
AATGTTACCGGCGATGCGCGGACAATTTAGAG
GCGGCGATCAAGAAACACCTGCTGGGCGAGCA
GTCTGGAGCACAGTCTTCGATGGGCCCGAGAT
CCCACCGCGTTCCTGGGTACCGGGACGTGAGG
CAGCGCGACATCCATCAAATATACCAGGCGCC
AACCGAGTCTCTCGGAAAACAGCTTCTGGATA
TCTTCCGCTGGCGGCGCAACGACGAATAATAG
TCCCTGGAGGTGACGGAATATATATGTGTGGA
GGGTAAATCTGACAGGGTGTAGCAAAGGTAAT
ATTTTCCTAAAACATGCAATCGGCTGCCCCGC
AACGGGAAAAAGAATGACTTTGGCACTCTTCA
CCAGAGTGGGGTGTCCCGCTCGTGTGTGCAAA
TAGGCTCCCACTGGTCACCCCGGATTTTGCAG
AAAAACAGCAAGTTCCGGGGTGTCTCACTGGT
GTCCGCCAATAAGAGGAGCCGGCAGGCACGGA
GTCTACATCAAGCTGTCTCCGATACACTCGAC
TACCATCCGGGTCTCTCAGAGAGGGGAATGCC
ACTATAAATACCGCCTCCTTGCGCTCTCTGCC
TTCATCAATCAAATC (v20):

SEQ ID NO. 54

AATGTATCTAAACGCAAACTCCGAGCTGGAAA
AATGTTACCGGCGATGCGCGGACAATTTAGAG
GCGGCGATCAAGAAACACCTGCTGGGCGAGCA

-continued

GTCTGGAGCACAGTCTTCGATGGGCCCGAGAT
CCCACCGCGTTCCTGGGTACCGGGACGTGAGG
CAGCGCGACATCCATCAAATATACCAGGCGCC
AACCGAGTCTCTCGGAAAACAGCTTCTGGATA
TCTTCCGCTGGCGGCGCAACGACGAATAATAG
TCCCTGGAGGTGACGGAATATATATGTGTGGA
GGGTAAATCTGACAGGGTGTAGCAAAGGTAAT
ATTTTCCTAAAACATGCAATCGGCTGCCCCGC
AACGGGAAAAAGAATGACTTTGGCACTCTTCA
CCAGAGTGGGGTGTCCCGCTCGTGTGTGCAAA
TAGGCTCCCACTGGTCACCCCGGATTTTGCAG
AAAAACAGCAAGTTCCGGGGTGTCTCACTGGT
GTCCGCCAATAAGAGGAGCCGGCAGGCACGGA
GTCTACATCAAGCTGTCTCCGATACACTCGAC
TACCATCCGGGTCTCTCAGAGAGGGGAATGGC
ACTATATAAACTGGTGATAATTCCTTCGTTCT
GAGTTCCATCTCATACTCAAACTATATTAAAA
CTACAACA (v21):

SEQ ID NO. 55

AATGTATCTAAACGCAAACTCCGAGCTGGAAA
AATGTTACCGGCGATGCGCGGACAATTTAGAG
GCGGCGATCAAGAAACACCTGCTGGGCGAGCA
GTCTGGAGCACAGTCTTCGATGGGCCCGAGAT
CCCACCGCGTTCCTGGGTACCGGGACGTGAGG
CAGCGCGACATCCATCAAATATACCAGGCGCC
AACCGAGTCTCTCGGAAAACAGCTTCTGGATA
TCTTCCGCTGGCGGCGCAACGACGAATAATAG
TCCCTGGAGGTGACGGAATATATATGTGTGGA
GGGTAAATCTGACAGGGTGTAGCAAAGGTAAT
ATTTTCCTAAAACATGCAATCGGCTGCCCCGC
AACGGGAAAAAGAATGACTTTGGCACTCTTCA
CCAGAGTGGGGTGTCCCGCTCGTGTGTGCAAA
TAGGCTCCCACTGGTCACCCCGGATTTTGCAG
AAAAACAGCAAGTTCCGGGGTGTCTCACTGGT
GTCCGCCAATAAGAGGAGCCGGCAGGCACGGA
GTCTACATCAAGCTGTCTCCGATACACTCGAC
TACCATCCGGGTCTCTCAGAGAGGGGAATGGC
ACTATAAATACAAGACGAGTGCGTCCTTTTCT
AGACTCACCCATAAACAAATAATCAATAAAT

-continued (v22):
SEQ ID NO. 56
AATGTATCTAAACGCAAACTCCGAGCTGGAAA
AATGTTACCGGCGATGCGCGGACAATTTAGAG
GCGGCGATCAAGAAACACCTGCTGGGCGAGCA
GTCTGGAGCACAGTCTTCGATGGGCCCGAGAT
CCCACCGCGTTCCTGGGTACCGGGACGTGAGG
CAGCGCGACATCCATCAAATATACCAGGCGCC
AACCGAGTCTCTCGGAAAACAGCTTCTGGATA
TCTTCCGCTGGCGGCGCAACGACGAATAATAG
TCCCTGGAGGTGACGGAATATATATGTGTGGA
GGGTAAATCTGACAGGGTGTAGCAAAGGTAAT
ATTTTCCTAAAACATGCAATCGGCTGCCCCGC
AACGGGAAAAAGAATGACTTTGGCACTCTTCA
CCAGAGTGGGGTGTCCCGCTCGTGTGTGCAAA
TAGGCTCCCACTGGTCACCCCGGATTTTGCAG
AAAAACAGCAAGTTCCGGGGTGTCTCACTGGT
GTCCGCCAATAAGAGGAGCCGGCAGGCACGGA
GTCTACATCAAGCTGTCTCCGATACACTCGAC
TACCATCCGGGTCTCTCAGAGAGGGGAATGGC
ACTATAAATACTGCCTACTTGTCCTCTATTCC
TTCATCAATCACATC Variants of the FMD promoter consisting of or comprising SEQ ID NO: 1 showing a reduced expression rate under derepression comprise or consist of the following sequences:

(v23):
SEQ ID NO. 57
AATGTATCTAAACGCAAACTCCGAGCTGGAAA
AATGTTACCGGCGATGCGCGGACAATTTAGAG
GCGGCGATCAAGAAACACCTGCTGGGCGAGCA
GTCTGGAGCACAGTCTTCGATGGGCCCGAGAT
CCCACCGCGTTCCTGGGTACCGGGACGTGAGG
CAGCGCGACATCCATCAAATATACCAGGCGCC
AACCGAGTCTCTCGGAAAACAGCTTCTGGATA
TCTTCCGCTGGCGGCGCAACGACGAATAATAG
TCCCTGGAGGTGACGGAATATATATGTGTGGA
GGGTAAATCTGACAGGGTGTAGCAAAGGTAAT
ATTTTCCTAAAACATGCAATCGGCTGCCCCGC
AACGGGAAAAAGAATGACTTTGGCACTCTTCA
CCAGAGTGGGGTGTCCCGCTCGTGTGTGCAAA
TAGGCTCCCACTGGTCACCCCGGATTTTGCAG
AAAAACAGCAAGTTCCGGGGTGTCTCACTGGT

-continued

GTCCGCCAATAAGAGGAGCCGGCAGGCACGGA
GTCTACATCAAGCTGTCTCCGATACACTCGAC
TACCATCCGGGTCTCTCAGAGAGGGGAATGGC
ACCGATAGGGCAGAAATATATAAAGTAGGAGG
TTGTATACCAAATATACCAACGCAGTACAAGC
AACTCTTGGTTTAAACGGAAGAAACAATTCTT
CGAACATTTACAACAAAGAAGGTACCGTAACA
TTAATAATCGGAAGGGT (v24):
SEQ ID NO. 58
AATGTATCTAAACGCAAACTCCGAGCTGGAAA
AATGTTACCGGCGATGCGCGGACAATTTAGAG
GCGGCGATCAAGAAACACCTGCTGGGCGAGCA
GTCTGGAGCACAGTCTTCGATGGGCCCGAGAT
CCCACCGCGTTCCTGGGTACCGGGACGTGAGG
CAGCGCGACATCCATCAAATATACCAGGCGCC
AACCGAGTCTCTCGGAAAACAGCTTCTGGATA
TCTTCCGCTGGCGGCGCAACGACGAATAATAG
TCCCTGGAGGTGACGGAATATATATGTGTGGA
GGGTAAATCTGACAGGGTGTAGCAAAGGTAAT
ATTTTCCTAAAACATGCAATCGGCTGCCCCGC
AACGGGAAAAAGAATGACTTTGGCACTCTTCA
CCAGAGTGGGGTGTCCCGCTCGTGTGTGCAAA
TAGGCTCCCACTGGTCACCCCGGATTTTGCAG
AAAAACAGCAAGTTCCGGGGTGTCTCACTGGT
GTCCGCCAATAAGAGGAGCCGGCAGGCACGGA
GTCTACATCAAGCTGTCTCCGATACACTCGAC
TACCATCCGGGTCTCTCAGAGAGGGGAATGGC
ACGTAATCTTTCGGTCAATTGTGATCTCTCTT
GTAGATATTTAATAGGACGGCCAAGGTAGAAA
AAGATACATAACTAGTTAGCAAACTTCAATTG
CTTAAGTTACAAGTGCAATCCATATCTTAAAG
TTATTACATTATTTATA (v25):
SEQ ID NO. 59
AATGTATCTAAACGCAAACTCCGAGCTGGAAA
AATGTTACCGGCGATGCGCGGACAATTTAGAG
GCGGCGATCAAGAAACACCTGCTGGGCGAGCA
GTCTGGAGCACAGTCTTCGATGGGCCCGAGAT
CCCACCGCGTTCCTGGGTACCGGGACGTGAGG
CAGCGCGACATCCATCAAATATACCAGGCGCC
AACCGAGTCTCTCGGAAAACAGCTTCTGGATA
TCTTCCGCTGGCGGCGCAACGACGAATAATAG

-continued

```
TCCCTGGAGGTGACGGAATATATATGTGTGGA

GGGTAAATCTGACAGGGTGTAGCAAAGGTAAT

ATTTTCCTAAAACATGCAATCGGCTGCCCCGC

AACGGGAAAAAGAATGACTTTGGCACTCTTCA

CCAGAGTGGGGTGTCCCGCTCGTGTGTGCAAA

TAGGCTCCCACTGGTCACCCCGGATTTTGCAG

AAAAACAGCAAGTTCCGGGGTGTCTCACTGGT

GTCCGCCAATAAGAGGAGCCGGCAGGCACGGA

GTCTACATCAAGCTGTCTCCGATACACTCGAC

TACCATCCGGGTCTCTCAGAGAGGGGAATGGC

ACCCTCCTCTAGGTTTATCTATAAAAGCTGAA

GTCGTTAGAATTTTTCATTTAAAGCATAATCA

AACATCTAGATTCGAATCGATAAAAAGCAGAT

AGAAGTTATTAAGATTATAGGTTACATTCTAG

AGTAGTATAGGAAGGTA
```

According to a further preferred embodiment of the present invention the variant of SEQ ID NO:1 is selected from the group consisting of SEQ ID NO: 35, SEQ ID NO: 37, SEQ ID NO: 39, SEQ ID NO: 40, SEQ ID NO: 44, SEQ ID NO: 51, SEQ ID NO: 52, SEQ ID NO: 54, SEQ ID NO: 55 and SEQ ID NO: 56.

Another aspect of the present invention relates to a method for producing a heterologous polypeptide, comprising the step of culturing a yeast cell according to the present invention.

The yeast cell according to the invention, comprising an orthologous FMD and/or MOX promoter, is suitable in particular for overexpression of homologous or heterologous polypeptides. Because of the excellent properties, it is possible with the yeast cell according to the invention to express a polypeptide and/or protein under derepressing conditions as well as under methanol-induced conditions or suitable alternative inducing conditions and optionally to secrete it from the cell.

According to a preferred embodiment of the present invention, during cultivation, the expression of the heterologous polypeptide is induced under derepressing conditions or its expression rate is increased.

Promoter derepression can be achieved by a reduced feeding rate with a repressing carbon source (C source: e.g., glucose, glycerol) or by using a non-repressing C source (e.g., sorbitol). The repressing C source can achieve its properties through direct repression or through repressing properties of metabolites of the C source. The feed rate with repressing C sources can approach zero in the extreme case. Additional induction effects due to other compounds such as fatty acids, formaldehyde or formic acid are also possible.

To increase protein yield during cultivation and/or during its expression, methanol is preferably added during the culturing under derepressing conditions.

Those skilled in the art are sufficiently familiar with the general cultivation conditions, such as temperature, medium, etc. (see for example, Krainer F W et al. Microbial Cell Factories 11 (2012):22).

The present invention will be defined in greater detail on the basis of the following figures and examples but without being limited to them.

FIG. 1 shows the fluorescence intensities of a green fluorescent reporter protein (an improved variant of the green fluorescent protein (GFP)) in culturing yeast cells of the *Komagataella* genus in which a nucleic acid coding for the green fluorescent protein is operbly linked to orthologous and endogenous promoters. The orthologous promoters (and endogenous promoters from *P. pastoris* as reference) were operably linked to the GFP reporter gene and transformed as vectors in *P. pastoris*. The strains were cultured for 60 hours on minimal medium (BMD1) in microtiter plates with 96 deep wells (deep well plate (DWP)) and then induced with methanol. The fluorescence of the reporter protein and OD 600 (as a measure of biomass) was measured under glucose-repressed conditions (16 h), derepressed conditions (60 h) and measured at various points in time after methanol induction. The fluorescence measurements were normalized with respect to the OD 600 values. Averages and standard deviations of four transformants each are shown in the figure.

Figure 2A:
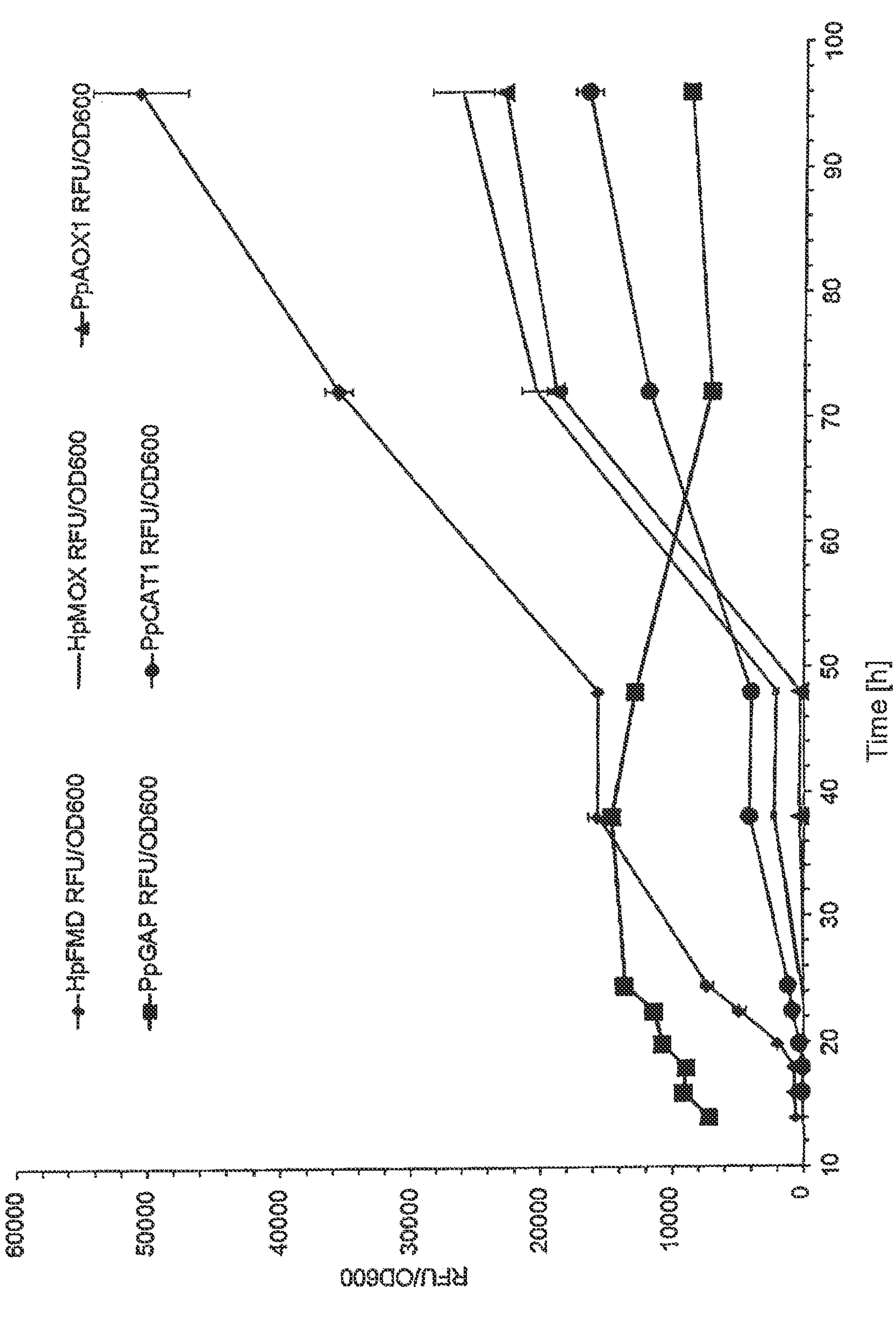
Figure 2B:
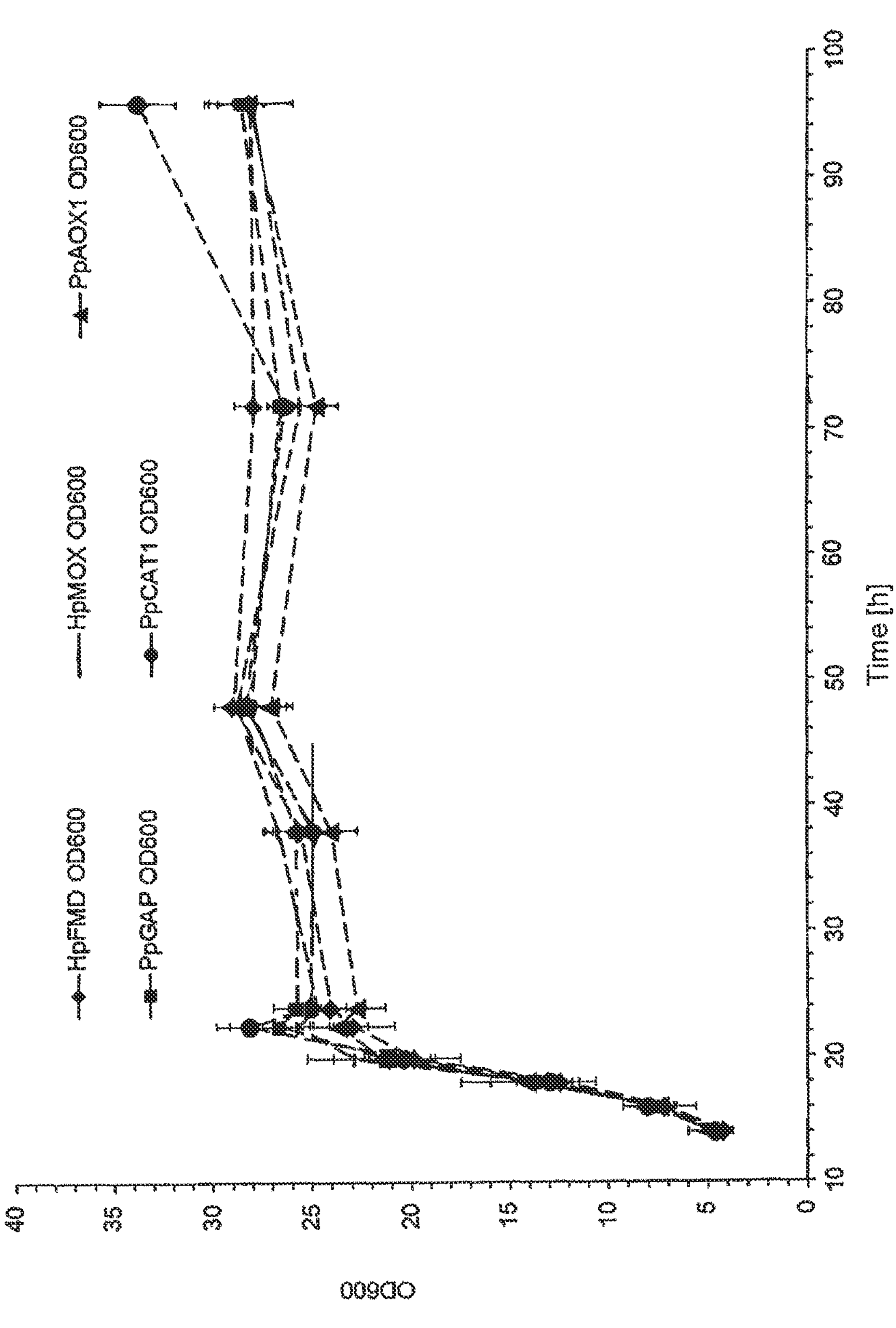
Figure 2C:
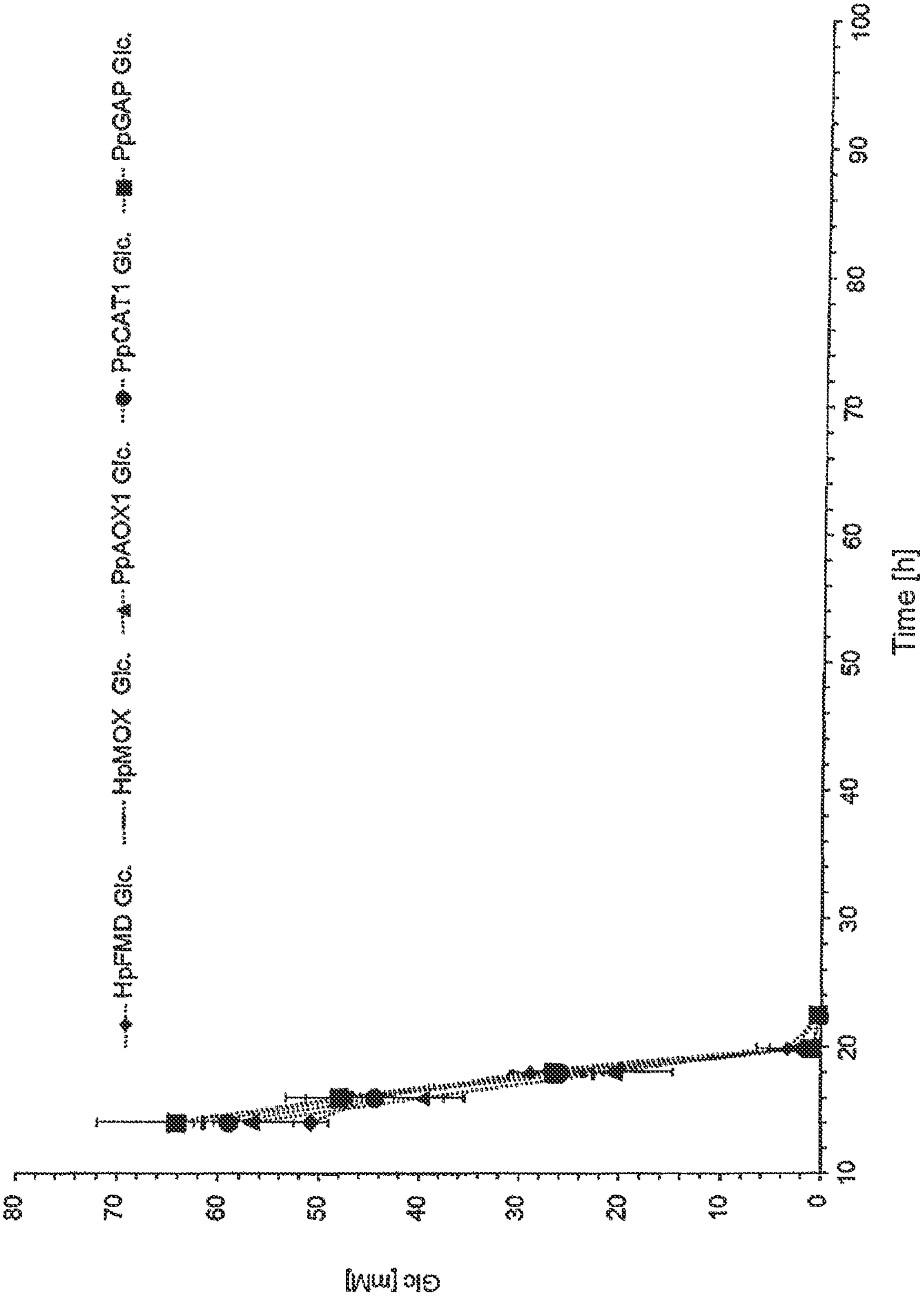

FIG. 2 shows the curve of measurements of protein expression over time. Selected strains from FIG. 1 were cultured in shaking flasks. The protein fluorescence (FIG. 2A; ratio RFU/=D600; RFU=relative fluorescence unit), while the OD600 (FIG. 2B) and the amount of glucose (FIG. 2C) were measured over time. The glucose concentration at the start of the measurements was 55.5 mM (10 g/L). The averages (MV) and standard deviations of three transformants each are shown.

Figure 3:
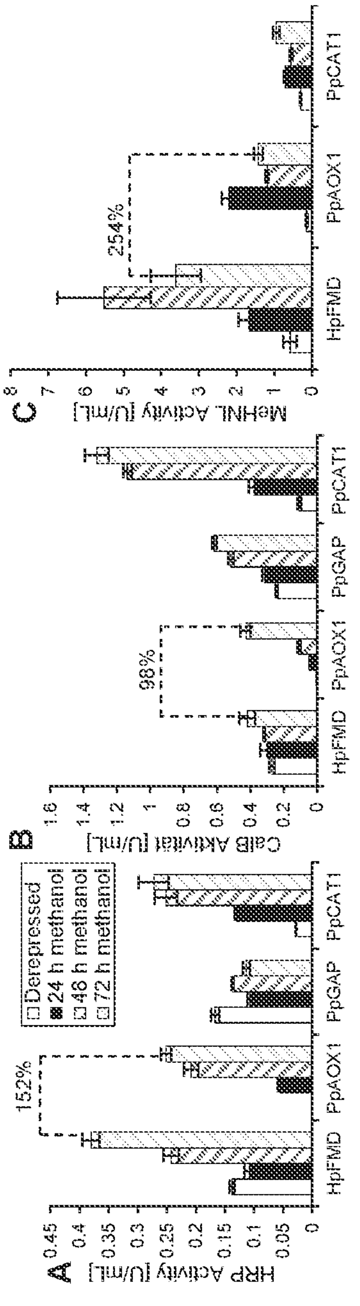

FIGS. 3A to 3C show that the orthologous HpFMD promoter is also capable of upregulating the expression of other reporter proteins such as horseradish per oxidase (HRP) (FIG. 3A), lipase B from *Candida antarctica* (CalB) (FIG. 3B) and a hydroxynitrile lyase from *Manihot esculenta* (MeHNL) (FIG. 3C). The strains were cultured in DWPs in minimal medium to the point of glucose depletion after 60 hand then additionally induced with methanol. HRP and CalB enzyme activities were measured in the culture supernatant. The activity of MeHNL was measured using digested cells. Averages and standard deviations of four transformants each are shown.

Figure 4:
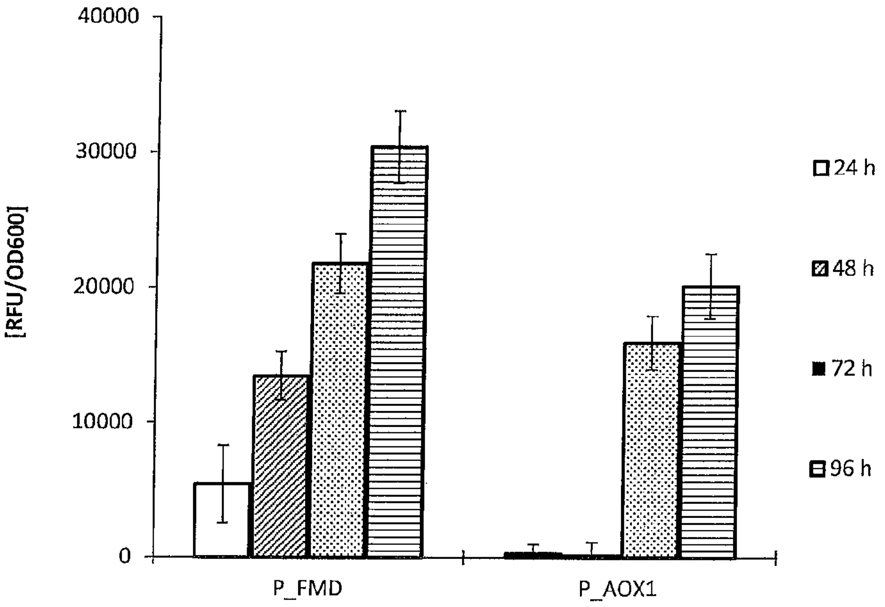

FIG. 4 shows reporter protein fluorescence of the HpFMD promoter (P_FMD) and the AOX1 promoter (P_AOX1) wild type sequence promoters tested. The strain background is the *P. pastoris* BglI KU70. Cultivation was done in deep well plate (DWP). Reporter protein fluorescence and OD600 were measured under glucose derepressed (24 and 48 h) and two different time points of methanol induction (72 and 96 h). The strain harboring the FMD promoter was used as reference strains for testing various promoter variants.

EXAMPLES

Example 1

Materials and Methods

Cloning the Promoters

The orthologous promoters were amplified by means of PCR and cloned before a GFP reporter gene. To do so, the reporter plasmid pPpT4mutZeoMlyI-intARG4-eGFP-Bmristuffer (T. Vogl et al. ACS Synth Biol. 2015, DOI: 10.1021/acssynbio.5b00199; published on 22 Nov. 2015).

This plasmid is based on the pPpT4 vector, which was described by L. Naatsaari et al. (PLoS One 7 (2012): e39720). The promoters were cloned seamlessly (i.e., without any restriction enzyme cleavage sites or linker sequences between the promoter and the start codon) to obtain the natural context. Primers were designed on the basis of literature references (HpFMD promoters (H. Song et al. Biotechnol Lett 25 (2003):1999-2006; A. M. Ledeboer et al. Nucleic Acids Res 13 (1985):3063-3082), CbAOD1 promoter (H. Yurimoto et al. Biochim Biophys Acta 1493 (2000):56-63), CbFLD1 promoter (B. Lee et al. Microbiology 148 (2000): 2697-704), Pm MOD1 and MOD2 promoters (C. K. Raymond et al. Yeast 14 (1998):11-23; T. Nakagawa et al. J Biosci Bioeng 91 (2001):225-7; T. Nakagawa et al. Yeast 23 (2006):15-22). The primer sequences used are given in Table A:

TABLE A

Primers for amplification of the orthologous promoters

| Name | Sequence | SEQ ID No. |
|---|---|---|
| HpFMDfwd | AATGTATCTAAACG CAAACTCCGAGCTG | 3 |
| HpFMDrev | GATTTGATTGATGA AGGCAGAGAGCGCA AG | 4 |
| HpMOXfwd | TCGACGCGGAGAAC GATCTCCTCGAGCT | 5 |
| HpMOXrev | TTTGTTTTTGTACT TTAGATTGATGTCA CCACCGTGCACTGG CAG | 6 |
| PmMOD1fwd | CGAGATGGTACATA CTTAAAAGCTGCCA TATTGAG | 7 |
| PmMOD1rev | TTTGAGAAATTAAT AGTAAGATTTTTTT TTCGTAAAAGTTTT GATTGAGTTAATTC | 8 |
| PmMOD2fwd | GGATCCACTACAGT TTACCAATTGATTA CGCCAATAG | 9 |
| PmMOD2rev | TTTGAATTTTAGTT TTAGATAGATAAAT ATAATTTTCAATCC TGTTATAAAATAGT ATAT | 10 |
| CbAOD1fwd | GGAGTATACGTAAA TATATAATTATATA TAATCATATATATG AATACAATGAAAG | 11 |
| CbAOD1rev | TATTGAAAAAATAAT TTTGTTTTTTTTTT TTTGTTTTTTTAAA AGTTCGTTAAAATT CG | 12 |
| CbFLD1fwd | GGATCCCTTCAACA GCGGAGTCTCAAAC | 13 |
| CbFLD1rev | TTTTGTGGAATAAA AAATAGATAAATAT GATTTAGTGTAGTT GATTCAATCAATTG AC | 14 |

Genomic DNA of the strains Hp (*Hansenula polymorpha*) DSM 70277, Cb (*Candida boidinii*) DSM 70026 and Pm (*Pichia methanolica*) DSM 2147 were isolated and used as templates for the PCR reactions. The PCR products were cloned by TA cloning in the vector pPpT4mutzeoMlyI-intARG4-eGFP-Bmristuffer (see also US 2015/0011407 and T. Vogl et al. (ACS Synth Biol. 2015, DOI: 10.1021/acssynbio.5b00199; published on 22 Nov. 2015)) The control vectors for the *P. pastoris* endogenous promoters AOX1, CAT1 and GAP are taken from US 2015/0011407.

The alternative reporter vectors, containing HRP (isoenzyme A2A; L. Naatsaari et al. BMC Genomics 15 (2014): 227), CalB and MeHNL downstream from the corresponding promoters, were taken from US 2015/0011407 or created by installing the eGFP reporter gene that had been cut from the above-mentioned eGFP vectors (restriction enzymes NheI and NotI) and the PCR products of HRP, CalB and MeHNL were installed seamlessly by recombinant cloning. The primers indicated in Table B were used for the PCR amplifications.

TABLE B

Primers for cloning promoters upstream from various reporter genes

| Primer | Sequence | SEQ ID No. |
|---|---|---|
| pHpFMD-MFalpha-Gib | cttgcgctctctgc cttcatcaatcaaa tcatgagattccca tctattttcaccgc tgtc | 15 |
| AOX1TT-NotI-CalB | caaatggcattctg acatcctcttgagc ggccgcttatgggg gcacgataccggaa caag | 16 |
| AOX1TT-NotI-HRPA2A | caaatggcattctg acatcctcttgagc ggccgcttaggatc cgttaactttcttg caatcaagtc | 17 |
| seq-pHpHMD-149..126fwd | actggtgtccgcca ataagaggag | 18 |
| pHpFMD-MeHNL | cttgcgctctctgc cttcatcaatcaaa tcatg gttactgctcacttc gtcttgattcac | 19 |
| AOX1TT-NotI-MeHNL | caaatggcattctga catcctcttgagcgg ccgcttaagcgtaag cgtcggcaacttcct g | 20 |
| pCAT1-MeHNL-Gib | cacttgctctagtca agacttacaattaaa atggttactgctcac ttcgtcttgattcac | 21 |

The HRP and CalB vectors mentioned in the literature where therefore used as PCR templates (US 2015/0011407 and T. Vogl et al. (ACS Synth Biol. 2015, DOI:10.1021/acssynbio.5b00199; published on 22 Nov. 2015). The MeHNL sequence was optimized for the *P. pastoris* codon and designed as a synthetic double-stranded DNA fragment with overhangs to the AOX1 promoter and terminator (see Table B). This fragment was used as a template for PCRs. The following sequence was used:

(SEQ ID No. 22)

cgacaacttgagaagatcaaaaaacaactaattattgaaagaattcc gaaacgATGGTTACTGCTCACTTCGTCTTGATTCACACTATCTGTCA

TGGTGCTTGGATCTGGCACAAGTTGAAGCCAGCATTGGAGAGAGCTG

GACATAAGGTTACCGCTCTTGATATGGCTGCATCTGGTATTGATCCT

CGTCAAATCGAACAAATCAATTCATTCGACGAGTACTCAGAGCCACT

GCTGACCTTCTTGGAAAAGTTGCCTCAAGGTGAAAAGGTGATCATCG

TTGGTGAATCCTGTGCTGGATTGAACATTGCCATTGCAGCTGATAGA

TATGTCGATAAGATCGCTGCTGGTGTCTTCCACAACTCTCTGTTACC

AGATACTGTTCACTCTCCATCTTACACTGTCGAGAAGTTGTTAGAAT

CATTCCCAGATTGGAGAGATACTGAATACTTTACTTTCACTAACATC

ACTGGAGAGACTATCACCACCATGAAACTTGGATTCGTTTTGTTGAG

AGAAAACCTTTTCACCAAGTGTACTGATGGTGAATACGAATTGGCCA

AGATGGTTATGAGAAAGGGTTCTTTGTTTCAGAATGTTCTTGCACAA

AGACCAAAGTTCACCGAAAAGGGTTACGGTTCTATCAAGAAGGTCTA

CATCTGGACTGATCAGGACAAGATCTTCCTGCCAGACTTCCAAAGAT

GGCAAATCGCAAACTACAAACCAGATAAGGTCTACCAAGTCCAAGGT

GGTGATCACAAGTTACAATTGACCAAGACCGAAGAGGTCGCTCACAT

CTTGCAGGAAGTTGCCGACGCTTACGCTTAAgcggccgctcaagagg atgtcagaatgccatttgcctg

The protein coding sequence here is large and the start and stop codon is shown in bold font, while overhangs to the vector for recombinant cloning are written in lower case letters, EcoRI and NotI, which are cleavage sites typically used for cloning in the pPpT4 vector family, are underlined.

The same forward primer (pHpFMD-MFalpha-Gib) was also used for PCR amplification of the HRP and CalB genes because the two genes are fused to an MFalpha signal sequence. Genes cloned in the vectors were sequenced by using primers that bind to the AOX1 terminator and the respective promoters (seq-pHpHMD149 . . . 126fwd for the HpFMD promoter).

Strains, Materials, Fluorescence Measurements and Enzyme Assays

Enzymatic HRP and CalB activity were determined with the substrates 2,2'-azino-bis(3-ethylbenzothiazoline-6-sulfonic acid)diammonium salt (ABTS) and p-nitrophenyl butyrate (p-NPB) according to protocols in Krainer F W (Microb Cell Fact 11 (2012):22).

For the transformations of all promoter comparisons with GFP, the CBS7435 wild type strain was used. HRP and CalB plasmids were transformed into the mutS strain (L. Naatsaari et al. (PLoS One (2012); 7:e39720) because it has a higher protein expression (F. W. Krainer et al. Microb Cell Fact 11 (2012):22). For MeHNL activity measurements, the cells were lysed by Y-PER digestion according to the manufacturer's instructions (Thermo Fisher Scientific, Y-PER™ Yeast Protein Extraction Reagent) and the activity was measured using a "mandelonitrile cyanogenase assay," as described by R. Wiedner et al. Comput Struct Biotechnol J10 (2014):58-62) (final mandelonitrile concentration 1SmM).

Results

Six heterologous promoters of HpFMD, HpMOX, CbFLD1, CbAOD1, PmMOD1 and PmMOD2 genes were tested in *P. pastoris*. The promoters were compared with the methanol-inducible AOX1 promoter, the constitutional GAP promoter and the derepressed/methanol-inducible CAT1 promoter in *P. pastoris*, namely the orthologous promoters were amplified by genomic DNA PCR and cloned in vectors with GFP as reporter gene. The following promoter sequences were used:

HpFMD:

(SEQ ID No. 1)

AATGTATCTAAACGCAAACTCCGAGCTGGAAA

AATGTTACCGGCGATGCGCGGACAATTTAGAG

GCGGCGATCAAGAAACACCTGCTGGGCGAGCA

GTCTGGAGCACAGTCTTCGATGGGCCCGAGAT

CCCACCGCGTTCCTGGGTACCGGGACGTGAGG

CAGCGCGACATCCATCAAATATACCAGGCGCC

AACCGAGTCTCTCGGAAAACAGCTTCTGGATA

TCTTCCGCTGGCGGCGCAACGACGAATAATAG

TCCCTGGAGGTGACGGAATATATATGTGTGGA

GGGTAAATCTGACAGGGTGTAGCAAAGGTAAT

ATTTTCCTAAAACATGCAATCGGCTGCCCCGC

AACGGGAAAAAGAATGACTTTGGCACTCTTCA

CCAGAGTGGGGTGTCCCGCTCGTGTGTGCAAA

TAGGCTCCCACTGGTCACCCCGGATTTTGCAG

AAAAACAGCAAGTTCCGGGGTGTCTCACTGGT

GTCCGCCAATAAGAGGAGCCGGCAGGCACGGA

GTCTACATCAAGCTGTCTCCGATACACTCGAC

TACCATCCGGGTCTCTCAGAGAGGGGAATGGC

ACTATAAATACCGCCTCCTTGCGCTCTCTGCC

TTCATCAATCAAATC

HpMOX:

(SEQ ID No. 2)

CGACGCGGAGAACGATCTCCTCGAGCTGCTCG

CGGATCAGCTTGTGGCCCGGTAATGGAACCAG

GCCGACGGCACGCTCCTTGCGGACCACGGTGG

CTGGCGAGCCCAGTTTGTGAACGAGGTCGTTT

AGAACGTCCTGCGCAAAGTCCAGTGTCAGATG

AATGTCCTCCTCGGACCAATTCAGCATGTTCT

CGAGCAGCCATCTGTCTTTGGAGTAGAAGCGT

AATCTCTGCTCCTCGTTACTGTACCGGAAGAG

GTAGTTTGCCTCGCCGCCCATAATGAACAGGT

TCTCTTTCTGGTGGCCTGTGAGCAGCGGGGAC

GTCTGGACGGCGTCGATGAGGCCCTTGAGGCG

CTCGTAGTACTTGTTCGCGTCGCTGTAGCCGG

CCGCGGTGACGATACCCACATAGAGGTCCTTG

GCCATTAGTTTGATGAGGTGGGGCAGGATGGG

-continued

CGACTCGGCATCGAAATTTTTGCCGTCGTCGT

ACAGTGTGATGTCACCATCGAATGTAATGAGC

TGCAGCTTGCGATCTCGGATGGTTTTGGAATG

GAAGAACCGCGACATCTCCAACAGCTGGGCCG

TGTTGAGAATGAGCCGGACGTCGTTGAACGAG

GGGGCCACAAGCCGGCGTTTGCTGATGGCGCG

GCGCTCGTCCTCGATGTAGAAGGCCTTTTCCA

GAGGCAGTCTCGTGAAGAAGCTGCCAACGCTC

GGAACCAGCTGCACGAGCCGAGACAATTCGGG

GGTGCCGGCTTTGGTCATTTCAATGTTGTCGT

CGATGAGGAGTTCGAGGTCGTGGAAGATTTCC

GCGTAGCGGCGTTTTGCCTCAGAGTTTACCAT

GAGGTCGTCCACTGCAGAGATGCCGTTGCTCT

TCACCGCGTACAGGACGAACGGCGTGGCCAGC

AGGCCCTTGATCCATTCTATGAGGCCATCTCG

ACGGTGTTCCTTGAGTGCGTACTCCACTCTGT

AGCGACTGGACATCTCGAGACTGGGCTTGCTG

TGCTGGATGCACCAATTAATTGTTGCCGCATG

CATCCTTGCACCGCAAGTTTTTAAAACCCACT

CGCTTTAGCCGTCGCGTAAAACTTGTGAATCT

GGCAACTGAGGGGGTTCTGCAGCCGCAACCGA

ACTTTTCGCTTCGAGGACGCAGCTGGATGGTG

TCATGTGAGGCTCTGTTTGCTGGCGTAGCCTA

CAACGTGACCTTGCCTAACCGGACGGCGCTAC

CCACTGCTGTCTGTGCCTGCTACCAGAAAATC

ACCAGAGCAGCAGAGGGCCGATGTGGCAACTG

GTGGGGTGTCGGACAGGCTGTTTCTCCACAGT

GCAAATGCGGGTGAACCGGCCAGAAAGTAAAT

TCTTATGCTACCGTGCAGTGACTCCGACATCC

CCAGTTTTTGCCCTACTTGATCACAGATGGGG

TCAGCGCTGCCGCTAAGTGTACCCAACCGTCC

CCACACGGTCCATCTATAAATACTGCTGCCAG

TGCACGGTGGTGACATCAATCTAAAGTACAAA

AACAAA

CbFLD1:

(SEQ ID No. 23)

GGATCCCTTCAACAGCGGAGTCTCAAGCAGTG

GCTATTATCAGTGTATTTAATTACTGATGCAT

TGTATTATAGTGCATACATAGTTAATAATTAC

TCTCTGTTATCATTGAAAATTTTGAAATTCTC

ACTCTCACGCAGTGCAAAACTTTGCCTAATTG

-continued

AGTAAGTGGAACGCAATATTTAGGCTACATAT

TTTGGATTCCCTTAAGTATGTAATCAAAGATC

ATTCATACTGCCATCTTATAATATTGGAGTAT

TATTATGTTGCTATACTGTTCTACCTGTTTAT

TCTATTGTATGCGTCTAAATCTTTCCATCAGT

TTCTATACTATCTTTCGTTTGCAATGAAATAT

TACTCCAATTCGCTTGTTTCAACTCGCTTGCC

TTCTCTCTTGCCTTCTTTTTTTCTTTTCATTT

TATCGTTGTTTAAACGGTATATAAATATGTAA

CGTTGTCGCTTAGTTTTGAGAAATCACTTTTG

TTGCTCTCAATTCTGTTTTGACATCTTAAGGT

TAGTCAATTGATTGAATCAACTACACTAAATC

ATATTTATCTATTTTTTATTCCACAAAA

CbAOD1:

(SEQ ID No. 24)

GGAGTATACGTAAATATATAATTATATATAAT

CATATATATGAATACAATGCAATGAAAGTGAA

TATGATAAGATTGAAATAATAACAAACAGCGA

TAAATATATCTCAAAATGGAGTTACACAACAA

ATAATAATAAAATATAAATTATAAATTATAAA

TTATAAAAGAATAAAAAATAAACCCCACTAAT

TTATTTTATTAAAAGATAGATTGGTATCTTTA

CTTAATAACAATTCTGAAACTTTATTCACTTA

ATTTTATTTAACTTATTTAATTTATTTTTACC

CCAGTTTTTCAGTACAATGCAGCTCCGAAACT

TTATTTGGCTGTGATTTGGCTGTGATTTGGCT

GTGATTTGGCTTGGCTTGGCTGGCTGGAATTG

TCTCCTGCAGGAATTGCTCGGGGTCCGGTTCT

CCCGCTGGCTGGCTATTTGGCGGGCTGGCTAT

TTGGCGGGCTGGCTGGCTGGCTGCTCTGCCAT

CTGCTGTGGCCACCCCGCATCTCTGGATGCAC

GCCGTGCAGCTGGACGTGCGTCTACCCTGCAG

CCGTGTGCCTTATTTCCCAATCTCCCAATCTC

TCAATCTGCCAGTCAGCCAAAACACCGGCCAG

GCAGGCAGGCAGGCAGGCAGGCAGGCAGTGAA

GCCTTCCCACGCCCCACTCCGCATAAACATCC

CCAGCAGTTTCCCCAGCAGTTTCCCCAGCTTT

TCAATTTAATAAAATAGCCTGTTTCTGTTTCT

GTTTTATATTATACAATTTTTTATCCTAATAA

TTACTCTTTCGGGAATTAAATAATAATTATAT

CATATACCCATATCACATTTTACTATATTTAC

TATCTATAAATAAATTCATATTATAATATTAA

-continued

TTTATATTCGCTTAATTAAAATGCTCTTTTCC
ATCATCATCATCATCATCATCATCACGAGTTT
TCGGTTATCAATACTCTTTTCATTAATTTCTA
GAATTTCATTATTTATTTTTTATTGACTGGAA
ATTTTCAATCAATTTTATTTATTTTTATTTAT
TTATTTTCATATTCTTAGATTTAAACTTTTTA
GATGACCGCTATTTTACTTACTTACTTACTGT
TGTTTTATATTATGATAAGAATTAATTTTCAT
ATTTATGATGATGATGATGTAAATTTAACCTA
GTATACTATTTTAAAGTTATCACTATCTTTTA
GTGCTGGCATTTTTTATTCTATTTTCATATAT
GTATATACGTAAATTAAGTATCATCACGCTGC
TTACTGTACGTTTAAAATGTGGAGATGGAAAT
AGAGATGGGGATGAAGATGAAGATGATGAGAA
TTATAAACCATTCATTCATTAATCAATCAATA
TAACTTATAAAAAAATTTATATTTAAATGAAT
TAATTTCCTTTATTTTAATAATATCGTTAATT
CTTTTAAATTCTATTTTATTTTAATTCTTTCT
TTATCATAGTTATCATATAACAATTATATAAC
ATAGATACACAATTATTATTTCATTATCATAT
TATTTTTTAAAATATTGATTATTTTTAAAATA
ATATCTTAATTAATTAATTTTTACGAATATAC
AAATTTTAACGACTTACTTTTTTTAACGAATT
TTAACGAACTTTTAAAAAAACAAAAAAAAAAA
AACAAAATTATTTTTCAATA

PmMOD1:
(SEQ ID No. 25)

CGAGATGGTACATACTTAAAAGCTGCCATATT
GAGGAACTTCAAAGTTTTATCTGTTTTTAGAA
TTAAAAGACGATTGTTGTAACAAAACGTTGTG
CCTACATAAACTCAAATTAATGGAAATAGCCT
GTTTTGAAAAATACACCTTCTTAAGTACTGAC
AAAGTTTTGTTAAATGACTATCGAACAAGCCA
TGAAATAGCACATTTCTGCCAGTCACTTTTAA
CACTTTCCTGCTTGCTGGTTGACTCTCCTCAT
ACAAACACCCAAAAGGGAAACTTTCAGTGTGG
GGACACTTGACATCTCACATGCACCCCAGATT
AATTTCCCCAGACGATGCGGAGACAAGACAAA
ACAACCCTTTGTCCTGCTCTTTTCTTTCTCAC
ACCGCGTGGGTGTGTGCGCAGGCAGGCAGGCA
GGCAGCGGGCTGCCTGCCATCTCTAATCGCTG

-continued

CTCCTCCCCCCTGGCTTCAAATAACAGCCTGC
TGCTATCTGTGACCAGATTGGGACACCCCCCT
CCCCTCCGAATGATCCATCACCTTTTGTCGTA
CTCCGACAATGATCCTTCCCTGTCATCTTCTG
GCAATCAGCTCCTTCAATAATTAAATCAAATA
AGCATAAATAGTAAAATCGCATACAAACGTCA
TGAAAAGTTTTATCTCTATGGCCAACGGATAG
TCTATCTGCTTAATTCCATCCACTTTGGGAAC
CGTTCTCTCTTTACCCCAGATTCTCAAAGCTA
ATATCTGCCCCTTGTCTATTGTCCTTTCTCCG
TGTACAAGCGGAGCTTTTGCCTCCCATCCTCT
TGCTTTGTTTCGGTTATTTTTTTTTCTTTTGA
AACTCTTGGTCAAATCAAATCAAACAAAACCA
AACCTTCTATTCCATCAGATCAACCTTGTTCA
ACATTCTATAAATCGATATAAATATAACCTTA
TCCCTCCCTTGTTTTTTACCAATTAATCAATC
TTCAAATTTCAAATATTTTCTACTTGCTTTAT
TACTCAGTATTAACATTTGTTTAAACCAACTA
TAACTTTTAACTGGCTTTAGAAGTTTTATTTA
ACATCAGTTTCAATTTACATCTTTATTTATTA
ACGAAATCTTTACGAATTAACTCAATCAAAAC
TTTTACGAAAAAAAAATCTTACTATTAATTTC
TCAAA

PmMOD2:
(SEQ ID No. 26)

GGATCCACTACAGTTTACCAATTGATTACGCC
AATGTGTTTATTTCACCAAGTAATTACAAAAC
TGAGATTTGGTTATGTCATTATGTATTTTCGG
CAATGGCTGTAATTTAAACTGGATTAGGGTTA
ATTAACGTTTAGCCTACGAAAGCGGCTAGCTT
TTATTTCTGCTTTTGTTTTGAGCCCGTTTCTA
ATTCCAATCTTTGCAATTTCGTTCCATCTTTT
AAAATTAAGTGCTCTTTTCTAATCTGATAAAG
ATAAGCCATCGTAGAGTAAGTAAAACAAAATA
ATGTACTGTATATTAAGCGGAAAAACTTGGAA
AAGTCGTATGATGTTGAAGGAGCAAAGAATGA
CTAATATTAGGAGATTTAAGCAAACAATGTTG
AGGGGAACAGGACGATTAACCCCTTATAGAGG
AAGCGTCTTTGATGTTCGAAGGGGGAGGGGTC
AAAAGCACTGAGCAGTGCTAATTAGTAACCAA
TTTCTGTAAGCAATGAAACTTGTTGCTATTGG
AAATACTATTAAGTAATACAAGGTACAGACTA

-continued

ATGGGGGTGAGCCGGTAGTTCAGGCTATCTTA

TAGACAGACTATTCCGGATTGTCTAATCATTG

GTGCACCTGGTTAATAATTATCAGTCAACTCT

TTTACGGTGCTGATAGGTCTTTGCGAACTTGC

CCTTGTGGAATTTGGTTGTTAATCAAACTGTT

CTGTATTTCATGTCATACTACTATTGATATTA

TTAATGTTACTTACTCATCTGGCCATTTAACA

GGTTTGAAGCTTTAATGCTCTTAACTAACAGC

AATCCATCACCGTCAACCTTAACCCCCCTGGT

GCTTGCTGTCTTTATCCTTCGTATCTTTTTCA

TGTTGCACCGCCCTGTTCCTTATACGGTTGTT

CCCCCATAGGCTAACTTCTCTGTTTCCGACCA

TCTCTGCAATAACAAAGAATTCTATACGCTTA

CACTATAATCATACAATGACTCTACATGCCAT

TTTCACTTTACTTACTTGCCATCGGAAGATAC

TGAATCAGAAAGCCATAGTAACTACATAACTT

CAAAACACACCCTTTTTACAGATTAGTTACAA

TTTTGTCAATGTTTGTTTGATAACCCAAGGTG

GAACGTTTCCAGTTAGACCTGTTTAATCCAAC

TCACTTTACCACCCCAAAACTTTCCTACCGTT

AGACAAATACTGGCTAAATCTGACGAAAACAA

CCAATCAACAATTGAATCCACTGGGAGGTATC

TCTAATCCACTGACAAACTTTGCTAAAACAAG

AAAAAGTGGGGGCCTCCGTTGCGGAGAAGACG

TGCGCAGGCTTAAAAACACAAGAGAACACTTG

GAAGTACCCCAGATTTTTAGCTTCCTACTATT

CTGACACCCCCTATTCAAGCACGACGGTGATT

GATTCATTCAATTTTGCTGCTCCAATGATAGG

ATAAACCCTTTTGGACTTCAATCAGACCTCTG

TCCTCCATAGCAATATAAATACCTTCTAGTTG

CCCCACTTCCTCTCTCCTGTACTGCCCCAATG

AGTGACTTATTCAAGTTACTTTCTCTCTTTTC

CTAACAATTAAACAAGAAGCTTTATTATAACA

TTAATATACTATTTTATAACAGGATTGAAATT

ATATTTATCTATCTAAAACTAAAATTCAAA

*P. pastoris* transformants containing plasmids with CbAOD1, PmMOD1 and PmMOD2 promoters did not have any reporter protein fluorescence (FIG. 1). The CbFLD1 promoter exhibited repression on glucose and weak induction by methanol by approximately 10% of the PpAOX1 promoter. Both tested *H. polymorpha* promoters surprisingly retained their natural regulation profile from *H. polymorpha* and also in *Pichia pastoris* repression, derepression and methanol induction (FIGS. 1 and 2). The HpFMD promoter surprisingly exceeded the constitutional PpGAP promoter under derepressed conditions and also achieved approximately 75% of the methanol-induced PpAOX1 promoter, even without feeding with additional carbon sources. The derepressed expression of the HpFMD promoter exceeded that of the reporter protein fluorescence of the strongest endogenous MUI promoter from *P. pastoris* (PpCAT1) by a factor of approximately 3.5. After methanol induction, the HpFMD promoter exceeded the PpAOX1 promoter by a factor of approximately 2. These results on a small scale (FIG. 1) have been confirmed by experiments in shaking flasks (FIG. 2), wherein glucose measurements also show clearly the derepressed regulation profile. A further increase in the technical advantages of the HpFMD promoter can be achieved by an optimized feeding rate in the bioreactor.

To investigate whether the unexpectedly strong expression of the HpFMD reporter can also be reproduced for other proteins in addition to GFP, the HpFMD promoter was cloned upstream from the coding sequences of other proteins: the secreted proteins horseradish peroxidase (HRP) and *Candida antarctica* lipase B (CalB) and the intracellular hydroxynitrile lyase from *Manihot esculenta* (cassava, MeHNL) (FIGS. 3A to 3C).

With respect to the final yields of active protein in the culture supernatant in the shaking flask experiment, the derepressed expression of all proteins by the HpFMD promoter was equal to the constitutional expression by the GAP promoter and clearly exceeded the derepressed expression by the CAT1 promoter. Methanol-induced enzyme activities of the HpFMD promoter exceeded the AOX1 promoter activity by a factor of 2.5.

The strong expression the HpFMD promoter could also be observed with four different secreted reporter proteins as well as intracellular reporter proteins (eGFP, HRP, CalB, MeHNL). The orthologous HpFMD promoter even exceeded endogenous promoters in *P. pastoris*.

The orthologous promoters interestingly have very low or no sequence identities with promoters in *Pichia*. A BLAST search of the HpFMD promoter did not yield any significant hits in the *Pichia pastoris* genome; a direct alignment of the HpFMD promoter with the PpFDH1 promoter also did not yield any significant similarities (BLASTN 2.2.32+, Blast 2 sequences, setting for "somewhat similar sequences (blastn)"; molecule type: nucleic acid).

Such low sequence identity is a desirable property of promoters because these foreign sequences cannot recombine with the identical sequences in the genome of *Pichia* and therefore cannot be lost, for example, due to homologous recombination events with similar sequences already present in the genome.

Orthologous promoters may surprisingly be highly useful tools for protein expression, as demonstrated by the higher activities by a factor of as much as 2.5 due to the HpFMD promoter. Unexpectedly, the HpFMD promoter also retained its derepressed regulation profile from *H. polymorpha* in *P. pastoris* and thus constitutes the strongest derepressed promoter in *P. pastoris*. Therefore, efficient production processes free of toxic and highly inflammatory methanol can be made possible.

Example 2: FMD Promoter Variants

1. Cloning of Promoters

The pPpT4mutZeoMlyI-intArg4-EGFP-P_FMD, containing the FMD promoter having SEQ ID NO: 1 served as template for PCR amplification of the promoter variants v01 to v22. Primers were designed in a way to introduce point mutations, insertions or different core promoters to the FMD promoter sequence. The promoter variants were amplified in two parts and then assembled with the backbone of the pPpT4mutZeoMlyI-intArg4-eGFP-P_FMD vector, which had been previously cut with the restriction endonuclease SalI. For the generation of the promoter variants v23 to v25 only one part was PCR amplified and the other part was ordered as synthethic DNA. In this case the two DNA fragments were assembled with the backbone of the pPpT4mutZeoMlyI-intArg4-eGFP-P_FMD vector, which had been previously cut with the restriction endonuclease NheI. For the assembly of the DNA fragments with the vector backbone assembly cloning based on sequence homology was used, resulting in a seamless transition from promoter to the reporter gene eGFP.

2. *P. pastoris* Transformations and Screening

For transformations of the vectors harboring the different promoter variants v01 to v25 into yeast the *P. pastoris* BglI KU70 strain was used. Compared to the wild type strain, this strain has two gene knock outs: First, the KU70 gene, which encodes for a protein involved in the non-homologous end joining machinery. By knocking out this gene, homologous recombination events are more likely to happen in *P. pastoris*. This facilitates targeting of the vectors into a defined locus, in this case the ARG4 locus to avoid unexpected effects by different integration loci in the genome. The second knocked out gene is the AOX1 gene (mutS/BglI strain). By using this knock out strain higher yields of heterologous expressed proteins under the control of a methanol inducible promoter can be achieved (Krainer F W et al. Microb. Cell Fact. 11(2012) p. 22).

*P. pastoris* BglI KU70 was transformed with BglII linearized plasmids according to the condensed protocol of Lin-Cereghino et al. (Biotechniques 38(2005):44-48). To have reference strains for the screening the same vector as for the promoter variants—but with the non modified FMD promoter of SEQ ID NR1 and the AOX1 promoter instead—were transformed as well. About 500 ng, which is relatively low amounts of DNA were transformed to avoid multi copy integrations. For example, using 1 μg of a linearized pPpT4_S vector typically only yields single copy transformants (Vogl T et al. ACS Synth. Biol. 3(2014):188-191).

For 9 constructs 42 transformants were screened to show the uniformity of the expression landscapes. Since the landscape for all of those tested constructs proved to be uniform, only 16 transformants per construct were picked and cultivated on two different deep well plates (DWP) in the second screening round. DWP cultivations were adapted from the protocol reported by Weis et al. (Weis R et al. FEMS Yeast Res. 5 (2004):179-89). Single colonies were picked and used to inoculate BMD (250 μl) into 96 well DWPs and cultivated for 48 h. Then BMM2 (250 μl) was added to induce the cells for the first the time. The cells were induced another 3 times with BMM10 (50 μl) after 60, 72 and 84 hours of cultivation in the DWP. Samples were taken and measured after 48, 72 and 96 hours. Samples were taken as followed: 10 μl cell culture was mixed with 190 μl of deionized water in micro titer plates (Nunc MicroWell 96-Well Optical-Bottom Plates with Polymer Base, Black; Thermo Fisher Scientific). eGFP fluorescence measurements were performed using a FLUOstar® Omega plate reader (BMG LABTECH GmbH, Ortenberg, Germany). Fluorescence was measured at 488/507 nm (excitation/emission) and for data evaluation the resulting relative fluorescence units (RFU) me were normalized to the OD600.

TABLE C

Primers and synthetic DNA for generation of FMD promoter variants

| Name | Sequence | SEQ ID No. |
|---|---|---|
| intARG.fwd | GCCAATTCTC AATTTGCTAG AGACTCTG | 60 |
| P_FMD-v01.fwd | Agaggcggcg Aatcaagaaa cacc | 61 |
| P_FMD-v01.rev | Ggtgtttctt gatTcgccgc ctct | 62 |
| P_FMD-v02.fwd | ctgccccgcG acgggaaaaa gaatg | 63 |
| P_FMD-v02.rev | Cattcttttt cccgtCgcgg ggcag | 64 |
| P_FMD-v03.fwd | Ggattttgca gaaaaaTagc aagttccggg | 65 |
| P_FMD-V03.rev | Cccggaactt gctAtttttc tgcaaaatcc | 66 |
| P_FMD-v04.fwd | Gtctctcaga gGggggaatg gc | 67 |
| P_FMD-v04.rev | Gccattcccc Cctctgagag ac | 68 |
| P_FMD-v05.fwd | Cactcgacta ccaGccgggt ctctc | 69 |
| P_FMD-v05.rev | Gagagacccg gCtggtagtc gagtg | 70 |
| P_FMD-06_fwd | CACTCGACTA CCATCCGGGT CTCTCCGAGA GGGGAATGGC ACTATAAATA C | 71 |
| P FMD-07 fwd | CACTCGACTA CCATCCGGGT CTCTCACAGA GGGGAATGGC ACTATAAATA C | 72 |
| P_FMD-08_fwd | CACTCGACTA CCATCCGGGT CTCTCAGCGA GGGGAATGGC ACTATAAATA C | 73 |
| P_FMD-09_fwd | CACTCGACTA CCATCCGGGT CTCTCAGACA GGGGAATGGC ACTATAAATA C | 74 |

TABLE C-continued

Primers and synthetic DNA for generation of FMD promoter variants

| Name | Sequence | SEQ ID No. |
|---|---|---|
| P_FMD-10_fwd | CACTCGACTACCATCCGGGTCTCTCAGAGCGGGGAATGGCACTATAAATAC | 75 |
| P_FMD-11_fwd | CACTCGACTACCATCCGGGTCTCTCAGAGACGGGAATGGCACTATAAATAC | 76 |
| P_FMD-12_fwd | CACTCGACTACCATCCGGGTCTCTCAGAGAGCGGAATGGCACTATAAATAC | 77 |
| P_FMD-13_fwd | CACTCGACTACCATCCGGGTCTCTCAGAGAGGCGAATGGCACTATAAATAC | 78 |
| P_FMD-14_fwd | CACTCGACTACCATCCGGGTCTCTCAGAGAGGGCAATGGCACTATAAATAC | 79 |
| P FMD-15 fwd | CACTCGACTACCATCCGGGTCTCTCAGAGAGGGGCATGGCACTATAAATAC | 80 |
| P_FMD-16_fwd | CACTCGACTACCATCCGGGTCTCTCAGAGAGGGGACTGGCACTATAAATAC | 81 |
| P_FMD-17_fwd | CACTCGACTACCATCCGGGTCTCTCAGAGAGGGGAACGGCACTATAAATAC | 82 |
| P_FMD-18_fwd | CACTCGACTACCATCCGGGTCTCTCAGAGAGGGGAATCGCACTATAAATAC | 83 |
| P_FMD-19_fwd | CACTCGACTACCATCCGGGTCTCTCAGAGAGGGGAATGCCACTATAAATAC | 84 |
| P_FMD_rev | GAGAGACCCGGATGGTAGTCG | 85 |
| P FMD-V20 fwd | ctcatactcaaactatattaaaactacaacaATGGCTAGCAAAGGAGAAGAACTTTTCAC | 86 |
| P FMD-V20 rev | tgttgtagttttaatatagtttgagtatgagatggaactcagaacgaaggaattatcaccagtttatatagtgccattcccctctctgag | 87 |
| P_FMD-v21_fwd | gactcacccataaacaaataatcaataaatATGGCTAGCAAAGGAGAAGAACTTTTCAC | 88 |
| P FMD-v21 rev | atttattgattatttgtttatgggtgagtctagaaaaggacgcactcgtcttgtatttatagtgccattccccTctctgag | 89 |
| P_FMD-v22_fwd | acttgtcctctattccttcatcaatcacatcATGGCTAGCAAAGGAGAAGAACTTTTCAC | 90 |
| P_FMD-v22_rev | gatgtgattgatgaaggaatagaggacaagtaggcagtatttatagtgccattccccTctctgag | 91 |
| Pcore_FMD_v23 (synthetic DNA) | atcaagctgtctccgatacactcgactaccatccgggtctctcagagAggggaatggcacCGATAGGGCAGAAATATATAAAGTAGGAGGTTGTATACCAAATATACCAACGCAGTACAAGCAACTCTTGGTTTAAACGGAAGAAACAATTCTTCGAACATTTACAACAAAGAAGGTACCGTAACATTAATAATCGGAAG | 92 |

TABLE C-continued

| Primers and synthetic DNA for generation of FMD promoter variants | | |
|---|---|---|
| Name | Sequence | SEQ ID No. |
| | GGTATGGCTA GCAAAGGAGA AGAACTTTTC ACTGGAGTTG TCCCAATTCT | |
| Pcore_FMD_v24 (synthetic DNA) | atcaagctgtc tccgatacact cgactaccatc cgggtctctca gagAggggaat ggcacGTAATC TTTCGGTCAAT TGTGATCTCTC TTGTAGATATT TAATAGGACGG CCAAGGTAGAA AAAGATACATA ACTAGTTAGCA AACTTCAATTG CTTAAGTTACA AGTGCAATCCA TATCTTAAAGT TATTACATTAT TTATAATGGCT AGCAAAGGAGA AGAACTTTTCA CTGGAGTTGTC CCAATTCT | 93 |

TABLE C-continued

| Primers and synthetic DNA for generation of FMD promoter variants | | |
|---|---|---|
| Name | Sequence | SEQ ID No. |
| Pcore_FMD_v25 (synthetic DNA) | atcaagctgtc tccgatacact cgactaccatc cgggtctctca gagAggggaat ggcacCCTCCT CTAGGTTTATC TATAAAAGCTG AAGTCGTTAGA ATTTTTCATTT AAAGCATAATC AAACATCTAGA TTCGAATCGAT AAAAAGCAGAT AGAAGTTATTA AGATTATAGGT TACATTCTAGA GTAGTATAGGA AGGTAATGGCT AGCAAAGGAGA AGAACTTTTCA CTGGAGTTGTC CCAATTCT | 94 |

3. Results

The results of the reporter protein fluorescence of the HpFMD promoter (P_FMD) and the AOX1 promoter (P_AOX1) wild type sequence promoters tested are shown in FIG. 4.

a) FMD Promoter Variants—Point Mutations and Single Nucleotide Insertion

TABLE D

Relative promoter activities of all promoter variants containing point mutations and single nucleotide insertions. Relative fluorescence values (RFU) of the eGFP reporter protein were measured and these values were normalized to the OD600. These RFU/OD600 values were normalized to the RFU/OD600 value of the parental HpFMD promoter variant (wt = SEQ ID No. 1) sequence resulting in relative promoter activities. The strains were cultivated in DWPs cultivation on BMD1 media (24 and48 h) and subsequently induced with methanol (72 and 96 h).

| | 24 h derepressed | | 48 h derepressed | | 72 h induced with methanol | | 96 h induced with methanol |
|---|---|---|---|---|---|---|---|
| wt | 1.0 ± 0.53 | v13 | 0.62 ± 0.058 | v09 | 0.56 ± 0.031 | v09 | 0.56 ± 0.031 |
| v12 | 1.0 ± 0.51 | v12 | 0.63 ± 0.071 | v14 | 0.56 ± 0.073 | v14 | 0.56 ± 0.073 |
| v13 | 1.1 ± 0.58 | v14 | 0.67 ± 0.088 | v12 | 0.57 ± 0.028 | v12 | 0.57 ± 0.028 |
| v09 | 1.2 ± 0.47 | v11 | 0.70 ± 0.062 | v11 | 0.58 ± 0.028 | v11 | 0.58 ± 0.028 |
| v14 | 1.3 ± 0.52 | v09 | 0.69 ± 0.088 | v13 | 0.59 ± 0.029 | v13 | 0.59 ± 0.029 |
| v11 | 1.3 ± 0.37 | v15 | 0.75 ± 0.062 | v15 | 0.69 ± 0.051 | v15 | 0.69 ± 0.051 |
| v04 | 1.3 ± 0.49 | v04 | 0.83 ± 0.083 | v04 | 0.74 ± 0.036 | v04 | 0.74 ± 0.036 |
| v19 | 1.3 ± 0.48 | v08 | 0.87 ± 0.047 | v06 | 0.77 ± 0.049 | v06 | 0.77 ± 0.049 |
| v16 | 1.3 ± 0.41 | v07 | 0.81 ± 0.071 | v07 | 0.83 ± 0.076 | v07 | 0.83 ± 0.076 |
| v15 | 1.4 ± 0.14 | v16 | 0.91 ± 0.082 | v08 | 0.83 ± 0.056 | v08 | 0.83 ± 0.056 |
| v08 | 1.4 ± 0.46 | v02 | 0.94 ± 0.10 | v16 | 0.88 ± 0.024 | v16 | 0.88 ± 0.024 |
| v07 | 1.5 ± 0.49 | v19 | 0.96 ± 0.053 | v02 | 0.9 ± 0.066 | v02 | 0.9 ± 0.066 |
| v02 | 1.5 ± 0.60 | wt | 1.0 ± 0.13 | v19 | 0.97 ± 0.079 | v19 | 0.97 ± 0.079 |
| v18 | 1.5 ± 0.59 | v03 | 1.1 ± 0.11 | v03 | 0.99 ± 0.080 | v03 | 0.99 ± 0.08 |
| v03 | 1.7 ± 0.62 | v01 | 1.1 ± 0.12 | wt | 1.0 ± 0.088 | wt | 1.0 ± 0.088 |
| v06 | 1.7 ± 0.73 | v06 | 1.1 ± 0.069 | v01 | 1.04 ± 0.066 | v01 | 1.0 ± 0.066 |
| v17 | 1.8 ± 0.63 | v18 | 1.1 ± 0.11 | v17 | 1.06 ± 0.056 | v17 | 1.1 ± 0.056 |
| v01 | 1.8 ± 0.66 | v17 | 1.2 ± 0.15 | v18 | 1.08 ± 0.12 | v18 | 1.1 ± 0.12 |
| v10 | 1.9 ± 0.65 | v10 | 1.3 ± 0.16 | v05 | 1.1 ± 0.061 | v05 | 1.1 ± 0.061 |
| v05 | 2.4 ± 0.64 | v05 | 1.4 ± 0.17 | v10 | 1.2 ± 0.066 | v10 | 1.2 ± 0.066 |

b) FMD Promoter Variants—Core Promoter Exchanges

TABLE E

Relative promoter activities of all promoter variants containing with an exchanged core promoter. Relative fluorescence values (RFU) of the eGFP reporter protein were measured and these values were normalized to the OD600. These RFU/OD600 values were normalized to the RFU/OD600 value of the parental HpFMD promoter variant (wt = SEQ ID No. 1) sequence resulting in relative promoter activities. The strains were cultivated in DWPs cultivation on BMD1 media (24 and 48 h) and subsequently induced with methanol (72 and 96 h).

| | 24 h derepressed | | 48 h derepressed | | 72 h induced with methanol | | 96 h induced with methanol |
|---|---|---|---|---|---|---|---|
| v23 | 0.36 ± 0.30 | v25 | 0.29 ± 0.067 | v25 | 0.24 ± 0.032 | v25 | 0.42 ± 0.032 |
| v25 | 0.53 ± 0.31 | v24 | 0.42 ± 0.056 | v24 | 0.41 ± 0.054 | v24 | 0.58 ± 0.022 |
| v24 | 0.59 ± 0.44 | v23 | 0.54 ± 0.070 | v23 | 0, SO ± 0.063 | v23 | 0.60 ± 0.074 |
| wt | 1.0 ± 0.44 | v22 | 0.96 ± 0.097 | v21 | 0.76 ± 0.074 | v21 | 0.92 ± 0.06 |
| v21 | 1.9 ± 0.90 | v21 | 1.0 ± 0.14 | v22 | 0.78 ± 0.089 | v22 | 0.99 ± 0.051 |
| v22 | 2.8 ± 0.36 | wt | 1.0 ± 0.098 | wt | 1.0 ± 0.132 | wt | 1.0 ± 0.134 |
| v20 | 3.7 ± 0.65 | v20 | 1.6 ± 0.14 | v20 | 1.4 ± 0.173 | v20 | 1.5 ± 0.072 |

The invention claimed is:

1. A methylotrophic *Komagataella* yeast comprising an orthologous promoter obtained from a *Hansenula* yeast cell or a variant of the orthologous promoter, inducible by derepression, wherein the orthologous promoter is an orthologous formate dehydrogenase (FMD) promoter comprising the nucleic acid sequence of SEQ ID NO: 1, and wherein the variant of the orthologous promoter comprises a nucleic acid sequence selected from the group consisting of SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55 and SEQ ID NO: 56.

2. The methylotrophic *Komagataella* yeast of claim 1, wherein the orthologous promoter is inducible with methanol.

3. The methylotrophic *Komagataella* yeast of claim 1, wherein the orthologous promoter or the variant of the orthologous promoter is operably linked to a nucleic acid molecule encoding a heterologous or homologous polypeptide, and wherein culturing the methylotrophic *Komagataella* yeast and inducing the orthologous promoter by derepression induces or increases expression of the heterologous or homologous polypeptide.

4. The methylotrophic *Komagataella* yeast of claim 3, wherein the orthologous promoter that is operably linked to the nucleic acid molecule encoding the heterologous or homologous polypeptide is present in a genome of the methylotrophic *Komagataella* yeast or as an extrachromosomal nucleic acid construct, or the variant of the orthologous promoter that is operably linked to the nucleic acid molecule encoding the heterologous or homologous polypeptide is present in a genome of the methylotrophic *Komagataella* yeast or as an extrachromosomal nucleic acid construct.

5. The methylotrophic *Komagataella* yeast of claim 3, wherein the heterologous or homologous polypeptide comprises a signal peptide.

6. The methylotrophic *Komagataella* yeast of claim 5, wherein the signal peptide is a secretion signal peptide.

7. The methylotrophic *Komagataella* yeast of claim 1, wherein the methylotrophic *Komagataella* yeast is selected from the group consisting of *Komagataella pastoris, Komagataella phaffii, Komagataella* populi, *Komagataella* pseudopastoris, *Komagataella ulmi*, and *Komagataella* sp. 11-1192.

8. A method for producing a heterologous polypeptide, comprising:

culturing the yeast cell of claim 1; and during the culturing, inducing or increasing expression of the heterologous polypeptide under derepressing conditions.

9. The method of claim 8, wherein, during the culturing, under the derepressing conditions, methanol or an alternative inductor is added.

10. The methylotrophic *Komagataella* yeast of claim 1, wherein the variant of the orthologous promoter comprises a nucleic acid sequence selected from the group consisting of SEQ ID NO: 35, SEQ ID NO: 37, SEQ ID NO: 39, SEQ ID NO: 40, SEQ ID NO: 44, SEQ ID NO: 51, SEQ ID NO: 52, SEQ ID NO: 54, SEQ ID NO: 55 and SEQ ID NO: 56.

11. The methylotrophic *Komagataella* yeast of claim 1, wherein the variant of the orthologous promoter comprises a nucleic acid sequence selected from the group consisting of SEQ ID NO: 35, SEQ ID NO: 39, SEQ ID NO: 44, SEQ ID NO: 51, SEQ ID NO: 52, SEQ ID NO: 54, SEQ ID NO: 55 and SEQ ID NO: 56.

12. The methylotrophic *Komagataella* yeast of claim 1, wherein the variant of the orthologous promoter comprises a nucleic acid sequence selected from the group consisting of SEQ ID NO: 39 and SEQ ID NO: 54.

13. A methylotrophic *Komagataella* yeast comprising an orthologous promoter obtained from a *Hansenula* yeast cell or a variant of the orthologous promoter, inducible by derepression, wherein the orthologous promoter is an orthologous formate dehydrogenase (FMD) promoter comprising the nucleic acid sequence of SEQ ID NO: 1, wherein the variant of the orthologous promoter comprises a nucleic acid sequence selected from the group consisting of SEQ ID NO: 35, SEQ ID NO: 39, SEQ ID NO: 44, SEQ ID NO: 51, SEQ ID NO: 52, SEQ ID NO: 54, SEQ ID NO: 55 and SEQ ID NO: 56, and wherein the orthologous promoter or the variant of the orthologous promoter is operably linked to a nucleic acid molecule encoding a heterologous or homologous polypeptide.

* * * * *

SEQUENCE LISTING

<160> NUMBER OF SEQ ID NOS: 94

<210> SEQ ID NO 1
<211> LENGTH: 623
<212> TYPE: DNA
<213> ORGANISM: Hansenula polymorpha

<400> SEQUENCE: 1
aatgtatcta aacgcaaact ccgagctgga aaaatgttac cggcgatgcg cggacaattt 60
agaggcggcg atcaagaaac acctgctggg cgagcagtct ggagcacagt cttcgatggg 120
cccgagatcc caccgcgttc ctgggtaccg ggacgtgagg cagcgcgaca tccatcaaat 180
ataccaggcg ccaaccgagt ctctcggaaa acagcttctg gatatcttcc gctggcggcg 240
caacgacgaa taatagtccc tggaggtgac ggaatatata tgtgtggagg gtaaatctga 300
cagggtgtag caaaggtaat attttcctaa aacatgcaat cggctgcccc gcaacgggaa 360
aaagaatgac tttggcactc ttcaccagag tggggtgtcc cgctcgtgtg tgcaaatagg 420
ctcccactgg tcaccccgga ttttgcagaa aaacagcaag ttccggggtg tctcactggt 480
gtccgccaat aagaggagcc ggcaggcacg gagtctacat caagctgtct ccgatacact 540
cgactaccat ccgggtctct cagagagggg aatggcacta taaataccgc ctccttgcgc 600
tctctgcctt catcaatcaa atc 623

<210> SEQ ID NO 2
<211> LENGTH: 1510
<212> TYPE: DNA
<213> ORGANISM: Hansenula polymorpha

<400> SEQUENCE: 2
cgacgcggag aacgatctcc tcgagctgct cgcggatcag cttgtggccc ggtaatggaa 60
ccaggccgac ggcacgctcc ttgcggacca cggtggctgg cgagcccagt ttgtgaacga 120
ggtcgtttag aacgtcctgc gcaaagtcca gtgtcagatg aatgtcctcc tcggaccaat 180
tcagcatgtt ctcgagcagc catctgtctt tggagtagaa gcgtaatctc tgctcctcgt 240
tactgtaccg gaagaggtag tttgcctcgc cgcccataat gaacaggttc tctttctggt 300
ggcctgtgag cagcggggac gtctggacgg cgtcgatgag gcccttgagg cgctcgtagt 360
acttgttcgc gtcgctgtag ccggccgcgg tgacgatacc cacatagagg tccttggcca 420

-continued ttagtttgat gaggtggggc aggatgggcg actcggcatc gaaatttttg ccgtcgtcgt 480
acagtgtgat gtcaccatcg aatgtaatga gctgcagctt gcgatctcgg atggttttgg 540
aatggaagaa ccgcgacatc tccaacagct gggccgtgtt gagaatgagc cggacgtcgt 600
tgaacgaggg ggccacaagc cggcgtttgc tgatggcgcg gcgctcgtcc tcgatgtaga 660
aggccttttc cagaggcagt ctcgtgaaga agctgccaac gctcggaacc agctgcacga 720
gccgagacaa ttcgggggtg ccggctttgg tcatttcaat gttgtcgtcg atgaggagtt 780
cgaggtcgtg gaagatttcc gcgtagcggc gttttgcctc agagtttacc atgaggtcgt 840
ccactgcaga gatgccgttg ctcttcaccg cgtacaggac gaacggcgtg gccagcaggc 900
ccttgatcca ttctatgagg ccatctcgac ggtgttcctt gagtgcgtac tccactctgt 960
agcgactgga catctcgaga ctgggcttgc tgtgctggat gcaccaatta attgttgccg 1020
catgcatcct tgcaccgcaa gtttttaaaa cccactcgct ttagccgtcg cgtaaaactt 1080
gtgaatctgg caactgaggg ggttctgcag ccgcaaccga acttttcgct tcgaggacgc 1140
agctggatgg tgtcatgtga ggctctgttt gctggcgtag cctacaacgt gaccttgcct 1200
aaccggacgg cgctacccac tgctgtctgt gcctgctacc agaaaatcac cagagcagca 1260
gagggccgat gtggcaactg gtggggtgtc ggacaggctg tttctccaca gtgcaaatgc 1320
gggtgaaccg gccagaaagt aaattcttat gctaccgtgc agtgactccg acatccccag 1380
tttttgccct acttgatcac agatggggtc agcgctgccg ctaagtgtac ccaaccgtcc 1440
ccacacggtc catctataaa tactgctgcc agtgcacggt ggtgacatca atctaaagta 1500
caaaaacaaa 1510

<210> SEQ ID NO 3
<211> LENGTH: 28
<212> TYPE: DNA
<213> ORGANISM: Artificial Sequence
<220> FEATURE:
<223> OTHER INFORMATION: Primer

<400> SEQUENCE: 3
aatgtatcta aacgcaaact ccgagctg 28

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
gatttgattg atgaaggcag agagcgcaag 30

<210> SEQ ID NO 5
<211> LENGTH: 28
<212> TYPE: DNA
<213> ORGANISM: Artificial Sequence
<220> FEATURE:
<223> OTHER INFORMATION: Primer

<400> SEQUENCE: 5
tcgacgcgga gaacgatctc ctcgagct 28

<210> SEQ ID NO 6
<211> LENGTH: 45
<212> TYPE: DNA

<213> ORGANISM: Artificial Sequence
<220> FEATURE:
<223> OTHER INFORMATION: Primer

<400> SEQUENCE: 6
tttgtttttg tactttagat tgatgtcacc accgtgcact ggcag 45

<210> SEQ ID NO 7
<211> LENGTH: 35
<212> TYPE: DNA
<213> ORGANISM: Artificial Sequence
<220> FEATURE:
<223> OTHER INFORMATION: Primer

<400> SEQUENCE: 7
cgagatggta catacttaaa agctgccata ttgag 35

<210> SEQ ID NO 8
<211> LENGTH: 56
<212> TYPE: DNA
<213> ORGANISM: Artificial Sequence
<220> FEATURE:
<223> OTHER INFORMATION: Primer

<400> SEQUENCE: 8
tttgagaaat taatagtaag attttttttt cgtaaaagtt ttgattgagt taattc 56

<210> SEQ ID NO 9
<211> LENGTH: 37
<212> TYPE: DNA
<213> ORGANISM: Artificial Sequence
<220> FEATURE:
<223> OTHER INFORMATION: Primer

<400> SEQUENCE: 9
ggatccacta cagtttacca attgattacg ccaatag 37

<210> SEQ ID NO 10
<211> LENGTH: 60
<212> TYPE: DNA
<213> ORGANISM: Artificial Sequence
<220> FEATURE:
<223> OTHER INFORMATION: Primer

<400> SEQUENCE: 10
tttgaatttt agttttagat agataaatat aattttcaat cctgttataa aatagtatat 60

<210> SEQ ID NO 11
<211> LENGTH: 55
<212> TYPE: DNA
<213> ORGANISM: Artificial Sequence
<220> FEATURE:
<223> OTHER INFORMATION: Primer

<400> SEQUENCE: 11
ggagtatacg taaatatata attatatata atcatatata tgaatacaat gaaag 55

<210> SEQ ID NO 12
<211> LENGTH: 58
<212> TYPE: DNA
<213> ORGANISM: Artificial Sequence
<220> FEATURE:
<223> OTHER INFORMATION: Primer

<400> SEQUENCE: 12
tattgaaaaa taattttgtt tttttttttt tgttttttta aaagttcgtt aaaattcg 58

<210> SEQ ID NO 13
<211> LENGTH: 28
<212> TYPE: DNA
<213> ORGANISM: Artificial Sequence
<220> FEATURE:
<223> OTHER INFORMATION: Primer

<400> SEQUENCE: 13
ggatcccttc aacagcggag tctcaaac 28

<210> SEQ ID NO 14
<211> LENGTH: 58
<212> TYPE: DNA
<213> ORGANISM: Artificial Sequence
<220> FEATURE:
<223> OTHER INFORMATION: Primer

<400> SEQUENCE: 14
ttttgtggaa taaaaaatag ataaatatga tttagtgtag ttgattcaat caattgac 58

<210> SEQ ID NO 15
<211> LENGTH: 60
<212> TYPE: DNA
<213> ORGANISM: Artificial Sequence
<220> FEATURE:
<223> OTHER INFORMATION: Primer

<400> SEQUENCE: 15
cttgcgctct ctgccttcat caatcaaatc atgagattcc catctatttt caccgctgtc 60

<210> SEQ ID NO 16
<211> LENGTH: 60
<212> TYPE: DNA
<213> ORGANISM: Artificial Sequence
<220> FEATURE:
<223> OTHER INFORMATION: Primer

<400> SEQUENCE: 16
caaatggcat tctgacatcc tcttgagcgg ccgcttatgg ggtcacgata ccggaacaag 60

<210> SEQ ID NO 17
<211> LENGTH: 66
<212> TYPE: DNA
<213> ORGANISM: Artificial Sequence
<220> FEATURE:
<223> OTHER INFORMATION: Primer

<400> SEQUENCE: 17
caaatggcat tctgacatcc tcttgagcgg ccgcttagga tccgttaact ttcttgcaat 60
caagtc 66

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
actggtgtcc gccaataaga ggag 24

<210> SEQ ID NO 19
<211> LENGTH: 60
<212> TYPE: DNA

-continued

```
<213> ORGANISM: Artificial Sequence
<220> FEATURE:
<223> OTHER INFORMATION: Primer

<400> SEQUENCE: 19

cttgcgctct ctgccttcat caatcaaatc atggttactg ctcacttcgt cttgattcac     60


<210> SEQ ID NO 20
<211> LENGTH: 61
<212> TYPE: DNA
<213> ORGANISM: Artificial Sequence
<220> FEATURE:
<223> OTHER INFORMATION: Primer

<400> SEQUENCE: 20

caaatggcat tctgacatcc tcttgagcgg ccgcttaagc gtaagcgtcg gcaacttcct     60

g                                                                     61


<210> SEQ ID NO 21
<211> LENGTH: 60
<212> TYPE: DNA
<213> ORGANISM: Artificial Sequence
<220> FEATURE:
<223> OTHER INFORMATION: Primer

<400> SEQUENCE: 21

cacttgctct agtcaagact tacaattaaa atggttactg ctcacttcgt cttgattcac     60


<210> SEQ ID NO 22
<211> LENGTH: 868
<212> TYPE: DNA
<213> ORGANISM: Artificial Sequence
<220> FEATURE:
<223> OTHER INFORMATION: MeHNL coding sequence with overhangs to cloning
      vector

<400> SEQUENCE: 22

cgacaacttg agaagatcaa aaaacaacta attattgaaa gaattccgaa acgatggtta     60

ctgctcactt cgtcttgatt cacactatct gtcatggtgc ttggatctgg cacaagttga    120

agccagcatt ggagagagct ggacataagg ttaccgctct tgatatggct gcatctggta    180

ttgatcctcg tcaaatcgaa caaatcaatt cattcgacga gtactcagag ccactgctga    240

ccttcttgga aaagttgcct caaggtgaaa aggtgatcat cgttggtgaa tcctgtgctg    300

gattgaacat tgccattgca gctgatagat atgtcgataa gatcgctgct ggtgtcttcc    360

acaactctct gttaccagat actgttcact ctccatctta cactgtcgag aagttgttag    420

aatcattccc agattggaga gatactgaat actttacttt cactaacatc actggagaga    480

ctatcaccac catgaaactt ggattcgttt tgttgagaga aaaccttttc accaagtgta    540

ctgatggtga atacgaattg gccaagatgg ttatgagaaa gggttctttg tttcagaatg    600

ttcttgcaca aagaccaaag ttcaccgaaa agggttacgg ttctatcaag aaggtctaca    660

tctggactga tcaggacaag atcttcctgc cagacttcca aagatggcaa atcgcaaact    720

acaaaccaga taaggtctac caagtccaag gtggtgatca caagttacaa ttgaccaaga    780

ccgaagaggt cgctcacatc ttgcaggaag ttgccgacgc ttacgcttaa gcggccgctc    840

aagaggatgt cagaatgcca tttgcctg                                       868


<210> SEQ ID NO 23
<211> LENGTH: 572
<212> TYPE: DNA
```

<213> ORGANISM: Candida boidinii

<400> SEQUENCE: 23

```
ggatcccttc aacagcggag tctcaagcag tggctattat cagtgtattt aattactgat     60
gcattgtatt atagtgcata catagttaat aattactctc tgttatcatt gaaaattttg    120
aaattctcac tctcacgcag tgcaaaactt tgcctaattg agtaagtgga acgcaatatt    180
taggctacat attttggatt cccttaagta tgtaatcaaa gatcattcat actgccatct    240
tataatattg gagtattatt atgttgctat actgttctac ctgtttattc tattgtatgc    300
gtctaaatct ttccatcagt ttctatacta tctttcgttt gcaatgaaat attactccaa    360
ttcgcttgtt tcaactcgct tgccttctct cttgccttct ttttttcttt tcattttatc    420
gttgtttaaa cggtatataa atatgtaacg ttgtcgctta gttttgagaa atcacttttg    480
ttgctctcaa ttctgttttg acatcttaag gttagtcaat tgattgaatc aactacacta    540
aatcatattt atctattttt tattccacaa aa                                  572
```

<210> SEQ ID NO 24
<211> LENGTH: 1652
<212> TYPE: DNA
<213> ORGANISM: Candida boidinii

<400> SEQUENCE: 24

```
ggagtatacg taaatatata attatatata atcatatata tgaatacaat gcaatgaaag     60
tgaatatgat aagattgaaa taataacaaa cagcgataaa tatatctcaa aatggagtta    120
cacaacaaat aataataaaa tataaattat aaattataaa ttataaaaga ataaaaaata    180
aaccccacta atttatttta ttaaaagata gattggtatc tttacttaat aacaattctg    240
aaactttatt cacttaattt tatttaactt atttaattta tttttacccc agtttttcag    300
tacaatgcag ctccgaaact ttatttggct gtgatttggc tgtgatttgg ctgtgatttg    360
gcttggcttg gctggctgga attgtctcct gcaggaattg ctcggggtcc ggttctcccg    420
ctggctggct atttggcggg ctggctattt ggcgggctgg ctggctggct gctctgccat    480
ctgctgtggc caccccgcat ctctggatgc acgccgtgca gctggacgtg cgtctaccct    540
gcagccgtgt gccttatttc ccaatctccc aatctctcaa tctgccagtc agccaaaaca    600
ccggccaggc aggcaggcag gcaggcaggc aggcagtgaa gccttcccac gccccactcc    660
gcataaacat ccccagcagt ttccccagca gtttccccag cttttcaatt taataaaata    720
gcctgtttct gtttctgttt tatattatac aattttttat cctaataatt actctttcgg    780
gaattaaata ataattatat catataccca tatcacattt tactatattt actatctata    840
aataaattca tattataata ttaatttata ttcgcttaat taaaatgctc ttttccatca    900
tcatcatcat catcatcatc acgagttttc ggttatcaat actcttttca ttaatttcta    960
gaatttcatt atttattttt tattgactgg aaattttcaa tcaattttat ttatttttat   1020
ttatttattt tcatattctt agatttaaac tttttagatg accgctattt tacttactta   1080
cttactgttg ttttatatta tgataagaat taattttcat atttatgatg atgatgatgt   1140
aaatttaacc tagtatacta ttttaaagtt atcactatct tttagtgctg gcattttttta  1200
ttctattttc atatatgtat atacgtaaat taagtatcat cacgctgctt actgtacgtt   1260
taaaatgtgg agatggaaat agagatgggg atgaagatga agatgatgag aattataaac   1320
cattcattca ttaatcaatc aatataactt ataaaaaaat ttatatttaa atgaattaat   1380
ttcctttatt ttaataatat cgttaattct tttaaattct attttatttt aattctttct   1440
```

```
ttatcatagt tatcatataa caattatata acatagatac acaattatta tttcattatc    1500

atattatttt ttaaaatatt gattattttt aaaataatat cttaattaat taattttac     1560

gaatatacaa attttaacga cttacttttt ttaacgaatt ttaacgaact tttaaaaaaa    1620

caaaaaaaaa aaaacaaaat tatttttcaa ta                                  1652

<210> SEQ ID NO 25
<211> LENGTH: 1157
<212> TYPE: DNA
<213> ORGANISM: Pichia methanolica

<400> SEQUENCE: 25

cgagatggta catacttaaa agctgccata ttgaggaact tcaaagtttt atctgttttt      60

agaattaaaa gacgattgtt gtaacaaaac gttgtgccta cataaactca aattaatgga    120

aatagcctgt tttgaaaaat acaccttctt aagtactgac aaagttttgt taaatgacta    180

tcgaacaagc catgaaatag cacatttctg ccagtcactt ttaacacttt cctgcttgct    240

ggttgactct cctcatacaa acacccaaaa gggaaacttt cagtgtgggg acacttgaca    300

tctcacatgc accccagatt aatttcccca gacgatgcgg agacaagaca aaacaaccct    360

ttgtcctgct cttttctttc tcacaccgcg tgggtgtgtg cgcaggcagg caggcaggca    420

gcgggctgcc tgccatctct aatcgctgct cctcccccct ggcttcaaat aacagcctgc    480

tgctatctgt gaccagattg ggacaccccc ctcccctccg aatgatccat cacctttgt     540

cgtactccga caatgatcct tccctgtcat cttctggcaa tcagctcctt caataattaa    600

atcaaataag cataaatagt aaaatcgcat acaaacgtca tgaaaagttt tatctctatg    660

gccaacggat agtctatctg cttaattcca tccactttgg gaaccgttct ctctttaccc    720

cagattctca aagctaatat ctgccccttg tctattgtcc tttctccgtg tacaagcgga    780

gcttttgcct cccatcctct tgctttgttt cggttatttt ttttttcttt gaaactcttg    840

gtcaaatcaa atcaaacaaa accaaacctt ctattccatc agatcaacct tgttcaacat    900

tctataaatc gatataaata taaccttatc cctcccttgt tttttaccaa ttaatcaatc    960

ttcaaatttc aaatattttc tacttgcttt attactcagt attaacattt gtttaaacca   1020

actataactt ttaactggct ttagaagttt tatttaacat cagtttcaat ttacatcttt   1080

atttattaac gaaatcttta cgaattaact caatcaaaac ttttacgaaa aaaaaatctt   1140

actattaatt tctcaaa                                                  1157

<210> SEQ ID NO 26
<211> LENGTH: 1662
<212> TYPE: DNA
<213> ORGANISM: Pichia methanolica

<400> SEQUENCE: 26

ggatccacta cagtttacca attgattacg ccaatgtgtt tatttcacca agtaattaca      60

aaactgagat ttggttatgt cattatgtat tttcggcaat ggctgtaatt taaactggat    120

tagggttaat taacgtttag cctacgaaag cggctagctt ttatttctgc ttttgttttg    180

agcccgtttc taattccaat ctttgcaatt tcgttccatc ttttaaaatt aagtgctctt    240

ttctaatctg ataaagataa gccatcgtag agtaagtaaa acaaaataat gtactgtata    300

ttaagcggaa aaacttggaa aagtcgtatg atgttgaagg agcaaagaat gactaatatt    360

aggagattta agcaaacaat gttgagggga acaggacgat taacccctta tagaggaagc    420
```

```
gtctttgatg ttcgaagggg gaggggtcaa aagcactgag cagtgctaat tagtaaccaa    480

tttctgtaag caatgaaact tgttgctatt ggaaatacta ttaagtaata caaggtacag    540

actaatgggg gtgagccggt agttcaggct atcttataga cagactattc cggattgtct    600

aatcattggt gcacctggtt aataattatc agtcaactct tttacggtgc tgataggtct    660

ttgcgaactt gcccttgtgg aatttggttg ttaatcaaac tgttctgtat ttcatgtcat    720

actactattg atattattaa tgttacttac tcatctggcc atttaacagg tttgaagctt    780

taatgctctt aactaacagc aatccatcac cgtcaacctt aaccccccctg gtgcttgctg   840

tctttatcct tcgtatcttt ttcatgttgc accgccctgt tccttatacg gttgttcccc    900

cataggctaa cttctctgtt tccgaccatc tctgcaataa caaagaattc tatacgctta    960

cactataatc atacaatgac tctacatgcc attttcactt tacttacttg ccatcggaag   1020

atactgaatc agaaagccat agtaactaca taacttcaaa acacaccctt tttacagatt   1080

agttacaatt ttgtcaatgt ttgtttgata acccaaggtg gaacgtttcc agttagacct   1140

gtttaatcca actcacttta ccaccccaaa actttcctac cgttagacaa atactggcta   1200

aatctgacga aaacaaccaa tcaacaattg aatccactgg gaggtatctc taatccactg   1260

acaaactttg ctaaaacaag aaaaagtggg ggcctccgtt gcggagaaga cgtgcgcagg   1320

cttaaaaaca caagagaaca cttggaagta ccccagattt ttagcttcct actattctga   1380

cacccccctat tcaagcacga cggtgattga ttcattcaat tttgctgctc caatgatagg  1440

ataaaccctt ttggacttca atcagacctc tgtcctccat agcaatataa ataccttcta   1500

gttgccccac ttcctctctc ctgtactgcc ccaatgagtg acttattcaa gttactttct   1560

ctcttttcct aacaattaaa caagaagctt tattataaca ttaatatact attttataac   1620

aggattgaaa ttatatttat ctatctaaaa ctaaaattca aa                      1662
```

<210> SEQ ID NO 27
<211> LENGTH: 579
<212> TYPE: DNA
<213> ORGANISM: Artificial Sequence
<220> FEATURE:
<223> OTHER INFORMATION: FMD variant
<220> FEATURE:
<221> NAME/KEY: misc_feature
<222> LOCATION: (72)..(72)
<223> OTHER INFORMATION: n is adenine or no nucleotide
<220> FEATURE:
<221> NAME/KEY: misc_feature
<222> LOCATION: (354)..(354)
<223> OTHER INFORMATION: n is adenine or guanine
<220> FEATURE:
<221> NAME/KEY: misc_feature
<222> LOCATION: (455)..(455)
<223> OTHER INFORMATION: n is cytosine or thymine
<220> FEATURE:
<221> NAME/KEY: misc_feature
<222> LOCATION: (551)..(551)
<223> OTHER INFORMATION: n is thymine or guanine
<220> FEATURE:
<221> NAME/KEY: misc_feature
<222> LOCATION: (563)..(563)
<223> OTHER INFORMATION: n is adenine or cytosine
<220> FEATURE:
<221> NAME/KEY: misc_feature
<222> LOCATION: (564)..(564)
<223> OTHER INFORMATION: n is guanine or cytosine
<220> FEATURE:
<221> NAME/KEY: misc_feature
<222> LOCATION: (565)..(565)
<223> OTHER INFORMATION: n is adenine or cytosine
<220> FEATURE:
<221> NAME/KEY: misc_feature
<222> LOCATION: (566)..(566)
<223> OTHER INFORMATION: n is guanine or cytosine
<220> FEATURE:
<221> NAME/KEY: misc_feature
<222> LOCATION: (567)..(567)
<223> OTHER INFORMATION: n is adenine, guanine or cytosine
<220> FEATURE:
<221> NAME/KEY: misc_feature
<222> LOCATION: (568)..(568)
<223> OTHER INFORMATION: n is guanine or cytosine
<220> FEATURE:
<221> NAME/KEY: misc_feature
<222> LOCATION: (569)..(569)
<223> OTHER INFORMATION: n is guanine or cytosine
<220> FEATURE:
<221> NAME/KEY: misc_feature
<222> LOCATION: (570)..(570)
<223> OTHER INFORMATION: n is guanine or cytosine
<220> FEATURE:
<221> NAME/KEY: misc_feature
<222> LOCATION: (571)..(571)
<223> OTHER INFORMATION: n is guanine or cytosine
<220> FEATURE:
<221> NAME/KEY: misc_feature
<222> LOCATION: (572)..(572)
<223> OTHER INFORMATION: n is adenine or cytosine
<220> FEATURE:
<221> NAME/KEY: misc_feature
<222> LOCATION: (573)..(573)
<223> OTHER INFORMATION: n is adenine or cytosine
<220> FEATURE:
<221> NAME/KEY: misc_feature
<222> LOCATION: (574)..(574)
<223> OTHER INFORMATION: n is thymine or cytosine
<220> FEATURE:
<221> NAME/KEY: misc_feature
<222> LOCATION: (575)..(575)
<223> OTHER INFORMATION: n is guanine or cytosine
<220> FEATURE:
<221> NAME/KEY: misc_feature
<222> LOCATION: (576)..(576)
<223> OTHER INFORMATION: n is guanine or cytosine

<400> SEQUENCE: 27
aatgtatcta aacgcaaact ccgagctgga aaaatgttac cggcgatgcg cggacaattt 60
agaggcggcg antcaagaaa cacctgctgg gcgagcagtc tggagcacag tcttcgatgg 120
gcccgagatc ccaccgcgtt cctgggtacc gggacgtgag gcagcgcgac atccatcaaa 180
tataccaggc gccaaccgag tctctcggaa aacagcttct ggatatcttc cgctggcggc 240
gcaacgacga ataatagtcc ctggaggtga cggaatatat atgtgtggag ggtaaatctg 300
acagggtgta gcaaaggtaa tattttccta aaacatgcaa tcggctgccc cgcnacggga 360
aaaagaatga ctttggcact cttcaccaga gtggggtgtc ccgctcgtgt gtgcaaatag 420
gctcccactg gtcaccccgg attttgcaga aaaanagcaa gttccggggt gtctcactgg 480
tgtccgccaa taagaggagc cggcaggcac ggagtctaca tcaagctgtc tccgatacac 540
tcgactacca nccgggtctc tcnnnnnnnn nnnnnncac 579

<210> SEQ ID NO 28
<211> LENGTH: 45
<212> TYPE: DNA
<213> ORGANISM: Artificial Sequence
<220> FEATURE:
<223> OTHER INFORMATION: core promoter of an orthologous promoter

<400> SEQUENCE: 28
tataaatacc gcctccttgc gctctctgcc ttcatcaatc aaatc 45

<210> SEQ ID NO 29

<211> LENGTH: 70
<212> TYPE: DNA
<213> ORGANISM: Artificial Sequence
<220> FEATURE:
<223> OTHER INFORMATION: core promoter of an orthologous promoter

<400> SEQUENCE: 29
tatataaact ggtgataatt ccttcgttct gagttccatc tcatactcaa actatattaa 60
aactacaaca 70

<210> SEQ ID NO 30
<211> LENGTH: 61
<212> TYPE: DNA
<213> ORGANISM: Artificial Sequence
<220> FEATURE:
<223> OTHER INFORMATION: core promoter of an orthologous promoter

<400> SEQUENCE: 30
tataaataca agacgagtgc gtccttttct agactcaccc ataaacaaat aatcaataaa 60
t 61

<210> SEQ ID NO 31
<211> LENGTH: 45
<212> TYPE: DNA
<213> ORGANISM: Artificial Sequence
<220> FEATURE:
<223> OTHER INFORMATION: core promoter of an orthologous promoter

<400> SEQUENCE: 31
tataaatact gcctacttgt cctctattcc ttcatcaatc acatc 45

<210> SEQ ID NO 32
<211> LENGTH: 143
<212> TYPE: DNA
<213> ORGANISM: Artificial Sequence
<220> FEATURE:
<223> OTHER INFORMATION: core promoter of an orthologous promoter

<400> SEQUENCE: 32
cgatagggca gaaatatata aagtaggagg ttgtatacca aatataccaa cgcagtacaa 60
gcaactcttg gtttaaacgg aagaaacaat tcttcgaaca tttacaacaa agaaggtacc 120
gtaacattaa taatcggaag ggt 143

<210> SEQ ID NO 33
<211> LENGTH: 143
<212> TYPE: DNA
<213> ORGANISM: Artificial Sequence
<220> FEATURE:
<223> OTHER INFORMATION: core promoter of an orthologous promoter

<400> SEQUENCE: 33
gtaatctttc ggtcaattgt gatctctctt gtagatattt aataggacgg ccaaggtaga 60
aaaagataca taactagtta gcaaacttca attgcttaag ttacaagtgc aatccatatc 120
ttaaagttat tacattattt ata 143

<210> SEQ ID NO 34
<211> LENGTH: 143
<212> TYPE: DNA
<213> ORGANISM: Artificial Sequence
<220> FEATURE:
<223> OTHER INFORMATION: core promoter of an orthologous promoter

<400> SEQUENCE: 34

-continued cctcctctag gtttatctat aaaagctgaa gtcgttagaa tttttcattt aaagcataat 60
caaacatcta gattcgaatc gataaaaagc agatagaagt tattaagatt ataggttaca 120
ttctagagta gtataggaag gta 143

<210> SEQ ID NO 35
<211> LENGTH: 624
<212> TYPE: DNA
<213> ORGANISM: Artificial Sequence
<220> FEATURE:
<223> OTHER INFORMATION: FMD variant v1

<400> SEQUENCE: 35
aatgtatcta aacgcaaact ccgagctgga aaaatgttac cggcgatgcg cggacaattt 60
agaggcggcg aatcaagaaa cacctgctgg gcgagcagtc tggagcacag tcttcgatgg 120
gcccgagatc ccaccgcgtt cctgggtacc gggacgtgag gcagcgcgac atccatcaaa 180
tataccaggc gccaaccgag tctctcggaa aacagcttct ggatatcttc cgctggcggc 240
gcaacgacga ataatagtcc ctggaggtga cggaatatat atgtgtggag ggtaaatctg 300
acagggtgta gcaaaggtaa tattttccta aaacatgcaa tcggctgccc cgcaacggga 360
aaaagaatga ctttggcact cttcaccaga gtggggtgtc ccgctcgtgt gtgcaaatag 420
gctcccactg gtcaccccgg attttgcaga aaaacagcaa gttccggggt gtctcactgg 480
tgtccgccaa taagaggagc cggcaggcac ggagtctaca tcaagctgtc tccgatacac 540
tcgactacca tccgggtctc tcagagaggg gaatggcact ataaataccg cctccttgcg 600
ctctctgcct tcatcaatca aatc 624

<210> SEQ ID NO 36
<211> LENGTH: 623
<212> TYPE: DNA
<213> ORGANISM: Artificial Sequence
<220> FEATURE:
<223> OTHER INFORMATION: FMD variant v2

<400> SEQUENCE: 36
aatgtatcta aacgcaaact ccgagctgga aaaatgttac cggcgatgcg cggacaattt 60
agaggcggcg atcaagaaac acctgctggg cgagcagtct ggagcacagt cttcgatggg 120
cccgagatcc caccgcgttc ctgggtaccg ggacgtgagg cagcgcgaca tccatcaaat 180
ataccaggcg ccaaccgagt ctctcggaaa acagcttctg gatatcttcc gctggcggcg 240
caacgacgaa taatagtccc tggaggtgac ggaatatata tgtgtggagg gtaaatctga 300
cagggtgtag caaaggtaat attttcctaa aacatgcaat cggctgcccc gcgacgggaa 360
aaagaatgac tttggcactc ttcaccagag tggggtgtcc cgctcgtgtg tgcaaatagg 420
ctcccactgg tcaccccgga ttttgcagaa aaacagcaag ttccggggtg tctcactggt 480
gtccgccaat aagaggagcc ggcaggcacg gagtctacat caagctgtct ccgatacact 540
cgactaccat ccgggtctct cagagagggg aatggcacta taaataccgc ctccttgcgc 600
tctctgcctt catcaatcaa atc 623

<210> SEQ ID NO 37
<211> LENGTH: 623
<212> TYPE: DNA
<213> ORGANISM: Artificial Sequence
<220> FEATURE:
<223> OTHER INFORMATION: FMD variant v3

<400> SEQUENCE: 37
aatgtatcta aacgcaaact ccgagctgga aaaatgttac cggcgatgcg cggacaattt 60
agaggcggcg atcaagaaac acctgctggg cgagcagtct ggagcacagt cttcgatggg 120
cccgagatcc caccgcgttc ctgggtaccg ggacgtgagg cagcgcgaca tccatcaaat 180
ataccaggcg ccaaccgagt ctctcggaaa acagcttctg gatatcttcc gctggcggcg 240
caacgacgaa taatagtccc tggaggtgac ggaatatata tgtgtggagg gtaaatctga 300
cagggtgtag caaaggtaat attttcctaa aacatgcaat cggctgcccc gcaacgggaa 360
aaagaatgac tttggcactc ttcaccagag tggggtgtcc cgctcgtgtg tgcaaatagg 420
ctcccactgg tcaccccgga ttttgcagaa aaatagcaag ttccggggtg tctcactggt 480
gtccgccaat aagaggagcc ggcaggcacg gagtctacat caagctgtct ccgatacact 540
cgactaccat ccgggtctct cagagagggg aatggcacta taaataccgc ctccttgcgc 600
tctctgcctt catcaatcaa atc 623

<210> SEQ ID NO 38
<211> LENGTH: 623
<212> TYPE: DNA
<213> ORGANISM: Artificial Sequence
<220> FEATURE:
<223> OTHER INFORMATION: FMD variant v4

<400> SEQUENCE: 38
aatgtatcta aacgcaaact ccgagctgga aaaatgttac cggcgatgcg cggacaattt 60
agaggcggcg atcaagaaac acctgctggg cgagcagtct ggagcacagt cttcgatggg 120
cccgagatcc caccgcgttc ctgggtaccg ggacgtgagg cagcgcgaca tccatcaaat 180
ataccaggcg ccaaccgagt ctctcggaaa acagcttctg gatatcttcc gctggcggcg 240
caacgacgaa taatagtccc tggaggtgac ggaatatata tgtgtggagg gtaaatctga 300
cagggtgtag caaaggtaat attttcctaa aacatgcaat cggctgcccc gcaacgggaa 360
aaagaatgac tttggcactc ttcaccagag tggggtgtcc cgctcgtgtg tgcaaatagg 420
ctcccactgg tcaccccgga ttttgcagaa aaacagcaag ttccggggtg tctcactggt 480
gtccgccaat aagaggagcc ggcaggcacg gagtctacat caagctgtct ccgatacact 540
cgactaccat ccgggtctct cagagggggg aatggcacta taaataccgc ctccttgcgc 600
tctctgcctt catcaatcaa atc 623

<210> SEQ ID NO 39
<211> LENGTH: 623
<212> TYPE: DNA
<213> ORGANISM: Artificial Sequence
<220> FEATURE:
<223> OTHER INFORMATION: FMD variant v5

<400> SEQUENCE: 39
aatgtatcta aacgcaaact ccgagctgga aaaatgttac cggcgatgcg cggacaattt 60
agaggcggcg atcaagaaac acctgctggg cgagcagtct ggagcacagt cttcgatggg 120
cccgagatcc caccgcgttc ctgggtaccg ggacgtgagg cagcgcgaca tccatcaaat 180
ataccaggcg ccaaccgagt ctctcggaaa acagcttctg gatatcttcc gctggcggcg 240
caacgacgaa taatagtccc tggaggtgac ggaatatata tgtgtggagg gtaaatctga 300
cagggtgtag caaaggtaat attttcctaa aacatgcaat cggctgcccc gcaacgggaa 360
aaagaatgac tttggcactc ttcaccagag tggggtgtcc cgctcgtgtg tgcaaatagg 420

```
ctcccactgg tcaccccgga ttttgcagaa aaacagcaag ttccggggtg tctcactggt    480

gtccgccaat aagaggagcc ggcaggcacg gagtctacat caagctgtct ccgatacact    540

cgactaccag ccgggtctct cagagagggg aatggcacta taaataccgc ctccttgcgc    600

tctctgcctt catcaatcaa atc                                            623


<210> SEQ ID NO 40
<211> LENGTH: 623
<212> TYPE: DNA
<213> ORGANISM: Artificial Sequence
<220> FEATURE:
<223> OTHER INFORMATION: FMD variant v6

<400> SEQUENCE: 40

aatgtatcta aacgcaaact ccgagctgga aaaatgttac cggcgatgcg cggacaattt     60

agaggcggcg atcaagaaac acctgctggg cgagcagtct ggagcacagt cttcgatggg    120

cccgagatcc caccgcgttc ctgggtaccg ggacgtgagg cagcgcgaca tccatcaaat    180

ataccaggcg ccaaccgagt ctctcggaaa acagcttctg gatatcttcc gctggcggcg    240

caacgacgaa taatagtccc tggaggtgac ggaatatata tgtgtggagg gtaaatctga    300

cagggtgtag caaaggtaat attttcctaa aacatgcaat cggctgcccc gcaacgggaa    360

aaagaatgac tttggcactc ttcaccagag tggggtgtcc cgctcgtgtg tgcaaatagg    420

ctcccactgg tcaccccgga ttttgcagaa aaacagcaag ttccggggtg tctcactggt    480

gtccgccaat aagaggagcc ggcaggcacg gagtctacat caagctgtct ccgatacact    540

cgactaccat ccgggtctct ccgagagggg aatggcacta taaataccgc ctccttgcgc    600

tctctgcctt catcaatcaa atc                                            623


<210> SEQ ID NO 41
<211> LENGTH: 623
<212> TYPE: DNA
<213> ORGANISM: Artificial Sequence
<220> FEATURE:
<223> OTHER INFORMATION: FMD variant v7

<400> SEQUENCE: 41

aatgtatcta aacgcaaact ccgagctgga aaaatgttac cggcgatgcg cggacaattt     60

agaggcggcg atcaagaaac acctgctggg cgagcagtct ggagcacagt cttcgatggg    120

cccgagatcc caccgcgttc ctgggtaccg ggacgtgagg cagcgcgaca tccatcaaat    180

ataccaggcg ccaaccgagt ctctcggaaa acagcttctg gatatcttcc gctggcggcg    240

caacgacgaa taatagtccc tggaggtgac ggaatatata tgtgtggagg gtaaatctga    300

cagggtgtag caaaggtaat attttcctaa aacatgcaat cggctgcccc gcaacgggaa    360

aaagaatgac tttggcactc ttcaccagag tggggtgtcc cgctcgtgtg tgcaaatagg    420

ctcccactgg tcaccccgga ttttgcagaa aaacagcaag ttccggggtg tctcactggt    480

gtccgccaat aagaggagcc ggcaggcacg gagtctacat caagctgtct ccgatacact    540

cgactaccat ccgggtctct cacagagggg aatggcacta taaataccgc ctccttgcgc    600

tctctgcctt catcaatcaa atc                                            623


<210> SEQ ID NO 42
<211> LENGTH: 623
<212> TYPE: DNA
<213> ORGANISM: Artificial Sequence
<220> FEATURE:
```

-continued

<223> OTHER INFORMATION: FMD variant v8

<400> SEQUENCE: 42

```
aatgtatcta aacgcaaact ccgagctgga aaaatgttac cggcgatgcg cggacaattt     60
agaggcggcg atcaagaaac acctgctggg cgagcagtct ggagcacagt cttcgatggg    120
cccgagatcc caccgcgttc ctgggtaccg ggacgtgagg cagcgcgaca tccatcaaat    180
ataccaggcg ccaaccgagt ctctcggaaa acagcttctg gatatcttcc gctggcggcg    240
caacgacgaa taatagtccc tggaggtgac ggaatatata tgtgtggagg gtaaatctga    300
cagggtgtag caaaggtaat attttcctaa aacatgcaat cggctgcccc gcaacgggaa    360
aaagaatgac tttggcactc ttcaccagag tggggtgtcc cgctcgtgtg tgcaaatagg    420
ctcccactgg tcaccccgga ttttgcagaa aaacagcaag ttccggggtg tctcactggt    480
gtccgccaat aagaggagcc ggcaggcacg gagtctacat caagctgtct ccgatacact    540
cgactaccat ccgggtctct cagcgagggg aatggcacta taaataccgc ctccttgcgc    600
tctctgcctt catcaatcaa atc                                            623
```

<210> SEQ ID NO 43
<211> LENGTH: 623
<212> TYPE: DNA
<213> ORGANISM: Artificial Sequence
<220> FEATURE:
<223> OTHER INFORMATION: FMD variant v9

<400> SEQUENCE: 43

```
aatgtatcta aacgcaaact ccgagctgga aaaatgttac cggcgatgcg cggacaattt     60
agaggcggcg atcaagaaac acctgctggg cgagcagtct ggagcacagt cttcgatggg    120
cccgagatcc caccgcgttc ctgggtaccg ggacgtgagg cagcgcgaca tccatcaaat    180
ataccaggcg ccaaccgagt ctctcggaaa acagcttctg gatatcttcc gctggcggcg    240
caacgacgaa taatagtccc tggaggtgac ggaatatata tgtgtggagg gtaaatctga    300
cagggtgtag caaaggtaat attttcctaa aacatgcaat cggctgcccc gcaacgggaa    360
aaagaatgac tttggcactc ttcaccagag tggggtgtcc cgctcgtgtg tgcaaatagg    420
ctcccactgg tcaccccgga ttttgcagaa aaacagcaag ttccggggtg tctcactggt    480
gtccgccaat aagaggagcc ggcaggcacg gagtctacat caagctgtct ccgatacact    540
cgactaccat ccgggtctct cagacagggg aatggcacta taaataccgc ctccttgcgc    600
tctctgcctt catcaatcaa atc                                            623
```

<210> SEQ ID NO 44
<211> LENGTH: 623
<212> TYPE: DNA
<213> ORGANISM: Artificial Sequence
<220> FEATURE:
<223> OTHER INFORMATION: FMD variant v10

<400> SEQUENCE: 44

```
aatgtatcta aacgcaaact ccgagctgga aaaatgttac cggcgatgcg cggacaattt     60
agaggcggcg atcaagaaac acctgctggg cgagcagtct ggagcacagt cttcgatggg    120
cccgagatcc caccgcgttc ctgggtaccg ggacgtgagg cagcgcgaca tccatcaaat    180
ataccaggcg ccaaccgagt ctctcggaaa acagcttctg gatatcttcc gctggcggcg    240
caacgacgaa taatagtccc tggaggtgac ggaatatata tgtgtggagg gtaaatctga    300
cagggtgtag caaaggtaat attttcctaa aacatgcaat cggctgcccc gcaacgggaa    360
```

aaagaatgac tttggcactc ttcaccagag tggggtgtcc cgctcgtgtg tgcaaatagg 420
ctcccactgg tcaccccgga ttttgcagaa aaacagcaag ttccggggtg tctcactggt 480
gtccgccaat aagaggagcc ggcaggcacg gagtctacat caagctgtct ccgatacact 540
cgactaccat ccgggtctct cagagcgggg aatggcacta taaataccgc ctccttgcgc 600
tctctgcctt catcaatcaa atc 623

<210> SEQ ID NO 45
<211> LENGTH: 623
<212> TYPE: DNA
<213> ORGANISM: Artificial Sequence
<220> FEATURE:
<223> OTHER INFORMATION: FMD variant v11

<400> SEQUENCE: 45
aatgtatcta aacgcaaact ccgagctgga aaaatgttac cggcgatgcg cggacaattt 60
agaggcggcg atcaagaaac acctgctggg cgagcagtct ggagcacagt cttcgatggg 120
cccgagatcc caccgcgttc ctgggtaccg ggacgtgagg cagcgcgaca tccatcaaat 180
ataccaggcg ccaaccgagt ctctcggaaa acagcttctg gatatcttcc gctggcggcg 240
caacgacgaa taatagtccc tggaggtgac ggaatatata tgtgtggagg gtaaatctga 300
cagggtgtag caaaggtaat attttcctaa aacatgcaat cggctgcccc gcaacgggaa 360
aaagaatgac tttggcactc ttcaccagag tggggtgtcc cgctcgtgtg tgcaaatagg 420
ctcccactgg tcaccccgga ttttgcagaa aaacagcaag ttccggggtg tctcactggt 480
gtccgccaat aagaggagcc ggcaggcacg gagtctacat caagctgtct ccgatacact 540
cgactaccat ccgggtctct cagagacggg aatggcacta taaataccgc ctccttgcgc 600
tctctgcctt catcaatcaa atc 623

<210> SEQ ID NO 46
<211> LENGTH: 623
<212> TYPE: DNA
<213> ORGANISM: Artificial Sequence
<220> FEATURE:
<223> OTHER INFORMATION: FMD variant v12

<400> SEQUENCE: 46
aatgtatcta aacgcaaact ccgagctgga aaaatgttac cggcgatgcg cggacaattt 60
agaggcggcg atcaagaaac acctgctggg cgagcagtct ggagcacagt cttcgatggg 120
cccgagatcc caccgcgttc ctgggtaccg ggacgtgagg cagcgcgaca tccatcaaat 180
ataccaggcg ccaaccgagt ctctcggaaa acagcttctg gatatcttcc gctggcggcg 240
caacgacgaa taatagtccc tggaggtgac ggaatatata tgtgtggagg gtaaatctga 300
cagggtgtag caaaggtaat attttcctaa aacatgcaat cggctgcccc gcaacgggaa 360
aaagaatgac tttggcactc ttcaccagag tggggtgtcc cgctcgtgtg tgcaaatagg 420
ctcccactgg tcaccccgga ttttgcagaa aaacagcaag ttccggggtg tctcactggt 480
gtccgccaat aagaggagcc ggcaggcacg gagtctacat caagctgtct ccgatacact 540
cgactaccat ccgggtctct cagagagcgg aatggcacta taaataccgc ctccttgcgc 600
tctctgcctt catcaatcaa atc 623

<210> SEQ ID NO 47
<211> LENGTH: 623
<212> TYPE: DNA

<213> ORGANISM: Artificial Sequence
<220> FEATURE:
<223> OTHER INFORMATION: FMD variant v13

<400> SEQUENCE: 47
aatgtatcta aacgcaaact ccgagctgga aaaatgttac cggcgatgcg cggacaattt 60
agaggcggcg atcaagaaac acctgctggg cgagcagtct ggagcacagt cttcgatggg 120
cccgagatcc caccgcgttc ctgggtaccg ggacgtgagg cagcgcgaca tccatcaaat 180
ataccaggcg ccaaccgagt ctctcggaaa acagcttctg gatatcttcc gctggcggcg 240
caacgacgaa taatagtccc tggaggtgac ggaatatata tgtgtggagg gtaaatctga 300
cagggtgtag caaaggtaat attttcctaa aacatgcaat cggctgcccc gcaacgggaa 360
aaagaatgac tttggcactc ttcaccagag tggggtgtcc cgctcgtgtg tgcaaatagg 420
ctcccactgg tcaccccgga ttttgcagaa aaacagcaag ttccggggtg tctcactggt 480
gtccgccaat aagaggagcc ggcaggcacg gagtctacat caagctgtct ccgatacact 540
cgactaccat ccgggtctct cagagaggcg aatggcacta taaataccgc ctccttgcgc 600
tctctgcctt catcaatcaa atc 623

<210> SEQ ID NO 48
<211> LENGTH: 623
<212> TYPE: DNA
<213> ORGANISM: Artificial Sequence
<220> FEATURE:
<223> OTHER INFORMATION: FMD variant v14

<400> SEQUENCE: 48
aatgtatcta aacgcaaact ccgagctgga aaaatgttac cggcgatgcg cggacaattt 60
agaggcggcg atcaagaaac acctgctggg cgagcagtct ggagcacagt cttcgatggg 120
cccgagatcc caccgcgttc ctgggtaccg ggacgtgagg cagcgcgaca tccatcaaat 180
ataccaggcg ccaaccgagt ctctcggaaa acagcttctg gatatcttcc gctggcggcg 240
caacgacgaa taatagtccc tggaggtgac ggaatatata tgtgtggagg gtaaatctga 300
cagggtgtag caaaggtaat attttcctaa aacatgcaat cggctgcccc gcaacgggaa 360
aaagaatgac tttggcactc ttcaccagag tggggtgtcc cgctcgtgtg tgcaaatagg 420
ctcccactgg tcaccccgga ttttgcagaa aaacagcaag ttccggggtg tctcactggt 480
gtccgccaat aagaggagcc ggcaggcacg gagtctacat caagctgtct ccgatacact 540
cgactaccat ccgggtctct cagagagggc aatggcacta taaataccgc ctccttgcgc 600
tctctgcctt catcaatcaa atc 623

<210> SEQ ID NO 49
<211> LENGTH: 623
<212> TYPE: DNA
<213> ORGANISM: Artificial Sequence
<220> FEATURE:
<223> OTHER INFORMATION: FMD variant v15

<400> SEQUENCE: 49
aatgtatcta aacgcaaact ccgagctgga aaaatgttac cggcgatgcg cggacaattt 60
agaggcggcg atcaagaaac acctgctggg cgagcagtct ggagcacagt cttcgatggg 120
cccgagatcc caccgcgttc ctgggtaccg ggacgtgagg cagcgcgaca tccatcaaat 180
ataccaggcg ccaaccgagt ctctcggaaa acagcttctg gatatcttcc gctggcggcg 240
caacgacgaa taatagtccc tggaggtgac ggaatatata tgtgtggagg gtaaatctga 300
cagggtgtag caaaggtaat attttcctaa aacatgcaat cggctgcccc gcaacgggaa 360
aaagaatgac tttggcactc ttcaccagag tggggtgtcc cgctcgtgtg tgcaaatagg 420
ctcccactgg tcaccccgga ttttgcagaa aaacagcaag ttccggggtg tctcactggt 480
gtccgccaat aagaggagcc ggcaggcacg gagtctacat caagctgtct ccgatacact 540
cgactaccat ccgggtctct cagagagggg catggcacta taaataccgc ctccttgcgc 600
tctctgcctt catcaatcaa atc 623

<210> SEQ ID NO 50
<211> LENGTH: 623
<212> TYPE: DNA
<213> ORGANISM: Artificial Sequence
<220> FEATURE:
<223> OTHER INFORMATION: FMD variant v16

<400> SEQUENCE: 50
aatgtatcta aacgcaaact ccgagctgga aaaatgttac cggcgatgcg cggacaattt 60
agaggcggcg atcaagaaac acctgctggg cgagcagtct ggagcacagt cttcgatggg 120
cccgagatcc caccgcgttc ctgggtaccg ggacgtgagg cagcgcgaca tccatcaaat 180
ataccaggcg ccaaccgagt ctctcggaaa acagcttctg gatatcttcc gctggcggcg 240
caacgacgaa taatagtccc tggaggtgac ggaatatata tgtgtggagg gtaaatctga 300
cagggtgtag caaaggtaat attttcctaa aacatgcaat cggctgcccc gcaacgggaa 360
aaagaatgac tttggcactc ttcaccagag tggggtgtcc cgctcgtgtg tgcaaatagg 420
ctcccactgg tcaccccgga ttttgcagaa aaacagcaag ttccggggtg tctcactggt 480
gtccgccaat aagaggagcc ggcaggcacg gagtctacat caagctgtct ccgatacact 540
cgactaccat ccgggtctct cagagagggg actggcacta taaataccgc ctccttgcgc 600
tctctgcctt catcaatcaa atc 623

<210> SEQ ID NO 51
<211> LENGTH: 623
<212> TYPE: DNA
<213> ORGANISM: Artificial Sequence
<220> FEATURE:
<223> OTHER INFORMATION: FMD variant v17

<400> SEQUENCE: 51
aatgtatcta aacgcaaact ccgagctgga aaaatgttac cggcgatgcg cggacaattt 60
agaggcggcg atcaagaaac acctgctggg cgagcagtct ggagcacagt cttcgatggg 120
cccgagatcc caccgcgttc ctgggtaccg ggacgtgagg cagcgcgaca tccatcaaat 180
ataccaggcg ccaaccgagt ctctcggaaa acagcttctg gatatcttcc gctggcggcg 240
caacgacgaa taatagtccc tggaggtgac ggaatatata tgtgtggagg gtaaatctga 300
cagggtgtag caaaggtaat attttcctaa aacatgcaat cggctgcccc gcaacgggaa 360
aaagaatgac tttggcactc ttcaccagag tggggtgtcc cgctcgtgtg tgcaaatagg 420
ctcccactgg tcaccccgga ttttgcagaa aaacagcaag ttccggggtg tctcactggt 480
gtccgccaat aagaggagcc ggcaggcacg gagtctacat caagctgtct ccgatacact 540
cgactaccat ccgggtctct cagagagggg aacggcacta taaataccgc ctccttgcgc 600
tctctgcctt catcaatcaa atc 623

<210> SEQ ID NO 52

-continued

<211> LENGTH: 623
<212> TYPE: DNA
<213> ORGANISM: Artificial Sequence
<220> FEATURE:
<223> OTHER INFORMATION: FMD variant v18

<400> SEQUENCE: 52

```
aatgtatcta aacgcaaact ccgagctgga aaaatgttac cggcgatgcg cggacaattt     60

agaggcggcg atcaagaaac acctgctggg cgagcagtct ggagcacagt cttcgatggg    120

cccgagatcc caccgcgttc ctgggtaccg ggacgtgagg cagcgcgaca tccatcaaat    180

ataccaggcg ccaaccgagt ctctcggaaa acagcttctg gatatcttcc gctggcggcg    240

caacgacgaa taatagtccc tggaggtgac ggaatatata tgtgtggagg gtaaatctga    300

cagggtgtag caaaggtaat attttcctaa aacatgcaat cggctgcccc gcaacgggaa    360

aaagaatgac tttggcactc ttcaccagag tggggtgtcc cgctcgtgtg tgcaaatagg    420

ctcccactgg tcaccccgga ttttgcagaa aaacagcaag ttccggggtg tctcactggt    480

gtccgccaat aagaggagcc ggcaggcacg gagtctacat caagctgtct ccgatacact    540

cgactaccat ccgggtctct cagagagggg aatcgcacta taaataccgc ctccttgcgc    600

tctctgcctt catcaatcaa atc                                            623
```

<210> SEQ ID NO 53
<211> LENGTH: 623
<212> TYPE: DNA
<213> ORGANISM: Artificial Sequence
<220> FEATURE:
<223> OTHER INFORMATION: FMD variant v19

<400> SEQUENCE: 53

```
aatgtatcta aacgcaaact ccgagctgga aaaatgttac cggcgatgcg cggacaattt     60

agaggcggcg atcaagaaac acctgctggg cgagcagtct ggagcacagt cttcgatggg    120

cccgagatcc caccgcgttc ctgggtaccg ggacgtgagg cagcgcgaca tccatcaaat    180

ataccaggcg ccaaccgagt ctctcggaaa acagcttctg gatatcttcc gctggcggcg    240

caacgacgaa taatagtccc tggaggtgac ggaatatata tgtgtggagg gtaaatctga    300

cagggtgtag caaaggtaat attttcctaa aacatgcaat cggctgcccc gcaacgggaa    360

aaagaatgac tttggcactc ttcaccagag tggggtgtcc cgctcgtgtg tgcaaatagg    420

ctcccactgg tcaccccgga ttttgcagaa aaacagcaag ttccggggtg tctcactggt    480

gtccgccaat aagaggagcc ggcaggcacg gagtctacat caagctgtct ccgatacact    540

cgactaccat ccgggtctct cagagagggg aatgccacta taaataccgc ctccttgcgc    600

tctctgcctt catcaatcaa atc                                            623
```

<210> SEQ ID NO 54
<211> LENGTH: 648
<212> TYPE: DNA
<213> ORGANISM: Artificial Sequence
<220> FEATURE:
<223> OTHER INFORMATION: FMD variant v20

<400> SEQUENCE: 54

```
aatgtatcta aacgcaaact ccgagctgga aaaatgttac cggcgatgcg cggacaattt     60

agaggcggcg atcaagaaac acctgctggg cgagcagtct ggagcacagt cttcgatggg    120

cccgagatcc caccgcgttc ctgggtaccg ggacgtgagg cagcgcgaca tccatcaaat    180

ataccaggcg ccaaccgagt ctctcggaaa acagcttctg gatatcttcc gctggcggcg    240
```

caacgacgaa taatagtccc tggaggtgac ggaatatata tgtgtggagg gtaaatctga 300
cagggtgtag caaaggtaat attttcctaa aacatgcaat cggctgcccc gcaacgggaa 360
aaagaatgac tttggcactc ttcaccagag tggggtgtcc cgctcgtgtg tgcaaatagg 420
ctcccactgg tcaccccgga ttttgcagaa aaacagcaag ttccggggtg tctcactggt 480
gtccgccaat aagaggagcc ggcaggcacg gagtctacat caagctgtct ccgatacact 540
cgactaccat ccgggtctct cagagagggg aatggcacta tataaactgg tgataattcc 600
ttcgttctga gttccatctc atactcaaac tatattaaaa ctacaaca 648

<210> SEQ ID NO 55
<211> LENGTH: 639
<212> TYPE: DNA
<213> ORGANISM: Artificial Sequence
<220> FEATURE:
<223> OTHER INFORMATION: FMD variant v21

<400> SEQUENCE: 55
aatgtatcta aacgcaaact ccgagctgga aaaatgttac cggcgatgcg cggacaattt 60
agaggcggcg atcaagaaac acctgctggg cgagcagtct ggagcacagt cttcgatggg 120
cccgagatcc caccgcgttc ctgggtaccg ggacgtgagg cagcgcgaca tccatcaaat 180
ataccaggcg ccaaccgagt ctctcggaaa acagcttctg gatatcttcc gctggcggcg 240
caacgacgaa taatagtccc tggaggtgac ggaatatata tgtgtggagg gtaaatctga 300
cagggtgtag caaaggtaat attttcctaa aacatgcaat cggctgcccc gcaacgggaa 360
aaagaatgac tttggcactc ttcaccagag tggggtgtcc cgctcgtgtg tgcaaatagg 420
ctcccactgg tcaccccgga ttttgcagaa aaacagcaag ttccggggtg tctcactggt 480
gtccgccaat aagaggagcc ggcaggcacg gagtctacat caagctgtct ccgatacact 540
cgactaccat ccgggtctct cagagagggg aatggcacta taaatacaag acgagtgcgt 600
ccttttctag actcacccat aaacaaataa tcaataaat 639

<210> SEQ ID NO 56
<211> LENGTH: 623
<212> TYPE: DNA
<213> ORGANISM: Artificial Sequence
<220> FEATURE:
<223> OTHER INFORMATION: FMD variant v22

<400> SEQUENCE: 56
aatgtatcta aacgcaaact ccgagctgga aaaatgttac cggcgatgcg cggacaattt 60
agaggcggcg atcaagaaac acctgctggg cgagcagtct ggagcacagt cttcgatggg 120
cccgagatcc caccgcgttc ctgggtaccg ggacgtgagg cagcgcgaca tccatcaaat 180
ataccaggcg ccaaccgagt ctctcggaaa acagcttctg gatatcttcc gctggcggcg 240
caacgacgaa taatagtccc tggaggtgac ggaatatata tgtgtggagg gtaaatctga 300
cagggtgtag caaaggtaat attttcctaa aacatgcaat cggctgcccc gcaacgggaa 360
aaagaatgac tttggcactc ttcaccagag tggggtgtcc cgctcgtgtg tgcaaatagg 420
ctcccactgg tcaccccgga ttttgcagaa aaacagcaag ttccggggtg tctcactggt 480
gtccgccaat aagaggagcc ggcaggcacg gagtctacat caagctgtct ccgatacact 540
cgactaccat ccgggtctct cagagagggg aatggcacta taaatactgc ctacttgtcc 600
tctattcctt catcaatcac atc 623

<210> SEQ ID NO 57
<211> LENGTH: 721
<212> TYPE: DNA
<213> ORGANISM: Artificial Sequence
<220> FEATURE:
<223> OTHER INFORMATION: FMD variant v23

<400> SEQUENCE: 57
aatgtatcta aacgcaaact ccgagctgga aaaatgttac cggcgatgcg cggacaattt 60
agaggcggcg atcaagaaac acctgctggg cgagcagtct ggagcacagt cttcgatggg 120
cccgagatcc caccgcgttc ctgggtaccg ggacgtgagg cagcgcgaca tccatcaaat 180
ataccaggcg ccaaccgagt ctctcggaaa acagcttctg gatatcttcc gctggcggcg 240
caacgacgaa taatagtccc tggaggtgac ggaatatata tgtgtggagg gtaaatctga 300
cagggtgtag caaaggtaat attttcctaa aacatgcaat cggctgcccc gcaacgggaa 360
aaagaatgac tttggcactc ttcaccagag tggggtgtcc cgctcgtgtg tgcaaatagg 420
ctcccactgg tcaccccgga ttttgcagaa aaacagcaag ttccggggtg tctcactggt 480
gtccgccaat aagaggagcc ggcaggcacg gagtctacat caagctgtct ccgatacact 540
cgactaccat ccgggtctct cagagagggg aatggcaccg atagggcaga aatatataaa 600
gtaggaggtt gtataccaaa tataccaacg cagtacaagc aactcttggt ttaaacggaa 660
gaaacaattc ttcgaacatt tacaacaaag aaggtaccgt aacattaata atcggaaggg 720
t 721

<210> SEQ ID NO 58
<211> LENGTH: 721
<212> TYPE: DNA
<213> ORGANISM: Artificial Sequence
<220> FEATURE:
<223> OTHER INFORMATION: FMD variant v24

<400> SEQUENCE: 58
aatgtatcta aacgcaaact ccgagctgga aaaatgttac cggcgatgcg cggacaattt 60
agaggcggcg atcaagaaac acctgctggg cgagcagtct ggagcacagt cttcgatggg 120
cccgagatcc caccgcgttc ctgggtaccg ggacgtgagg cagcgcgaca tccatcaaat 180
ataccaggcg ccaaccgagt ctctcggaaa acagcttctg gatatcttcc gctggcggcg 240
caacgacgaa taatagtccc tggaggtgac ggaatatata tgtgtggagg gtaaatctga 300
cagggtgtag caaaggtaat attttcctaa aacatgcaat cggctgcccc gcaacgggaa 360
aaagaatgac tttggcactc ttcaccagag tggggtgtcc cgctcgtgtg tgcaaatagg 420
ctcccactgg tcaccccgga ttttgcagaa aaacagcaag ttccggggtg tctcactggt 480
gtccgccaat aagaggagcc ggcaggcacg gagtctacat caagctgtct ccgatacact 540
cgactaccat ccgggtctct cagagagggg aatggcacgt aatctttcgg tcaattgtga 600
tctctcttgt agatatttaa taggacggcc aaggtagaaa aagatacata actagttagc 660
aaacttcaat tgcttaagtt acaagtgcaa tccatatctt aaagttatta cattatttat 720
a 721

<210> SEQ ID NO 59
<211> LENGTH: 721
<212> TYPE: DNA
<213> ORGANISM: Artificial Sequence
<220> FEATURE:
<223> OTHER INFORMATION: FMD variant v25

<400> SEQUENCE: 59
aatgtatcta aacgcaaact ccgagctgga aaaatgttac cggcgatgcg cggacaattt 60
agaggcggcg atcaagaaac acctgctggg cgagcagtct ggagcacagt cttcgatggg 120
cccgagatcc caccgcgttc ctgggtaccg ggacgtgagg cagcgcgaca tccatcaaat 180
ataccaggcg ccaaccgagt ctctcggaaa acagcttctg gatatcttcc gctggcggcg 240
caacgacgaa taatagtccc tggaggtgac ggaatatata tgtgtggagg gtaaatctga 300
cagggtgtag caaaggtaat attttcctaa aacatgcaat cggctgcccc gcaacgggaa 360
aaagaatgac tttggcactc ttcaccagag tggggtgtcc cgctcgtgtg tgcaaatagg 420
ctcccactgg tcaccccgga ttttgcagaa aaacagcaag ttccggggtg tctcactggt 480
gtccgccaat aagaggagcc ggcaggcacg gagtctacat caagctgtct ccgatacact 540
cgactaccat ccgggtctct cagagagggg aatggcaccc tcctctaggt ttatctataa 600
aagctgaagt cgttagaatt tttcatttaa agcataatca aacatctaga ttcgaatcga 660
taaaaagcag atagaagtta ttaagattat aggttacatt ctagagtagt ataggaaggt 720
a 721

<210> SEQ ID NO 60
<211> LENGTH: 28
<212> TYPE: DNA
<213> ORGANISM: Artificial Sequence
<220> FEATURE:
<223> OTHER INFORMATION: Primer

<400> SEQUENCE: 60
gccaattctc aatttgctag agactctg 28

<210> SEQ ID NO 61
<211> LENGTH: 24
<212> TYPE: DNA
<213> ORGANISM: Artificial Sequence
<220> FEATURE:
<223> OTHER INFORMATION: Primer

<400> SEQUENCE: 61
agaggcggcg aatcaagaaa cacc 24

<210> SEQ ID NO 62
<211> LENGTH: 24
<212> TYPE: DNA
<213> ORGANISM: Artificial Sequence
<220> FEATURE:
<223> OTHER INFORMATION: Primer

<400> SEQUENCE: 62
ggtgtttctt gattcgccgc ctct 24

<210> SEQ ID NO 63
<211> LENGTH: 25
<212> TYPE: DNA
<213> ORGANISM: Artificial Sequence
<220> FEATURE:
<223> OTHER INFORMATION: Primer

<400> SEQUENCE: 63
ctgccccgcg acgggaaaaa gaatg 25

<210> SEQ ID NO 64

<211> LENGTH: 25
<212> TYPE: DNA
<213> ORGANISM: Artificial Sequence
<220> FEATURE:
<223> OTHER INFORMATION: Primer

<400> SEQUENCE: 64
cattcttttt cccgtcgcgg ggcag 25

<210> SEQ ID NO 65
<211> LENGTH: 30
<212> TYPE: DNA
<213> ORGANISM: Artificial Sequence
<220> FEATURE:
<223> OTHER INFORMATION: Primer

<400> SEQUENCE: 65
ggattttgca gaaaaatagc aagttccggg 30

<210> SEQ ID NO 66
<211> LENGTH: 30
<212> TYPE: DNA
<213> ORGANISM: Artificial Sequence
<220> FEATURE:
<223> OTHER INFORMATION: Primer

<400> SEQUENCE: 66
cccggaactt gctatttttc tgcaaaatcc 30

<210> SEQ ID NO 67
<211> LENGTH: 22
<212> TYPE: DNA
<213> ORGANISM: Artificial Sequence
<220> FEATURE:
<223> OTHER INFORMATION: Primer

<400> SEQUENCE: 67
gtctctcaga gggggaatg gc 22

<210> SEQ ID NO 68
<211> LENGTH: 22
<212> TYPE: DNA
<213> ORGANISM: Artificial Sequence
<220> FEATURE:
<223> OTHER INFORMATION: Primer

<400> SEQUENCE: 68
gccattcccc cctctgagag ac 22

<210> SEQ ID NO 69
<211> LENGTH: 25
<212> TYPE: DNA
<213> ORGANISM: Artificial Sequence
<220> FEATURE:
<223> OTHER INFORMATION: Primer

<400> SEQUENCE: 69
cactcgacta ccagccgggt ctctc 25

<210> SEQ ID NO 70
<211> LENGTH: 25
<212> TYPE: DNA
<213> ORGANISM: Artificial Sequence
<220> FEATURE:
<223> OTHER INFORMATION: Primer

<400> SEQUENCE: 70
gagagacccg gctggtagtc gagtg 25

<210> SEQ ID NO 71
<211> LENGTH: 51
<212> TYPE: DNA
<213> ORGANISM: Artificial Sequence
<220> FEATURE:
<223> OTHER INFORMATION: Primer

<400> SEQUENCE: 71
cactcgacta ccatccgggt ctctccgaga ggggaatggc actataaata c 51

<210> SEQ ID NO 72
<211> LENGTH: 51
<212> TYPE: DNA
<213> ORGANISM: Artificial Sequence
<220> FEATURE:
<223> OTHER INFORMATION: Primer

<400> SEQUENCE: 72
cactcgacta ccatccgggt ctctcacaga ggggaatggc actataaata c 51

<210> SEQ ID NO 73
<211> LENGTH: 51
<212> TYPE: DNA
<213> ORGANISM: Artificial Sequence
<220> FEATURE:
<223> OTHER INFORMATION: Primer

<400> SEQUENCE: 73
cactcgacta ccatccgggt ctctcagcga ggggaatggc actataaata c 51

<210> SEQ ID NO 74
<211> LENGTH: 51
<212> TYPE: DNA
<213> ORGANISM: Artificial Sequence
<220> FEATURE:
<223> OTHER INFORMATION: Primer

<400> SEQUENCE: 74
cactcgacta ccatccgggt ctctcagaca ggggaatggc actataaata c 51

<210> SEQ ID NO 75
<211> LENGTH: 51
<212> TYPE: DNA
<213> ORGANISM: Artificial Sequence
<220> FEATURE:
<223> OTHER INFORMATION: Primer

<400> SEQUENCE: 75
cactcgacta ccatccgggt ctctcagagc ggggaatggc actataaata c 51

<210> SEQ ID NO 76
<211> LENGTH: 51
<212> TYPE: DNA
<213> ORGANISM: Artificial Sequence
<220> FEATURE:
<223> OTHER INFORMATION: Primer

<400> SEQUENCE: 76
cactcgacta ccatccgggt ctctcagaga cgggaatggc actataaata c 51

<210> SEQ ID NO 77
<211> LENGTH: 51
<212> TYPE: DNA

<213> ORGANISM: Artificial Sequence
<220> FEATURE:
<223> OTHER INFORMATION: Primer

<400> SEQUENCE: 77
cactcgacta ccatccgggt ctctcagaga gcggaatggc actataaata c 51

<210> SEQ ID NO 78
<211> LENGTH: 51
<212> TYPE: DNA
<213> ORGANISM: Artificial Sequence
<220> FEATURE:
<223> OTHER INFORMATION: Primer

<400> SEQUENCE: 78
cactcgacta ccatccgggt ctctcagaga ggcgaatggc actataaata c 51

<210> SEQ ID NO 79
<211> LENGTH: 51
<212> TYPE: DNA
<213> ORGANISM: Artificial Sequence
<220> FEATURE:
<223> OTHER INFORMATION: Primer

<400> SEQUENCE: 79
cactcgacta ccatccgggt ctctcagaga gggcaatggc actataaata c 51

<210> SEQ ID NO 80
<211> LENGTH: 51
<212> TYPE: DNA
<213> ORGANISM: Artificial Sequence
<220> FEATURE:
<223> OTHER INFORMATION: Primer

<400> SEQUENCE: 80
cactcgacta ccatccgggt ctctcagaga ggggcatggc actataaata c 51

<210> SEQ ID NO 81
<211> LENGTH: 51
<212> TYPE: DNA
<213> ORGANISM: Artificial Sequence
<220> FEATURE:
<223> OTHER INFORMATION: Primer

<400> SEQUENCE: 81
cactcgacta ccatccgggt ctctcagaga ggggactggc actataaata c 51

<210> SEQ ID NO 82
<211> LENGTH: 51
<212> TYPE: DNA
<213> ORGANISM: Artificial Sequence
<220> FEATURE:
<223> OTHER INFORMATION: Primer

<400> SEQUENCE: 82
cactcgacta ccatccgggt ctctcagaga ggggaacggc actataaata c 51

<210> SEQ ID NO 83
<211> LENGTH: 51
<212> TYPE: DNA
<213> ORGANISM: Artificial Sequence
<220> FEATURE:
<223> OTHER INFORMATION: Primer

<400> SEQUENCE: 83
cactcgacta ccatccgggt ctctcagaga ggggaatcgc actataaata c 51

<210> SEQ ID NO 84
<211> LENGTH: 51
<212> TYPE: DNA
<213> ORGANISM: Artificial Sequence
<220> FEATURE:
<223> OTHER INFORMATION: Primer

<400> SEQUENCE: 84
cactcgacta ccatccgggt ctctcagaga ggggaatgcc actataaata c 51

<210> SEQ ID NO 85
<211> LENGTH: 21
<212> TYPE: DNA
<213> ORGANISM: Artificial Sequence
<220> FEATURE:
<223> OTHER INFORMATION: Primer

<400> SEQUENCE: 85
gagagacccg gatggtagtc g 21

<210> SEQ ID NO 86
<211> LENGTH: 60
<212> TYPE: DNA
<213> ORGANISM: Artificial Sequence
<220> FEATURE:
<223> OTHER INFORMATION: Primer

<400> SEQUENCE: 86
ctcatactca aactatatta aaactacaac aatggctagc aaaggagaag aacttttcac 60

<210> SEQ ID NO 87
<211> LENGTH: 90
<212> TYPE: DNA
<213> ORGANISM: Artificial Sequence
<220> FEATURE:
<223> OTHER INFORMATION: Primer

<400> SEQUENCE: 87
tgttgtagtt ttaatatagt ttgagtatga gatggaactc agaacgaagg aattatcacc 60
agtttatata gtgccattcc cctctctgag 90

<210> SEQ ID NO 88
<211> LENGTH: 59
<212> TYPE: DNA
<213> ORGANISM: Artificial Sequence
<220> FEATURE:
<223> OTHER INFORMATION: Primer

<400> SEQUENCE: 88
gactcaccca taaacaaata atcaataaat atggctagca aaggagaaga acttttcac 59

<210> SEQ ID NO 89
<211> LENGTH: 81
<212> TYPE: DNA
<213> ORGANISM: Artificial Sequence
<220> FEATURE:
<223> OTHER INFORMATION: Primer

<400> SEQUENCE: 89
atttattgat tatttgttta tgggtgagtc tagaaaagga cgcactcgtc ttgtatttat 60
agtgccattc ccctctctga g 81

<210> SEQ ID NO 90

<211> LENGTH: 60
<212> TYPE: DNA
<213> ORGANISM: Artificial Sequence
<220> FEATURE:
<223> OTHER INFORMATION: Primer

<400> SEQUENCE: 90
acttgtcctc tattccttca tcaatcacat catggctagc aaaggagaag aacttttcac 60

<210> SEQ ID NO 91
<211> LENGTH: 65
<212> TYPE: DNA
<213> ORGANISM: Artificial Sequence
<220> FEATURE:
<223> OTHER INFORMATION: Primer

<400> SEQUENCE: 91
gatgtgattg atgaaggaat agaggacaag taggcagtat ttatagtgcc attcccctct 60
ctgag 65

<210> SEQ ID NO 92
<211> LENGTH: 250
<212> TYPE: DNA
<213> ORGANISM: Artificial Sequence
<220> FEATURE:
<223> OTHER INFORMATION: Primer

<400> SEQUENCE: 92
atcaagctgt ctccgataca ctcgactacc atccgggtct ctcagagagg ggaatggcac 60
cgatagggca gaaatatata aagtaggagg ttgtatacca aatataccaa cgcagtacaa 120
gcaactcttg gtttaaacgg aagaaacaat tcttcgaaca tttacaacaa agaaggtacc 180
gtaacattaa taatcggaag ggtatggcta gcaaaggaga agaacttttc actggagttg 240
tcccaattct 250

<210> SEQ ID NO 93
<211> LENGTH: 250
<212> TYPE: DNA
<213> ORGANISM: Artificial Sequence
<220> FEATURE:
<223> OTHER INFORMATION: Primer

<400> SEQUENCE: 93
atcaagctgt ctccgataca ctcgactacc atccgggtct ctcagagagg ggaatggcac 60
gtaatctttc ggtcaattgt gatctctctt gtagatattt aataggacgg ccaaggtaga 120
aaaagataca taactagtta gcaaacttca attgcttaag ttacaagtgc aatccatatc 180
ttaaagttat tacattattt ataatggcta gcaaaggaga agaacttttc actggagttg 240
tcccaattct 250

<210> SEQ ID NO 94
<211> LENGTH: 250
<212> TYPE: DNA
<213> ORGANISM: Artificial Sequence
<220> FEATURE:
<223> OTHER INFORMATION: Primer -continued

```
<400> SEQUENCE: 94

atcaagctgt ctccgataca ctcgactacc atccgggtct ctcagagagg ggaatggcac     60

cctcctctag gtttatctat aaaagctgaa gtcgttagaa tttttcattt aaagcataat    120

caaacatcta gattcgaatc gataaaaagc agatagaagt tattaagatt ataggttaca    180

ttctagagta gtataggaag gtaatggcta gcaaaggaga agaacttttc actggagttg    240

tcccaattct                                                            250
```